(12) United States Patent
Mattson

(10) Patent No.: US 6,822,100 B2
(45) Date of Patent: Nov. 23, 2004

(54) CYCLOPROPYLINDOLE DERIVATIVES AS SELECTIVE SEROTONIN REUPTAKE INHIBITORS

(75) Inventor: Ronald J. Mattson, Meriden, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 10/713,893

(22) Filed: Nov. 14, 2003

(65) Prior Publication Data

US 2004/0143003 A1 Jul. 22, 2004

Related U.S. Application Data

(62) Division of application No. 10/091,232, filed on Mar. 5, 2002.
(60) Provisional application No. 60/327,804, filed on Oct. 9, 2001, provisional application No. 60/293,122, filed on May 23, 2001, and provisional application No. 60/279,888, filed on Mar. 29, 2001.

(51) Int. Cl.$^7$ .......................................... G07D 209/04
(52) U.S. Cl. ................................................... 548/469
(58) Field of Search ......................................... 548/469

(56) References Cited

U.S. PATENT DOCUMENTS

| | | | | |
|---|---|---|---|---|
| 5,468,767 A | 11/1995 | Cipollina et al. | ............ | 514/414 |
| 5,468,768 A | 11/1995 | Cipollina et al. | ............ | 514/415 |
| 5,583,149 A | 12/1996 | Cipollina et al. | ............ | 514/339 |
| 5,604,253 A | * 2/1997 | Lau et al. | .................... | 514/415 |
| 5,607,961 A | 3/1997 | Cipollina et al. | ............ | 514/415 |
| 6,239,129 B1 | 5/2001 | Lavielle et al. | ............. | 514/218 |

FOREIGN PATENT DOCUMENTS

| | | |
|---|---|---|
| EP | 0 253 498 | 1/1988 |
| WO | WO 99/10346 | 3/1999 |
| WO | WO 99/51576 | 10/1999 |
| WO | WO 99/58525 | 11/1999 |
| WO | WO 99/62515 | 12/1999 |
| WO | WO 00/31074 | 6/2000 |
| WO | WO 00/40554 | 7/2000 |
| WO | WO 00/40579 | 7/2000 |
| WO | WO 00/40580 | 7/2000 |
| WO | WO 00/40581 | 7/2000 |
| WO | WO 00/49017 | 8/2000 |
| WO | WO 01/17521 | 3/2001 |

OTHER PUBLICATIONS

Vangveravong et al., "Synthesis and Serotonin Receptor Affinities of a Series of trans–2–(Indol–3–yl)cyclopropylamine Derivatives," J. Med. Chem., 1998, 41, 4995–5001.

Waldinger, et al., "Premature ejaculation and serotonergic antidepressants–induced delayed ejaculation: the involvement of the serotonergic system," Behavioural Brain Research, 92, 1998, 111–118.

Horwell, et al., "Conformationally Constrained Amino–Acids: Synthesis of Novel β, β–, 2,3–, and 3,4–Cyclised Tyrptophans," Tetrahedron Letters, 39, 1998, pp. 8729–8732.

Haensel, et al., "Clomipramine and Sexual Function with Men in Premature Ejaculation and Controls," J. of Urology, 156, Oct. 1996, pp. 1310–1315.

McMahon, et al., "Treatment of Premature Ejaculation with Paroxetine Hydrochloride," International Journal of Impotence Research, 11, 1999, pp. 241–246.

Fuller, "Pharmacologic Modification of Serotonergic Function: Drugs for the Study and Treatment of Psychiatric and Other Disorders," J. Clin. Psychiatry, 47:4 (Suppl.), Apr. 1986, pp. 4–8.

Kim, et al., "Short–Term Analysis of the Effects of As Needed Use of Sertraline at 5 p.m. for the Treatment of Premature Ejaculation," Urology, 54 (3), 1999, pp. 544–547.

McMahon, et al., "Treatment of Premature Ejaculation with Paroxetine Hydrochloride As Needed: 2 Single–Blind Placebo Controlled Crossover Studies," J. of Urology, 161, Jun. 1999, pp. 1826–1830.

* cited by examiner

Primary Examiner—Kamal Saeed
(74) Attorney, Agent, or Firm—Shah R. Makujina

(57) ABSTRACT

The present invention relates to processes for the preparation of Formula (I)

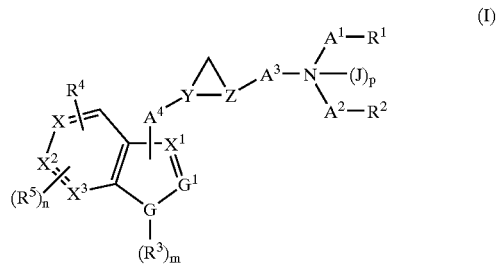

and pharmaceutically acceptable salts or solvates thereof useful for the treatment of depression, anxiety disorders, premature ejaculation, chronic pain, obsessive-compulsive disorder, feeding disorders, premenstrual dysphoric disorder, panic disorders and psychotic disorders including bipolar disorder and schizophrenia.

2 Claims, No Drawings

CYCLOPROPYLINDOLE DERIVATIVES AS SELECTIVE SEROTONIN REUPTAKE INHIBITORS

CROSS REFERENCES TO RELATED APPLICATIONS

This divisional application claims priority from non-provisional application U.S. Ser. No. 10/091,232 filed Mar. 5, 2002 which claims priority from provisional applications U.S. Ser. No. 60/279,888 filed Mar. 29, 2001, U.S. Ser. No. 60/293,122 filed May 23, 2001 and U.S. Ser. No. 60/327,804 filed Oct. 9, 2001.

FIELD OF THE INVENTION

The present invention relates to cyclopropylindole derivatives and pharmaceutical compositions comprising said derivatives useful for the treatment of various psychiatric disorders and premature ejaculation.

BACKGROUND OF THE INVENTION

Selective serotonin reuptake inhibitors (SSRIs) are effective for the treatment of mental depression and have been reported to be useful for treating chronic pain. See R. W. Fuller, Pharmacologic Modification of Serotonergic Function: Drugs for the Study and Treatment of Psychiatric and Other Disorders," *J. Clin. Psychiatry*, 47:4 (Suppl.) April 1986, pp. 4–8 and *Selective Serotonin Reuptake Inhibitors*, edited by J P Feighner and W F Boyer, Chichester, England. John Wiley & Sons, 1991, pp. 89–108. SSRI's have also demonstrated efficacy for the treatment of anxiety disorders. More recently, SSRI's have demonstrated efficacy in the treatment of premature ejaculation. See Kim and Paick, Short-term Analysis of the Effects of As Needed Use of Sertraline at 5 pm for the Treatment of Premature Ejaculation, *Urology* 54:544–547 (1999); McMahon and Touma, Treatment of Premature Ejaculation with Paroxetine Hydrochloride As Needed: 2 Single-Blind Placebo Controlled Crossover Studies *Journal of Urology* 161:1826–1830 (1999); Haensal et al., Clomipramine and sexual function in men with premature ejaculation and controls *Journal of Urology* 156:1310–1315 (1996); and McMahon and Touma, Treatment of Premature Ejaculation with Paraoxetine Hydrochloride *International Journal Impotence Research* 11:241–246 (1999). Thus novel SSRI's effective for the treatment of these and other disorders would be greatly advantageous.

SUMMARY OF THE INVENTION

Thus according to a first embodiment of a first aspect of the present invention are provided compounds of Formula (I)

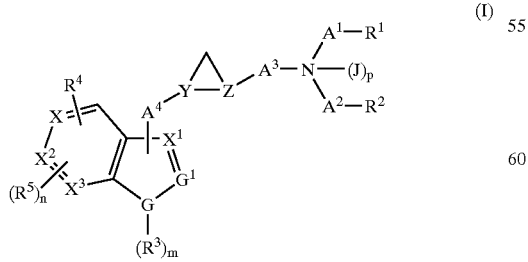

(I)

and pharmaceutically acceptable salts or solvates thereof wherein $A^1$ and $A^2$ are each independently $C_{1-4}$alkylene or a bond;

$A^3$ is $C_{1-4}$alkylene or $C_{1-4}$alkylidene;

$A^4$ is $C_{1-4}$alkylene or a bond and is attached to X, $X^1$ or $X^2$;

X, $X^1$, $X^2$ and $X^3$ are independently C or CH;

J is $C_{1-4}$alkyl;

p is 0 or 1;

$R^1$ and $R^2$ are independently H, $C_{1-3}$alkyl, $C_{3-6}$cycloalkyl, phenyl, —O-phenyl, —N(H)C(O)O—$C_{1-4}$alkyl or $C_{1-4}$alkyl-N(H)C(O)O—;

said $C_{3-6}$cycloalkyl, phenyl or O-phenyl being independently and optionally substituted with $C_{1-4}$alkyl, $C_{1-3}$alkoxy or halo;

or are independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano;

or wherein —$A^1$—$R^1$ and —$A^2$—$R^2$ together with the nitrogen to which they are attached form pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl or tetrahydroisoquinolinyl and are optionally substituted with halo, $C_{1-4}$alkyl, $C_{1-4}$alkoxy, cyano or benzyl;

$R^3$ is H or $C_{1-4}$alkyl;

m is 0 or 1;

$R^4$ and $R^5$ are independently hydrogen, cyano, halo, nitro or $C_{1-3}$perfluoroalkyl;

wherein said $R^4$ or $R^5$ may be independently attached to X, $X^1$, $X^2$ or $X^3$;

n is 0 or 1;

G is N, O or S;

$G^1$ is N or CH;

Y is (D)H wherein D is C; and

Z is (E)H wherein E is C;

provided that both $R^4$ and $R^5$ are not attached to the same of said X, $X^1$, $X^2$ or $X^3$;

if G is O or S, then m is 0;

if G is N, then m is 1;

if $R^1$ is —N(H)C(O)O$C_{1-4}$alkyl, $C_{1-4}$alkyl-N(H)C(O)O— or said heterocyclic moiety wherein said heterocyclic moiety contains a nitrogen atom and said nitrogen atom is attached to $A^1$, then $A^1$ is $C_{2-4}$alkylene;

if $R^2$ is —N(H)C(O)O$C_{1-4}$alkyl, $C_{1-4}$alkyl-N(H)C(O) O— or said heterocyclic moiety wherein said heterocyclic moiety contains a nitrogen atom and said nitrogen atom is attached to $A^2$, then $A^2$ is $C_{2-4}$alkylene;

if $R^1$ is N(H)C(O)O—$C_{1-4}$alkyl, $C_{1-4}$alkyl—N(H)C(O) O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^2$ is H or $C_{1-3}$alkyl;

if $R^2$ is —N(H)C(O)O—$C_{1-4}$alkyl, $C_{1-4}$alkyl-N(H)C(O)O— or a heterocyclic moiety selected from the group consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano, then $R^1$ is H or $C_{1-3}$alkyl;

if $A^4$, $R^4$ or $R^5$ are attached to X, then X is C;
if $A^4$, $R^4$ or $R^5$ are attached to $X^1$, then $X^1$ is C;
if $A^4$, $R^4$ or $R^5$ are attached to $X^2$, then $X^2$ is C;
if $R^4$ or $R^5$ are attached to $X^3$, then $X^3$ is C;
if $R^4$ is F and is attached to X and if $A^3$ is methylene, then —$A^1$—$R^1$ and —$A^2$—$R^2$ together with the nitrogen to which they are attached is not N-methylpiperazinyl; and
if $R^4$ is F and is attached to X and if $A^3$ is methylene, then —$A^1$—$R^1$ and —$A^2$—$R^2$ together with the nitrogen to which they are attached is not tetrahydroquinolinyl.

According to another embodiment of the first aspect of the present invention are provided compounds of Formula (I) according to the first embodiment of the first aspect wherein p is 0.

According to another embodiment of the first aspect of the present invention are provided compounds of Formula (I) according to the first embodiment of the first aspect wherein G is N and $G^1$ is CH.

According to another embodiment of the first aspect of the present invention are provided compounds of Formula (I) according to the first embodiment of the first aspect wherein G is S and $G^1$ is CH.

According to another embodiment of the first aspect of the present invention are provided compounds of Formula (I) according to the first embodiment of the first aspect wherein G is N and $G^1$ is N.

According to another embodiment of the first aspect of the present invention are provided compounds of Formula (I) according to the first embodiment of the first aspect wherein G is S and $G^1$ is N.

According to another embodiment of the first aspect of the present invention are provided compounds of Formula (I) according to the first embodiment of the first aspect wherein G is O and $G^1$ is N.

According to another embodiment of the first aspect of the present invention are provided compounds of Formula (I) according to the first embodiment of the first aspect wherein $R^1$ is methyl and $R^2$ is methyl.

According to another embodiment of the first aspect of the present invention are provided compounds of Formula (I) according to the first embodiment of the first aspect wherein $A^1$ is a bond, $R^1$ is methyl, $A^2$ is a bond and $R^2$ is methyl.

According to another embodiment of the first aspect of the present invention are provided compounds of Formula (I) according to the first embodiment of the first aspect wherein $R^3$ is H and m is 1.

According to another embodiment of the first aspect of the present invention are provided compounds of Formula (I) according to the first embodiment of the first aspect wherein $R^4$ and $R^5$ are halo.

According to another embodiment of the first aspect of the present invention are provided compounds of Formula (I) according to the first embodiment of the first aspect wherein $R^4$ is hydrogen.

According to another embodiment of the first aspect of the present invention are provided compounds of Formula (I) according to the first embodiment of the first aspect wherein $R^4$ is fluoro.

According to another embodiment of the first aspect of the present invention are provided compounds of Formula (I) according to the first embodiment of the first aspect wherein $R^4$ is cyano.

According to another embodiment of the first aspect of the present invention are provided compounds of Formula (I) according to the first embodiment of the first aspect wherein $R^4$ and $R^5$ are each fluoro.

According to another embodiment of the first aspect of the present invention are compounds of Formula (I) wherein D in relation to the four moieties to which it is attached has an absolute configuration of S; E in relation to the four moieties to which it is attached has an absolute configuration of S; and wherein the hydrogen atom attached to D is in the trans configuration to the hydrogen atom attached to E.

According to another embodiment of the first aspect of the present invention are provided compounds of Formula (I) according to the first embodiment of the first aspect wherein $A^3$ is $C_{1-4}$alkylene.

According to another embodiment of the first aspect of the present invention are provided compounds of Formula (I) according to the first embodiment of the first aspect wherein $A^3$ is $C_{1-4}$alkylidene.

According to another embodiment of the first aspect of the present invention are provided compounds of Formula (I) according to the first embodiment of the first aspect wherein $A^3$ is methylene.

According to another embodiment of the first aspect of the present invention are provided compounds of Formula (I) according to the first embodiment of the first aspect wherein $A^4$ is a bond.

According to another embodiment of the first aspect of the present invention are provided compounds of Formula (I) according to the first embodiment of the first aspect wherein $A^4$ is methylene.

According to another embodiment of the first aspect of the present invention are provided compounds of Formula (I) according to the first embodiment of the first aspect wherein $A^4$ is attached $X^1$.

According to another embodiment of the first aspect of the present invention are provided compounds of Formula (I) according to the first embodiment of the first aspect wherein $A^4$ is attached X.

According to another embodiment of the first aspect of the present invention are provided compounds of Formula (I) according to the first embodiment of the first aspect wherein $R^4$ is attached X.

According to another embodiment of the first aspect of the present invention are provided compounds of Formula (I) according to the first embodiment of the first aspect wherein $A^1$ is a bond, $A^2$ is a bond, $R^1$ is methyl and $R^2$ is methyl.

According to another embodiment of the first aspect of the present invention are provided compounds of Formula (I)

according to the first embodiment of the first aspect wherein $R^1$ is independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano; $A^1$ is $C_{1-4}$alkylene; $R^2$ is H or $C_{1-3}$alkylene; and $A^2$ is a bond.

According to another embodiment of the first aspect of the present invention are provided compounds of Formula (I) according to the first embodiment of the first aspect wherein $R^1$ is independently selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl; $A^1$ is $C_{1-4}$alkylene; $R^2$ is H or $C_{1-3}$alkylene; and $A^2$ is a bond.

According to another embodiment of the first aspect of the present invention are provided compounds of Formula (I) according to the first embodiment of the first aspect wherein $R^2$ is independently selected from the group of heterocyclic moieties consisting of thienyl, furanyl, pyrrolyl, pyrrolinyl, pyrrolidinyl, imidazolyl, imidazolinyl, imidazolidinyl, pyrazolyl, pyrazolinyl, pyrazolidinyl, pyridyl, pyrimidinyl, piperidinyl, piperazinyl, morpholino, adamantyl, indolyl, isoindolyl, indolinyl, quinolinyl, dihydroquinolinyl, tetrahydroquinolinyl, isoquinolinyl, dihydroisoquinolinyl and tetrahydroisoquinolinyl, wherein said heterocyclic moieties are optionally substituted with halo, $C_{1-4}$alkyl, $C_{1-4}$alkoxy or cyano; $A^2$ is $C_{1-4}$alkylene; $R^1$ is H or $C_{1-3}$alkylene; and $A^1$ is a bond.

According to another embodiment of the first aspect of the present invention are provided compounds of Formula (I) according to the first embodiment of the first aspect wherein $R^2$ is independently selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl; $A^2$ is $C_{1-4}$alkylene; $R^1$ is H or $C_{1-3}$alkylene; and $A^1$ is a bond.

According to another embodiment of the first aspect of the present invention are provided compounds of Formula (I) according to the first embodiment of the first aspect wherein $R^1$ and $R^2$ are independently H, $C_{1-3}$alkyl, $C_{3-6}$cycloalkyl, phenyl, —O-phenyl, or —N(H)C(O)O—$C_{1-4}$alkyl.

According to another embodiment of the first aspect of the present invention are provided compounds of Formula (I) according to the first embodiment of the first aspect wherein $R^1$ and $R^2$ are independently H, $C_{1-3}$alkyl, or —N(H)C(O)O—$C_{1-4}$alkyl.

According to another embodiment of the first aspect of the present invention are provided compounds of Formula (I) according to the first embodiment of the first aspect wherein $R^1$ and $R^2$ are independently H, $C_{1-3}$alkyl, $C_{3-6}$cycloalkyl, phenyl, or —O-phenyl.

According to another embodiment of the first aspect of the present invention are provided compounds of Formula (I) according to the first embodiment of the first aspect wherein $R^1$ and $R^2$ are independently H, $C_{1-3}$alkyl, or are independently selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl.

According to another embodiment of the first aspect of the present invention are provided compounds of Formula (I) according to the first embodiment of the first aspect wherein $R^2$ is H or $C_{1-3}$alkyl and $R^1$ is $C_{3-6}$cycloalkyl, phenyl, —O-phenyl, or —N(H)C(O)O—$C_{1-4}$alkyl.

According to another embodiment of the first aspect of the present invention are provided compounds of Formula (I) according to the first embodiment of the first aspect wherein $R^2$ is H or $C_{1-3}$alkyl and $R^1$ is N(H)C(O)O—$C_{1-4}$alkyl.

According to another embodiment of the first aspect of the present invention are provided compounds of Formula (I) according to the first embodiment of the first aspect wherein $R^2$ is H or $C_{1-3}$alkyl and $R^1$ is $C_{3-6}$cycloalkyl, phenyl or —O-phenyl.

According to another embodiment of the first aspect of the present invention are provided compounds of Formula (I) according to the first embodiment of the first aspect wherein $R^2$ is H or $C_{1-3}$alkyl and $R^1$ is selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl.

According to another embodiment of the first aspect of the present invention are provided compounds of Formula (I) according to the first embodiment of the first aspect wherein $R^1$ is H or $C_{1-3}$alkyl and $R^2$ is $C_{3-6}$cycloalkyl, phenyl, —O-phenyl, or —N(H)C(O)O—$C_{1-4}$alkyl.

According to another embodiment of the first aspect of the present invention are provided compounds of Formula (I) according to the first embodiment of the first aspect wherein $R^1$ is H or $C_{1-3}$alkyl and $R^2$ is N(H)C(O)O—$C_{1-4}$alkyl.

According to another embodiment of the first aspect of the present invention are provided compounds of Formula (I) according to the first embodiment of the first aspect wherein $R^1$ is H or $C_{1-3}$alkyl and $R^2$ is $C_{3-6}$cycloalkyl, phenyl or —O-phenyl.

According to another embodiment of the first aspect of the present invention are provided compounds of Formula (I) according to the first embodiment of the first aspect wherein $R^1$ is H or $C_{1-3}$alkyl and $R^2$ is selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl.

According to another embodiment of the first aspect of the present invention are provided compounds of Formula (I) according to the first embodiment of the first aspect wherein —$A^1$—$R^1$ and —$A^2$—$R^2$ together with the nitrogen to which they are attached form pyrrolidinyl, piperidinyl, piperazinyl, morpholino, adamantyl, tetrahydroquinolinyl or tetrahydroisoquinolinyl and are optionally substituted with benzyl.

According to another embodiment of the first aspect of the present invention are provided compounds of Formula (I) according to the first embodiment of the first aspect wherein $A^1$ and $A^2$ are each independently $C_{1-4}$alkylene or a bond;

$A^3$ is $C_{1-4}$alkylene;

$A^4$ is a bond and is attached to X or $X^1$;

$R^1$ and $R^2$ are independently H, $C_{1-3}$alkyl, $C_{3-6}$cycloalkyl, phenyl, —O-phenyl or —N(H)C(O)O—$C_{1-4}$alkyl;

said $C_{3-6}$cycloalkyl, phenyl or O-phenyl being independently and optionally substituted with $C_{1-4}$alkyl, $C_{1-3}$alkoxy or halo;

or are independently selected from the group of heterocyclic moieties consisting of thienyl, imidazolyl, pyridyl, piperidinyl, piperazinyl, morpholino, adamantyl, indolyl, tetrahydroquinolinyl and tetrahydroisoquinolinyl;

or wherein —$A^1$—$R^1$ and —$A^2$—$R^2$ together with the nitrogen to which they are attached form pyrrolidinyl, piperidinyl, piperazinyl, morpholino, adamantyl, tetrahydroquinolinyl or tetrahydroisoquinolinyl and are optionally substituted with benzyl;

$R^3$ is H or $C_{1-4}$alkyl;

m is 0 or 1;

$R^4$ is cyano or halo and is attached to X or $X^1$;

n is 0;

X and $X^1$ are each C;

$X^2$ and $X^3$ are each CH;

G is N, O or S;

$G^1$ is N or CH;

Y is (D)H wherein D is C; and

Z is (E)H wherein E is C;

provided that if G is O or S; then m is 0;

if G is N, then m is 1;

if $R^1$ is —N(H)C(O)O$C_{1-4}$alkyl or said heterocyclic moiety wherein said heterocyclic moiety contains a nitrogen atom and said nitrogen atom is attached to $A^1$, then $A^1$ is $C_{2-4}$alkylene;

if $R^2$ is —N(H)C(O)O$C_{1-4}$alkyl or said heterocyclic moiety wherein said heterocyclic moiety contains a nitrogen atom and said nitrogen atom is attached to $A^2$, then $A^2$ is $C_{2-4}$alkylene;

if $R^1$ is —N(H)C(O)O—$C_{1-4}$alkyl or said heterocyclic moiety, then $R^2$ is H or $C_{1-3}$alkyl;

if $R^2$ is —N(H)C(O)O—$C_{1-4}$alkyl or said heterocyclic moiety, then $R^1$ is H or $C_{1-3}$alkyl;

if $R^4$ is F and is attached to X and if $A^3$ is methylene, then —$A^1$—$R^1$ and —$A^2$—$R^2$ together with the nitrogen to which they are attached is not N-methylpiperazinyl; and if $R^4$ is F and is attached to X and if $A^3$ is methylene, then —$A^1$—$R^1$ and —$A^2$—$R^2$ together with the nitrogen to which they are attached is not tetrahydroquinolinyl.

According to another embodiment of the first aspect of the present invention are provided compounds of Formula (I) according to the first embodiment of the first aspect wherein said compounds exhibit greater SERT binding than $hD_{2L}$ binding as described herein.

According to another embodiment of the first aspect of the present invention are provided compounds of Formula (I) according to the first embodiment of the first aspect wherein said compounds exhibit less SERT binding than $hD_{2L}$ binding as described herein.

According to various embodiments of a second aspect of the present invention are provided pharmaceutically acceptable formulations comprising compounds of Formula (I) as defined herein.

The compounds of the present invention may be useful in the treatment or prevention of disorders in which the regulation of monoamide transporter function is implicated. Disease states that may be implicated include hypertension, depression (e.g., depression in cancer patients, depression in Parkinson's patients, postmyocardial infarction depression, subsyndromal symptomatic depression, depression in infertile women, paediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenobarbital, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, male impotence, attention deficit hyperactivity disorder (ADHD), chronic paroxysmal hemicrania, headache (associated with vascular disorders), emotional lability, pathological crying and sleeping disorder (cataplexy).

Disorders of particular interest include depression, attention deficit hyperactivity disorder, obsessive-compulsive disorder, post-traumatic stress disorder, substance abuse disorders and sexual dysfunction including (in particular) premature ejaculation. The compounds of the present invention may be administered alone or as part of a combination therapy.

Premature ejaculation may be defined as persistent or recurrent ejaculation before, upon or shortly after penile penetration of a sexual partner. It may also be defined as ejaculation occurring before the individual wishes [see *The Merck Manual*, $16^{th}$ edition, p. 1576, published by Merck Research Laboratories, 1992].

Thus according to various embodiments of a third aspect of the present invention are provided methods of treating conditions selected from the group consisting of depression, anxiety disorders, premature ejaculation, urinary incontinence, chronic pain, obsessive-compulsive disorder, feeding disorders, premenstrual dysphoric disorder, hot flashes, panic disorders, posttraumatic stress disorder and social phobia comprising the administration to a human in need thereof an effective amount of pharmaceutically acceptable formulations comprising compounds of Formula (I) as defined herein.

According to various embodiments of a fourth aspect of the present invention are provided methods of treating psychotic disorders including bipolar disorder and schizophrenia comprising the administration to a human in need thereof an effective amount of pharmaceutically acceptable formulations comprising compounds of Formula (I) exhibiting greater than or equal $hD_{2L}$ binding than SERT binding as defined herein.

According to various embodiments of a fifth aspect of the present invention are provided methods of enhancing the treatment of conditions selected from the group consisting of depression, anxiety disorders, premature ejaculation, urinary incontinence, chronic pain, obsessive-compulsive disorder, feeding disorders, premenstrual dysphoric disorder, panic disorders, posttraumatic stress disorder and social phobia comprising the administration to a human in need thereof an effective amount of pharmaceutically acceptable formulations comprising compounds of Formula (I) having SERT binding as defined herein and a pharmaceutically acceptable formulation of agents selected from the group consisting of (Lithium, 5-hydroxytryptophan, or a 5-HT1B/1D antagonist such as (R)-N-[5-methyl-8-(4-methylpiperazin-1-yl)-1,2,3,4-tetrahydronaphthalen-2-yl]-4-morpholino-benzamide.

According to a first embodiment of a sixth aspect of the present invention are provided methods of treating refractory depression comprising the administration to a human in need thereof an effective amount of a pharmaceutically acceptable formulation comprising compounds of Formula (I) as defined herein and a pharmaceutically acceptable formulation containing a reversible and selective MAO-A inhibitor.

According to another embodiment of the sixth aspect of the present invention are provided methods of treating refractory depression comprising the administration to a human in need thereof an effective amount of pharmaceutically acceptable formulations comprising compounds of Formula (I) as defined herein and a pharmaceutically acceptable formulation containng one or more reversible and selective MAO-A inhibitors selected from the group consisting of moclobemide, brofaromine and befloxatone.

According to another embodiment of the sixth aspect of the present invention are provided methods of treating refractory depression comprising the administration to a human in need thereof an effective amount of pharmaceutically acceptable formulation comprising compounds of Formula (I) as defined herein and a pharmaceutically acceptable formulation containing a 5-HT$_{1A}$ antagonist.

According to another embodiment of the sixth aspect of the present invention are provided methods of treating refractory depression comprising the administration to a human in need thereof an effective amount of pharmaceutically acceptable formulations comprising compounds of Formula (I) as defined herein and a pharmaceutically acceptable formulation containing a 5-HT$_{1A}$ antagonist selected from the group consisting of pindolol and WAY-100,635.

According to another embodiment of the sixth aspect of the present invention are provided methods of treating refractory depression comprising the administration to a human in need thereof an effective amount of pharmaceutically acceptable formulations comprising compounds of Formula (I) as defined herein and a pharmaceutically acceptable formulation containng a 5-HT$_{1B}$ antagonist.

According to another embodiment of the sixth aspect of the present invention are provided methods of treating refractory depression comprising the administration to a human in need thereof an effective amount of pharmaceutically acceptable formulations comprising compounds of Formula (I) as defined herein and a pharmaceutically acceptable formulation containing a partial 5-HT$_{1A/1B}$ antagonist.

According to another embodiment of the sixth aspect of the present invention are provided methods of treating refractory depression comprising the administration to a human in need thereof an effective amount of pharmaceutically acceptable formulations comprising compounds of Formula (I) as defined herein and a pharmaceutically acceptable formulation containing buspirone.

According to another embodiment of the sixth aspect of the present invention are provided methods of treating refractory depression comprising the administration to a human in need thereof an effective amount of pharmaceutically acceptable formulations comprising compounds of Formula (I) as defined herein and a pharmaceutically acceptable formulation containing methylphenidate.

According to a seventh aspect of the present invention are provided methods of treating obsessive compulsive disorder comprising the administration to an adolescent or child in need thereof an effective amount of pharmaceutically acceptable formulations comprising compounds of Formula (I) as defined herein and a pharmaceutically acceptable formulation containng clomipramine.

According to a first embodiment of an eighth aspect of the present invention are provided methods of treating refractory psychotic depression comprising the administration to a human in need thereof an effective amount of pharmaceutically acceptable formulations comprising compounds of Formula (I) as defined herein and a pharmaceutically acceptable formulation of an antipsychotic agent.

According to another embodiment of the eighth aspect of the present invention are provided methods of treating refractory psychotic depression comprising the administration to a human in need thereof an effective amount of pharmaceutically acceptable formulations comprising compounds of Formula (I) as defined herein and a pharmaceutically acceptable formulation of an antipsychotic agent selected from the group consisting of aripiprazole, olanzapine, risperdal, clozapine, ziprasidone, haldol, thiothixene and quetiapine fumarate.

According to a ninth aspect of the present invention are provided methods of treating exogenous obesity comprising the administration to a human in need thereof an effective amount of pharmaceutically acceptable formulations comprising compounds of Formula (I) as defined herein and a pharmaceutically acceptable formulation of phentermine.

According to a first embodiment of a tenth aspect of the present invention are provided methods of treating disorders or conditions which can be facilitated by altering circadian rhythms comprising the administration to a human in need thereof an effective amount of pharmaceutically acceptable formulations comprising compounds of Formula (I) as defined herein and a pharmaceutically acceptable formulation of a nitric oxide sythase inhibitor.

According to another embodiment of the tenth aspect of the present invention are provided methods of treating disorders or conditions which can be facilitated by altering circadian rhythms comprising the administration to a human in need thereof an effective amount of pharmaceutically acceptable formulations comprising compounds of Formula (I) as defined herein and a pharmaceutically acceptable formulation of a selective neuronal nitric oxide sythase inhibitor.

According to another embodiment of the tenth aspect of the present invention are provided methods of treating disorders or conditions which can be facilitated by altering circadian rhythms comprising the administration to a human in need thereof an effective amount of pharmaceutically acceptable formulations comprising compounds of Formula (I) as defined herein and a pharmaceutically acceptable formulation of a nitric oxide sythase inhibitor said conditions selected from the group consisting of blindness, obesity, seasonal affective disorder, bipolar disorder, jet lag, circadian sleep rhythms disorder, sleep deprivation, parasomnias, REM sleep disorders, hypersomnia, sleep-wake cycle disorders, narcolepsy and sleep disorders associated with shift work or irregular work schedules, nocturnal enuresis and restless-legs syndrome.

According to another embodiment of the tenth aspect of the present invention are provided methods of treating disorders or conditions which can be facilitated by altering circadian rhythms comprising the administration to a human in need thereof an effective amount of pharmaceutically acceptable formulations comprising compounds of Formula (I) as defined herein and a pharmaceutically acceptable formulation of a selective neuronal nitric oxide sythase inhibitor said conditions selected from the group consisting of blindness, obesity, seasonal affective disorder, bipolar disorder, jet lag, circadian sleep rhythms disorder, sleep deprivation, parasomnias, REM sleep disorders, hypersomnia, sleep-wake cycle disorders, narcolepsy and sleep disorders associated with shift work or irregular work schedules, nocturnal enuresis and restless-legs syndrome.

According to a first embodiment of an eleventh aspect of the present invention is provided a process for the preparation of a compound of Formula (d)

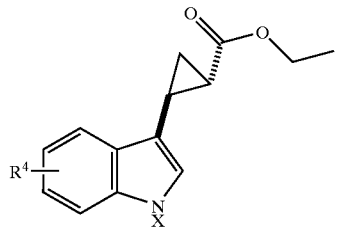
(d)

by reacting a compound of formula (b)

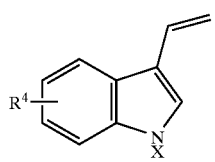
(b)

with a compound of formula (c)

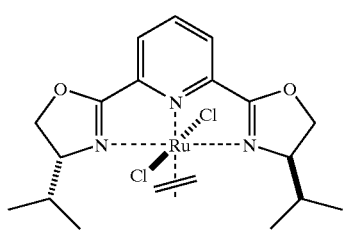
(c)

in the presence of ethyl diazoacetate and toluene, wherein $R^4$ is cyano, halo, nitro or $C_{1-3}$perfluoroalkyl and X is p-toluenesulfonyl, benzenesulfonyl, methansulfonyl or trifluoromethanesulfonyl.

According to another embodiment of the eleventh aspect of the present invention is provided a process for the preparation of a compound of Formula (d¹)

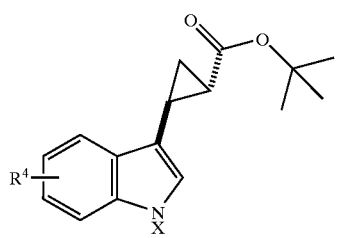
(d')

by reacting a compound of formula (b)

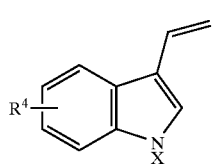
(b)

with a compound of formula (c)

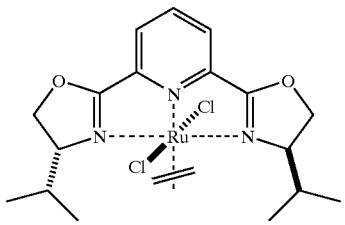
(c)

in the presence of tert-butyl diazoacetate and toluene, wherein $R^4$ is cyano, halo, nitro or $C_{1-3}$perfluoroalkyl and X is p-toluenesulfonyl, benzenesulfonyl, methansulfonyl or trifluoromethanesulfonyl.

According to a twelvth aspect of the present invention is provided a method of treating sexual dysfunction in a mammal in need thereof comprising the administration of a pharmaceutically acceptable salt or solvate of a compound of Formula (I) and a compound selected from the group of known erectile dysfunction agents including sildenafil.

Other embodiments of the present invention may comprise suitable combinations of two or more of the embodiments and/or aspects disclosed herein.

Yet other embodiments and aspects of the invention will be apparent according to the description provided below.

DETAILED DESCRIPTION OF THE INVENTION

The description of the invention herein should be construed in congruity with the laws and principals of chemical bonding. For example, it may be necessary to remove a hydrogen atom in order accommodate a substitutent at any given location.

An embodiment or aspect which depends from another embodiment or aspect, will describe only the variables having values or provisos that differ from the embodiment or aspect from which it depends.

If a variable is quantified with a value of zero, then any bond attaching said variable should no longer be represented, e.g., if n in $(R^3)_n$ equals 0, then the bond attaching $R^3$ to G should no longer be represented.

As used herein, "halo" or "halogen" includes fluoro, chloro, bromo and iodo.

As used herein, "$C_{1-4}$alkylene" means a one to four carbon alkane having one hydrogen atom removed from two different carbon atoms in said alkane, e.g., —$CH_2CH_2CH_2$—.

As used herein, "$C_{1-4}$alkylidene" means a one to four carbon alkane having two hydrogen atoms removed from one carbon atom in said alkane, e.g.,

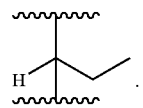

It should be understood that the alternating double bond designations in the six-membered ring of the 5,6-membered fused structure represented in Formula (I) are relative and represent the delocalized π orbital electrons of said ring.

It is to be understood that the present invention may include any and all possible stereoisomers, geometric isomers, diastereoisomers, enantiomers, anomers and optical isomers, unless a particular description specifies otherwise.

The compounds of this invention may exist in the form of pharmaceutically acceptable salts. Such salts may include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group may exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. In the case of a sublingual formulation a saccharin salt or maleate salt may be of particular benefit. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

The dosage and dosage regimen and scheduling of a compounds of the present invention must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level which will produce effective beneficial effects without causing any harmful or untoward side effects.

Synthesis

Compounds of the present invention may be synthesized according to the general schema provided below. Variables provided in the schema below are defined in accordance with the description of compounds of the above Formulae unless otherwise specified.

A preferred method for the preparation of trans-cyclopropanes of Formula I is illustrated in Scheme 1. A appropriately substituted heterocyclic aldehyde, where Pg is a protecting group such as p-toluenesulfonyl when G is nitrogen, is reacted with a appropriated olefinating reagent, such as a Horner-Emmons reagent. The resulting heterocyclic trans-acrylic acid derivative, preferably the N-methoxy-N-methyl amide, is cyclopropanated using reagents such as diazomethane and palladium(II)acetate, or trimethylsulfoxonium iodide with an appropriate base. The resulting cyclopropyl amide derivative is reduced to the aldehyde using reagents such as LAH, or the like. Subsequent reductive amination using an appropriately substituted amine with an reducing agent such as sodium triacetoxyborohydride, sodium cyanoborohydride, or the like, gives the cyclopropyl methyl amine. Removal of protecting groups, such as the p-toluenesulfonyl group, when G is nitrogen, using mild basic hydrolysis, gives the trans-cyclopropyl compounds of Formula 1.

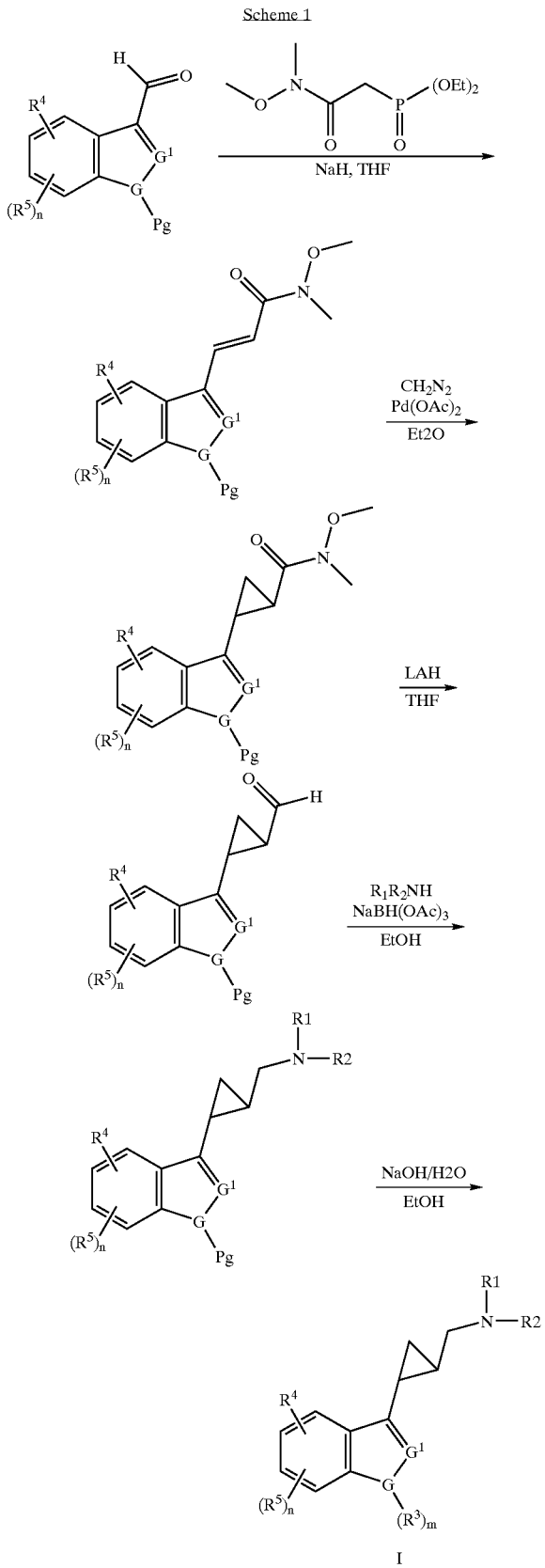

A preferred method of preparing cis-cyclopropyl compounds of Formula I is described in Scheme 2. This method is similar to that in Scheme 1, except for the use of olefinating reagents, such as the trifluoroethyl Horner-Emmons reagent, that selectively give the heterocyclic cis-acrylic acid derivatives, where Pg is a protecting group such as p-toluenesulfonyl when G is nitrogen. Further reaction of the cis-acrylic acid derivatives, in a manner similar to that described in Scheme 1, provides the cis-cyclopropyl compounds of Formula I.

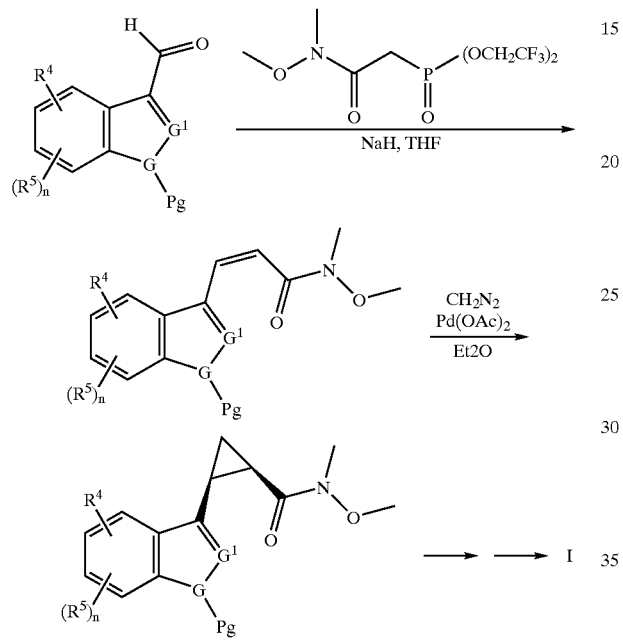

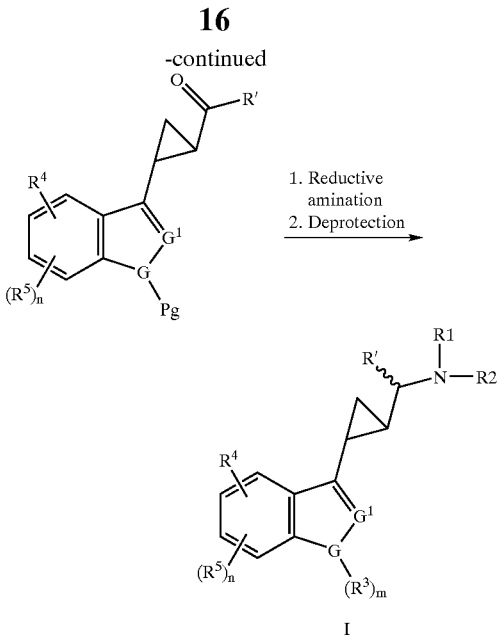

A preferred method for the preparation of compounds of Formula I where $A^3$ is a branched alkylidene chain is illustrated in Scheme 3. The N-methoxy-N-methyl-cyclopropyl carboxamide intermediate, where Pg is a protecting group such as p-toluenesulfonyl when G is nitrogen, is reacted with a nucleophile, such as a alkyl magnesium halide or alkyl lithium. The resulting cyclopropyl alkyl ketone is reductively aminated and subsequently deprotected in a manner similar to that described in Scheme 1 to give compounds of Formula I where $A^3$ is a branched alkylidene chain.

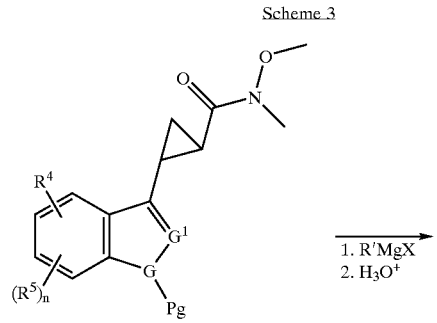

Another preferred method for the preparation of compounds of Formula I is illustrated in Scheme 4. An appropriately substituted vinyl heterocycle, where Pg is a protecting group such as p-toluenesulfonyl when G is nitrogen, is reacted with an appropriate diazoacetate ester, such as ethyl or tert-butyl diazoacetate, in the presence of a catalyst such as the Nishiyama catalyst. [(R)-trans-Cl$_2$Ru(pybox-ip)(CH$_2$=CH$_2$) was prepared from 2,6-bis(4R)-(+)-isopropyl-2-oxazolin-2-yl]pyridine (Aldrich Chemical Co.) according to: Nishiyama, H.; Itoh, Y.; Matsumoto, H.; Park, S. -B.; Itoh, K. *J. Am. Chem Soc.* 1994, 116, 2223.] The resulting cyclopropyl ester is reduced to the alcohol using reagents such as DIBAL, LAH, or the like. The resulting alcohol is then oxidized to the corresponding aldehyde using standard methods, such as PCC or DMSO/oxalyl chloride. The resulting aldehyde is then converted to the compounds of Formula 1 by the methods outlined in Scheme 1.

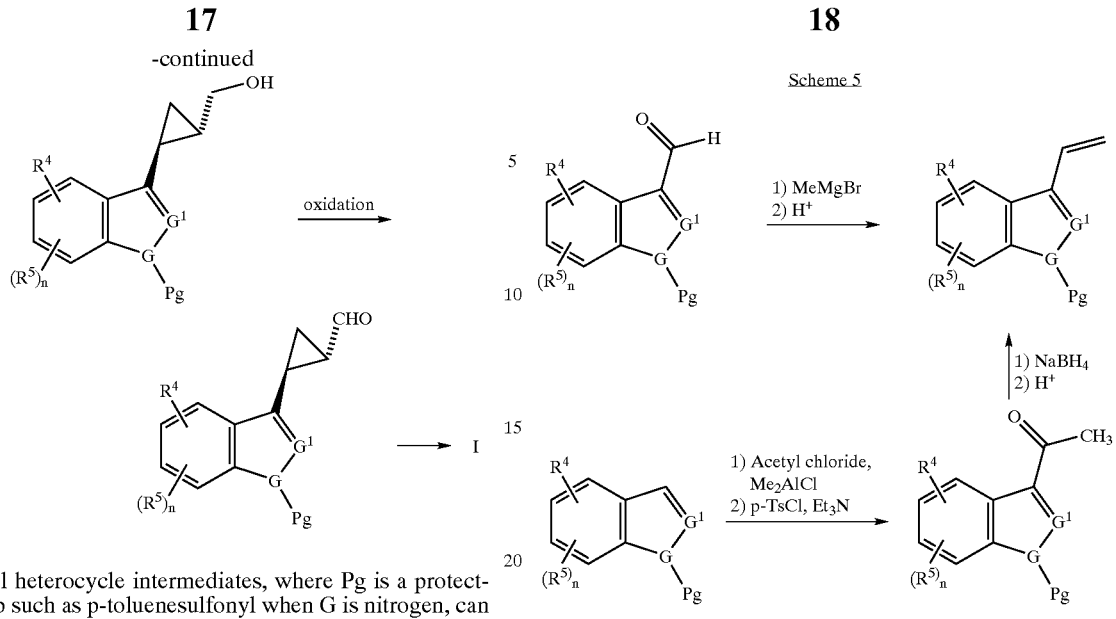

The vinyl heterocycle intermediates, where Pg is a protecting group such as p-toluenesulfonyl when G is nitrogen, can be prepared in several ways (Scheme 5). Treatment of an appropriate aldehyde with an organometalic reagent such a methyl magnesium bromide, or the like, with subsequent dehydration of the resulting alcohol using reagents such as p-toluene sulfonic acid, or the like, is one preferred method for the preparation of the vinyl heterocycle intermediates. Another preferred method consists of acetylation of the heterocycle using reagents such as acetyl chloride and diethylaluminum chloride, or the like, followed by the optional protection of the heterocycle using p-toluenesulfonyl chloride and triethyl amine, or the like. Reduction of the acetyl group using sodium borohydide, or the like, with subsequent dehydration of the resulting alcohol gives the vinyl heterocycle.

The preparation of indazole compounds of Formula 1 is described in Scheme 6. The aryl cyclopropyl ketone intermediate is prepared my methods known to those skilled in the art, such as a palladium mediated coupling of an aryl boronate with a cyclopropane thioester. This ketone intermediate is reacted with an appropriately substituted hydrazine, such as p-toluenesulfonylhydrazide, and subsequently cyclized to an indazole under mild basic conditions, such as potassium carbonate. The resulting cyclopropyl ester is converted to compounds of Formula 1 by methods similar to those described in Scheme 3.

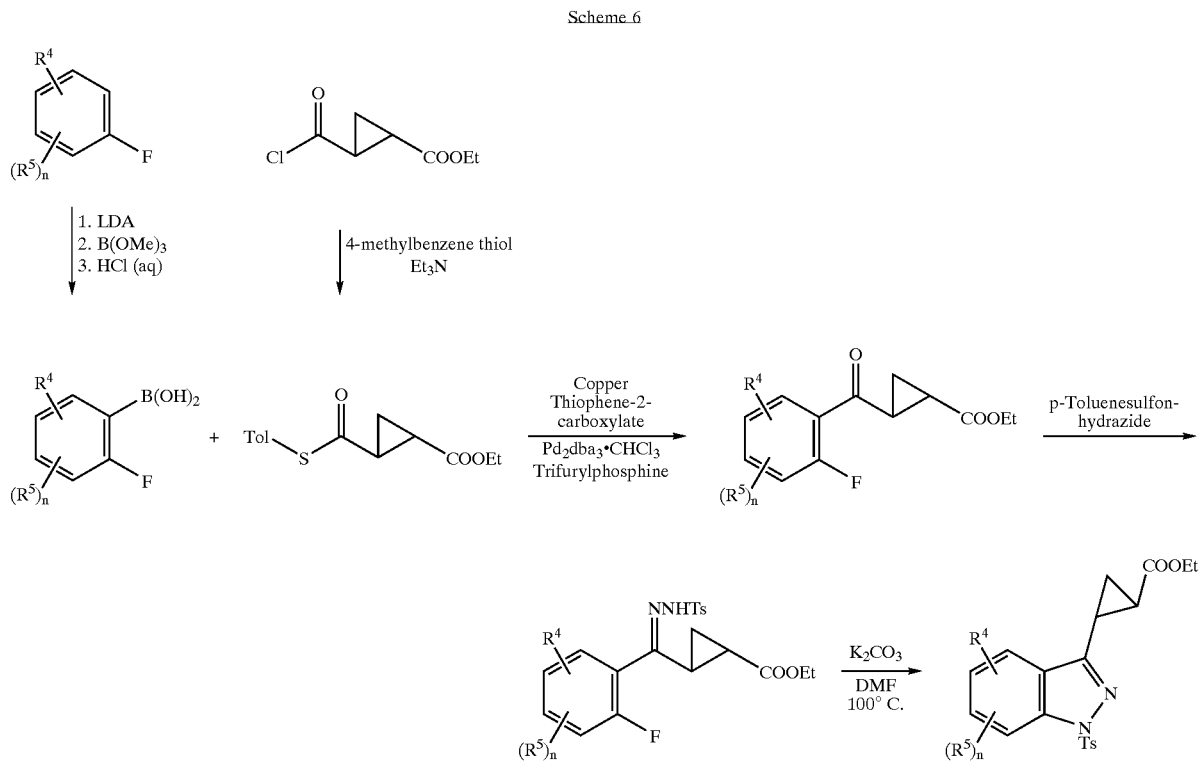

The preparation of compounds of Formula 1, where G is sulfur, is described in Scheme 7. The appropriately substituted carboxaldehyde is carried through a reaction sequence in a manner similar to that described in Scheme 1 to give the compounds of Formula I, where G is sulfur.

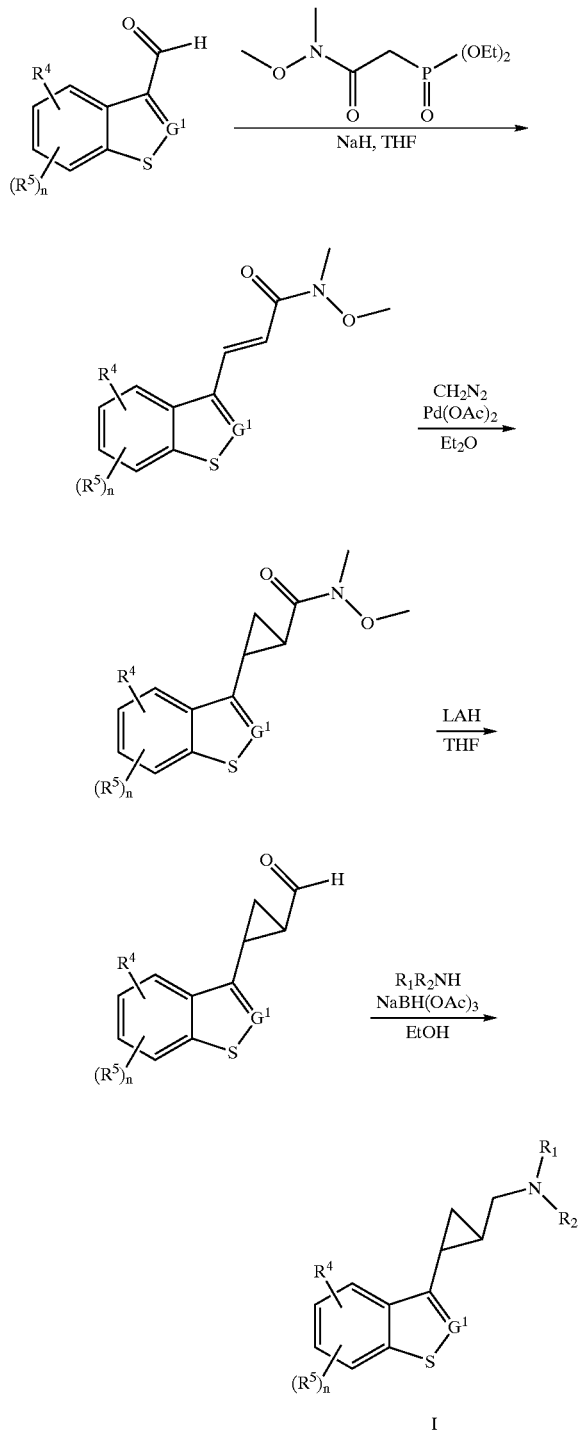

The preparation of indole and indazole compounds of Formula 1, where $R^3$ is lower alkyl, is described in Scheme 8, along with the preparation quaternary alkyl ammonium salts of compounds of Formula 1. Indole and indazole compounds of Formula 1, where $R^3$ is H, are reacted with bases such as sodium hydride or potassium tert-butoxide in the presence of alkylating reagents, such as dimethyl sulfate or diethyl sulfate, to give derivatives where where $R^3$ is lower alkyl. Quaternary alkyl ammonium salts of compounds of Formula 1, are prepared by reaction of tertiary amine compounds of Formula 1 with alkyl halides, such as methyl iodide.

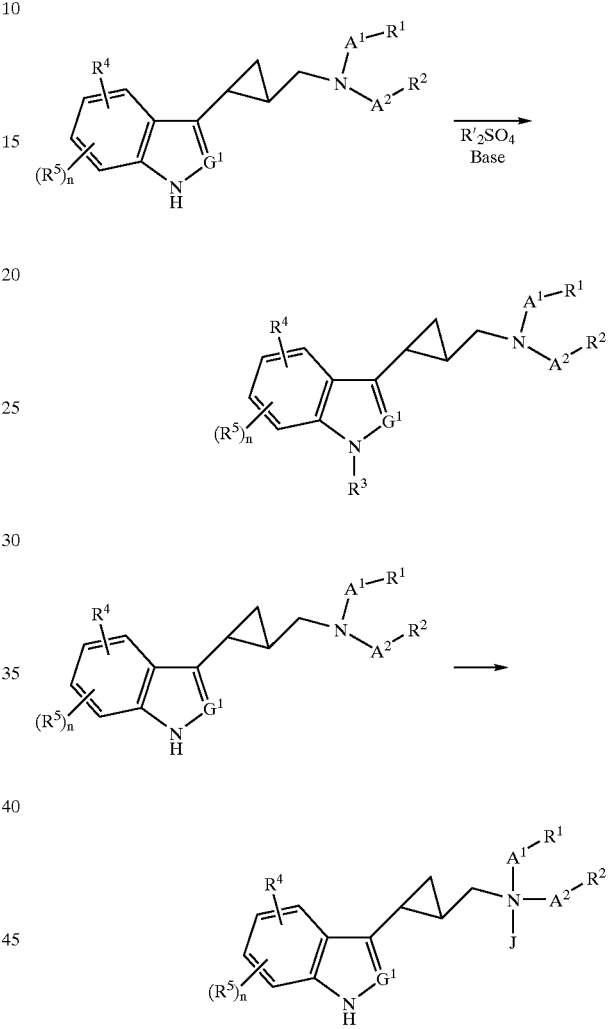

Another preferred method for preparing compounds of Formula 1, where $A^4$ is attached at points X, $X^1$, or $X^2$, is described in Scheme 9. An appropriately substituted heterocycle, with a reacting group Rg (such as iodo, bromo, or trifluoromethanesulfonyl groups) is present at points X or $X^2$ is reacted with an appropriately substituted acryamide under catalysis with palladium(II)acetate, or the like. The resulting substituted acrylamide derivative is converted to compounds of Formula I by methods similar to those described in Scheme 1. The substituted acrylamide derivative can also be prepared from appropriately substituted heterocyclic aldehyde, where the aldehyde is attached at points X, $X^1$, or $X^2$. Olefination of the aldehyde with the Horner-Emmons reagent under conditions described in Scheme 1 also gives the substituted acrylamide derivative which can be converted to compounds of Formula I by methods similar to those described in Scheme 1.

Scheme 9

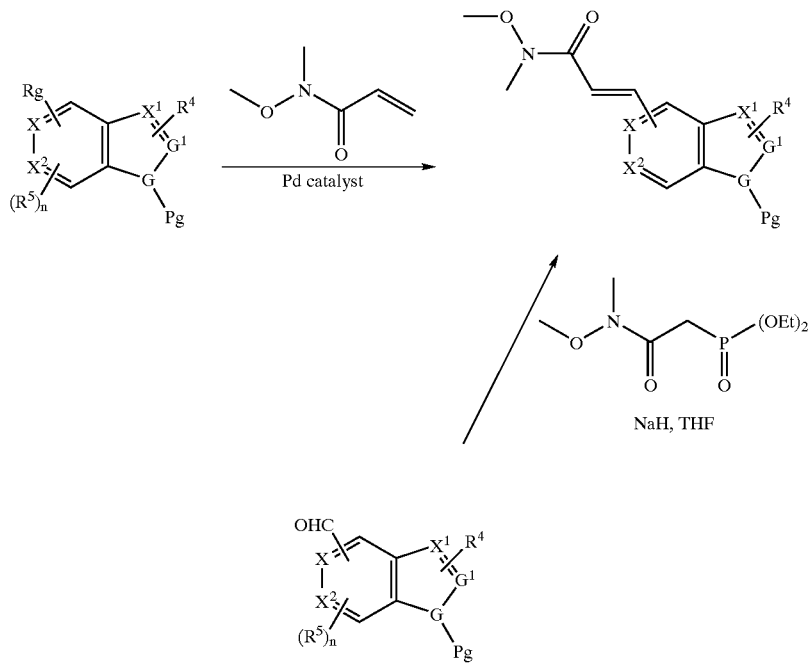

Other suitable means of synthesizing said compounds may also be available. More detailed descriptions of synthesizing compounds of the present invention are also provided. The required starting materials and reagents, such as substituted indoles and indolecarboxaldehydes, for these methods can be obtained from commercial sources. Other starting materials that are not commercially available can be prepared by standard methods known to those skilled in the art.

EXAMPLE 1

Trans-2-[5-Cyanoindol-3-yl]-1-(N,N-dimethylaminomethyl)cyclopropane

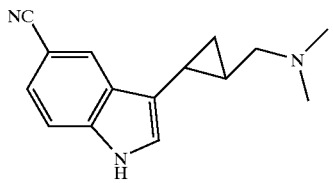

Phosphorus oxychloride (10.9 ml, 117 mmol) was added dropwise over 30 min to anhydrous dimethylformamide (50 ml) that was maintained at 10–20° C. (internal temperature). The resulting mixture was stirred for 30 min and then chilled to 0° C. A solution of commercially available 5-cyanoindole (15 g, 106 mmol) in anhydrous dimethylformamide (30 ml) was added over 10 min. The ice bath was removed and the solution was allowed to warm to room temperature. After 2 h, a very thick paste resulted. The off-white paste was carefully quenched with ice chips. An aqueous solution of sodium hydroxide (2.12 g NaOH/100 ml $H_2O$) was added. After a mild exotherm, a clear yellow solution resulted. The solution was poured into water (~400 ml) and a fine solid immediately precipitated. The mixture was filtered through a 600 ml glass fritted funnel of medium porosity. The yellow filtrate was diluted with an equal volume of water and left to stand for 16 h. A yellow precipitate was collected by vacuum filtration. The solid was dried overnight under vacuum to afford 13.6 g (75% yield) of (5-cyanoindol-3-yl)carboxaldehyde: $^1$H NMR (500 MHz, DMSO-$d_6$) 12.58 (1H, br s,), 10.00 (1H, s), 8.51 (1H, d, J=3.1 Hz), 8.46 (1H, d, J=0.6 Hz), 7.22 (1H, dd, J=8.6, 0.5 Hz), 7.64 (1H, dd, J=8.5, 1.6 Hz); MS m/e 171 (M+H)$^+$.

p-Toluenesulfonyl chloride (15.2 g, 79.5 mmol) was added to a solution of (5-cyanoindol-3-yl)carboxaldehyde (13.5 g, 79.5 mmol) and triethylamine (12.2 ml, 87.5 mmol) in anhydrous dichloromethane (250 ml). The mixture was left to stir for 24 h at room temperature. The solid precipitate was collected using a Buchner funnel and washed with ethanol. The white solid was dried under vacuum to afford 16.85 g (65% yield) of [5-cyano-1-(p-toluenesulfonyl)indol-3-yl]carboxaldehyde: mp 243° C. (dec.); $^1$H NMR (400 MHz, DMSO-$d_6$) 10.09 (1H, s), 9.07 (1H, s), 8.49 (1H, d, J=1.1 Hz), 8.16 (1H, dd, J=8.6, 0.3 Hz), 8.06 (2H, d, J=8.5 Hz), 7.87 (1H, dd, J=8.7, 1.7), 7.48 (2H, d, J=8.1 Hz), 2.36 (3H, s); MS m/e 325 (M+H)$^+$. Anal. calcd. for $C_{17}H_{12}N_2O_3S$: C, 62.95; H, 3.72; N, 8.63. Found: C, 62.94; H, 3.68; N, 8.62.

A solution of diethyl (N-methoxy-N-methylcarbamoylmethyl) phosphonate (12.81 ml, 14.85 g, 62.1 mmol) in anhydrous tetrahydrofuran (50 ml) was added to a stirred suspension of oil free sodium hydride (1.49 g, 62.1 mmol) in anhydrous tetrahydrofuran (900 ml) maintained at 0° C. The reaction was warmed to room temperature and was stirred for 2 h. After cooling to 0° C., [5-cyano-1-(p-toluenesulfonyl)indol-3-yl]carboxaldehyde (16.8 g, 51.8 mmol) was added. The resulting mixture was stirred at 0° C. for 1 hr. The reaction was quenched with aqueous hydrochloric acid (0.1 N) and poured into water (250 ml). After being made acidic with hydrochloric acid (1.0 N), the aqueous portion was extracted with ethyl acetate (3×150 ml). The combined organic layers were washed with brine (50 ml) and dried over anhydrous magnesium sulfate. The filtrate was concentrated in vacuo. The crude product was purified by recrystallization from ethyl acetate to afford a total of 19.1 g (12.5 g first crop, 6.58 g second crop, 91% yield) of (E)-[5-Cyano-1-(p-toluenesulfonyl)indol-3-yl]-N-methoxy-N-methyl-acrylamide as a white solid: mp 177–178° C.; $^1$H NMR (500 MHz, DMSO-$d_6$) 8.70 (1H, s), 8.47 (1H, s), 8.14 (1H, d, J=8.7 Hz), 7.98 (2H, d, J=8.4 Hz), 7.81 (1H, dd, J=8.7, 1.4 Hz), 7.72 (1H, d, J=16.0 Hz), 7.44 (2H, d, J=8.2 Hz), 7.21 (1H, d, J=16.0 Hz), 3.77 (3H, s), 3.24 (3H, s), 2.34 (3H, s); MS m/e 410 (M+H)$^+$. Anal. calcd. for $C_{21}H_{19}N_3O_4S$: C, 61.60; H, 4.67; N, 10.26. Found: C, 61.57; H, 4.64; N, 10.15.

The following procedure was carried out behind a safety shield using plastic coated glassware free of scratches and ground glass joints. 1-Methyl-3-nitro-1-nitrosoguanidine (14.4 g, 98 mmol) was carefully added portionwise over 30 min to a Erlenmeyer flask containing a swirled mixture of aqueous sodium hydroxide (100 ml, 5 N) and diethyl ether (250 ml) at 0° C. After vigorous bubbling had ceased, the organic layer (containing diazomethane) was decanted into a chilled (0° C.) Erlenmeyer flask containing potassium hydroxide chips (20 g). The mixture was swirled for 10 min and the yellow solution was decanted into a dropping funnel. The solution of diazomethane was added over 30 min to an open flask containing a stirred mixture of (E)-[5-Cyano-1-(p-toluenesulfonyl)indol-3-yl]-N-methoxy-N-methylacrylamide (8.0 g, 19.6 mmol) and palladium acetate (132 mg, 0.58 mmol) in dichloromethane (200 ml) maintained at 0° C. After stirring for 1 h, a second batch of freshly prepared diazomethane (98 mmol) in ~250 ml of diethyl ether was added over 30 min. After stirring for 1 h, the reaction was quenched with glacial acetic acid (4 ml) and poured into an aqueous saturated solution of sodium bicarbonate (250 ml). The aqueous layer was extracted with ethyl acetate (3×100 ml). The organic layers were washed with brine, dried over anhydrous magnesium sulfate, and concentrated in vacuo. The crude product was triturated with ethyl acetate (150 ml) and cooled with vigorous stirring to 0° C. for 1 h. The product was collected by vacuum filtration, and rinsed with cold ethyl acetate (25 ml). The white solid was dried under vacuum to afford 4.46 g (54% yield) of [trans-2-[5-Cyano-1-(p-toluenesulfonyl)indol-3-yl]cycloprop-1-yl]-N-methoxy-N-methylcarboxamide. An analytical sample was obtained by recrystallization from ethyl acetate/hexane: mp 174–175° C.; $^1$H NMR (400 MHz, DMSO-$d_6$) 8.23 (1H, d, J=1.1 Hz), 8.07 (1H, d, J=8.6 Hz), 7.91 (2H, d, J=8.4 Hz), 7.86 (1H, s), 7.75 (1H, dd, J=8.6, 1.5 Hz), 7.40 (2H, d, J=8.2 Hz), 3.64 (3H, s), 3.16 (3H, s), 2.43 (2H, m), 2.33 (3H, s), 1.43 (2H, m); MS m/e 424 (M+H)$^+$. Anal. calcd. for $C_{22}H_{21}N_3O_4S$: C, 62.39; H, 4.99; N, 9.92. Found: C, 62.33; H, 5.02; N, 9.80.

Powdered lithium aluminum hydride (1.79 g, 47.3 mmol) was carefully added portionwise to a stirred solution of [trans-(1R,2R)-2-[5-cyano-1-(p-toluenesulfonyl)indol-3-yl]cycloprop-1-yl]-N-methoxy-N-methylcarboxamide (4.0 g, 9.45 mmol) in anhydrous tetrahydrofuran (250 ml) at −40° C. The resulting mixture was stirred at −40° C. for 2 h. The reaction was quenched with ethyl acetate (25 ml) and allowed to warmed to room temperature. After 30 min, water (1.79 ml) was added followed by a solution of aqueous sodium hydroxide (15% w/v, 3.58 ml). After stirring for 30 min at room temperature the aluminum salts were removed by vacuum filtration. The salts were rinsed with ethyl acetate (100 ml) and the combined filtrates were concentrated in vacuo. The crude material was purified by silica gel column chromatography (hexane/ethyl acetate, 4:1, 3:1) to afford 2.86 g (74% yield) of trans-2-[5-Cyano-1-(p-toluenesulfonyl)indol-3-yl]cyclopropanecarboxaldehyde as a white solid. An analytical sample was obtained by recrystallization from ethyl acetate/hexane: mp 165–167° C.; $^1$H NMR (400 MHz, DMSO-$d_6$) 9.08 (1H, d, J=5.5 Hz), 8.32 (1H, d, J=1.1 Hz), 8.06 (1H, d, J=8.6 Hz), 7.90 (2H, d, J=8.6 Hz), 7.89 (1H, s), 7.75 (1H, dd, J=8.6, 1.5 Hz), 7.40 (2H, d, J=8.2 Hz), 2.77 (1H, m), 2.33 (3H, s), 2.13 (1H, m), 1.74 (2H, m); MS m/e 363 (M−H)$^−$. Anal. calcd. for $C_{20}H_{16}N_2O_3S$: C, 65.91; H, 4.42; N, 7.68. Found: C, 65.90; H, 4.30; N, 7.38.

A mixture of trans-2-[5-Cyano-1-(p-toluenesulfonyl)indol-3-yl]cyclopropanecarboxaldehyde (2.0 g, 5.49 mmol), dimethylamine (8.2 ml, 16.5 mmol, 2.0 M/THF), and anhydrous ethanol (70 ml) were heated to 80° C. with stirring until all solids were dissolved (20 min). The reaction vessel was removed from the heating source and sodium triacetoxyborohydride was added. After stirring for 30 min, the reaction vessel was placed in an ice-bath and quenched with aqueous hydrochloric acid (40 ml, 1 N). The resulting mixture was stirred for 20 min and then poured into a saturated aqueous solution of sodium bicarbonate (100 ml) and brine (50 ml). The aqueous layer was extracted with ethyl acetate (3×100 ml). The combined organic extracts were washed with brine (20 ml), dried over anhydrous magnesium sulfate, filtered, and concentrated in vacuo. The solid residue was dried under vacuum for 24 h and the crude product subjected directly to reaction conditions used for cleavage of the N-tosyl group. A sample of trans-2-[5-cyano-1-(p-toluenesulfonyl)indol-3-yl]-1-(N,N-dimethylaminomethyl)cyclopropane was purified by silica gel column chromatography for analytical purposes: $^1$H NMR (400 MHz, DMSO-$d_6$) 8.24 (1H, d, J=1.0 Hz), 8.06 (1H, d, J=8.6 Hz), 7.89 (2H, d, J=8.4 Hz), 7.74 (1H, dd, J=8.6, 1.6 Hz), 7.67 (1H, s), 7.39 (2H, d, J=8.1 Hz), 2.32 (5H, m), 2.21 (6H, s), 1.83 (1H, m), 1.21 (1H, m), 1.07 (1H, m), 0.80 (1H, m); MS m/e 394 (M+H)$^+$.

Water (5 ml) and an aqueous solution of sodium hydroxide (2 ml, 10 N) were sequentially added to a flask charged with a solution of crude trans-2-[5-cyano-1-(p-toluenesulfonyl)indol-3-yl]-1-(N,N-dimethylaminomethyl)cyclo propane dissolved in anhydrous ethanol (60 ml). The resulting mixture was heated at 70° C. for 45 min. After cooling to room temperature, the reaction was quenched with aqueous hydrochloric acid (21 ml, 1 N) and then poured into a mixture of saturated aqueous sodium bicarbonate (100 ml) and brine (50 ml). The aqueous layer was extracted with 10% methanol/ethyl acetate (4×100 ml). The combined organic layers were washed with brine (25 ml), dried over anhydrous magnesium sulfate, filtered, and concentrated in vacuo. The crude material was purified by silica gel column chromatography using silica gel pretreated with 2% triethylamine in chloroform/methanol (9:1). The column was eluted using a step gradient of a ternary solvent mixture [chloroform/methanol/(2 M ammonia/methanol), 90/10/0, 85/15/1, 80/20/1, 80/20/2]. The product was obtained as an off-white solid foam (1.2 g, 98% yield) after drying under vacuum. Recrystallization from ethanol/water provided a total of 934 mg (583 mg first crop, 351 mg second crop, 77% yield) of trans-2-[5-cyanoindol-3-yl]-1-(N,N-dimethylaminomethyl)cyclopropane: mp 120–121° C.; $^1$H NMR (400 MHz, DMSO-$d_6$) 11.34 (1H, br s), 8.09 (1H, s), 7.47 (1H, d, J=8.4 Hz), 7.40 (1H, dd, J=8.4, 1.5 Hz), 7.23 (1H, d, J=2.0 Hz), 2.37 (2H, m), 2.21 (6H, s), 1.80 (1H, m), 1.09 (1H, m), 0.91 (1H, m), 0.73 (1H, m); MS m/e 240 (M+H)$^+$. Anal. calcd. for $C_{15}H_{17}N_3$: C, 75.28; H, 7.16; N, 17.55. Found: C, 75.05; H, 7.04; N, 17.60.

EXAMPLE 2

Trans-1-(N,N-dimethylaminomethyl)-2-[5-fluoroindol-3-yl]cyclopropane

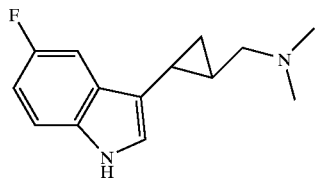

p-Toluenesulfonyl chloride (11.7 g, 61.3 mmol) was added to a solution of commercially available (5-fluoroindol-3-yl)carboxaldehyde (10.0 g, 61.3 mmol) and triethylamine (9.40 ml, 67.4 mmol) in anhydrous dichloromethane (250 ml). The mixture was left to stir for 6 h at room temperature. The solid precipitate was collected using a Buchner funnel and washed with ethanol. The white solid was dried under vacuum to afford 14.6 g (75% yield) of [5-fluoro-1-(p-toluenesulfonyl)indol-3-yl]carboxaldehyde: mp 225–226° C. (dec.); $^1$H NMR (400 MHz, DMSO-$d_6$) 10.05 (1H, s), 8.95 (1H, s), 8.00 (3H, m), 7.80 (1H, dd, J=8.8 Hz, 2.6 Hz), 7.46 (2H, d, J=8.1 Hz), 7.33 (1H, t, J=9.2 Hz), 2.35 (3H, s); MS m/e 318 (M+H)$^+$. Anal. Calcd. For $C_{16}H_{12}FNO_3S$: C, 60.55; H, 3.81; N 4.41. Found: C, 60.28; H, 3.78; N, 4.24.

A solution of diethyl (N-methoxy-N-methylcarbamoylmethyl) phosphonate (5.64 ml, 6.54 g, 27.4 mmol) in anhydrous tetrahydrofuran (25 ml) was added to a stirred suspension of oil free sodium hydride (1.05 g, 27.4 mmol) in anhydrous tetrahydrofuran (350 ml) maintained at 0° C. The reaction was warmed to room temperature and was stirred for 2 h. After cooling to 0° C., [5-fluoro-1-(p-toluenesulfonyl)indol-3-yl]carboxaldehyde (7.24 g, 22.8 mmol) was added. The resulting mixture was stirred at 0° C. for 30 min. The reaction was quenched with aqueous hydrochloric acid (0.1 N) and poured into water (150 ml). After being made acidic with hydrochloric acid (1.0 N), the aqueous portion was extracted with ethyl acetate (3×100 ml). The combined organic layers were washed with brine (50 ml) and dried over anhydrous sodium sulfate. The filtrate was concentrated in vacuo. The crude product was purified by recrystallization from ethyl acetate to afford a total of 8.03 g (88% yield) of (E)-[5-fluoro-1-(p-toluenesulfonyl)indol-3-yl]-N-methoxy-N-methylacrylamide as a white solid: mp 199–200° C. (dec.); $^1$H NMR (400 MHz, DMSO-$d_6$) 8.56 (1H, s), 7.99 (1H, m), 7.93 (2H, d, J=8.4 Hz), 7.68 (2H, m), 7.42 (2H, d, J=8.1 Hz), 7.28 (1H, t, J=9.2 Hz), 7.12 (1H, d, J=16 Hz), 3.77 (3H, s), 3.22 (3H, s), 2.33 (3H, s); MS m/e 403 (M+H)$^+$. Anal. Calcd. For $C_{20}H_{19}FN_2O_4S$: C, 59.69; H, 4.75; N, 6.96. Found: C, 59.60; H, 4.70; N, 6.86.

The following procedure was carried out behind a safety shield using plastic coated glassware free of scratches and ground glass joints. 1-Methyl-3-nitro-1-nitrosoguanidine (29.2 g, 199 mmol) was carefully added portionwise over 30 min to an Erlenmeyer flask containing a swirled mixture of aqueous sodium hydroxide (100 ml, 5 N) and diethyl ether (250 ml) at 0° C. After vigorous bubbling had ceased, the organic layer (containing diazomethane) was decanted into a chilled (0° C.) Erlenmeyer flask containing potassium hydroxide chips (20 g). The mixture was swirled for 10 min and the yellow solution was decanted into a dropping funnel. The solution of diazomethane was added over 30 min to an open flask containing a stirred mixture of (E)-[5-Fluoro-1-(p-toluenesulfonyl)indol-3-yl]-N-methoxy-N-methylacrylamide (8.0 g, 19.9 mmol) and palladium acetate (130 mg, 0.58 mmol) in dichloromethane (200 ml) maintained at 0° C. After stirring for 10 min., the reaction was quenched with glacial acetic acid (4 ml) and poured into an aqueous saturated solution of sodium bicarbonate (250 ml). The aqueous layer was extracted with ethyl acetate (3×100 ml). The organic layers were washed with brine, dried over anhydrous magnesium sulfate, and concentrated in vacuo. The crude product was purified by silica gel column chromatography (hexanes/ethyl acetate, 4:1) to afford 8.23 g (99% yield) of [trans-2-[5-fluoro-1-(p-toluenesulfonyl)indol-3-yl]cycloprop-1-yl]-N-methoxy-N-methylcarboxamide: $^1$H NMR (400 MHz, CDCl$_3$) 7.89 (1H, m), 7.72 (2H, d, J=8.4 Hz), 7.30 (1H, s), 7.23 (3H, m), 7.04 (1H, t, J=9.0 Hz), 3.71 (3H, s), 3.26 (3H, s), 2.40 (2H, m), 2.34 (3H, s), 1.59 (1H, m), 1.25 (1H, m); MS m/e 417 (M+H)$^+$.

Powdered lithium aluminum hydride (600 mg, 15.8 mmol) was carefully added portionwise to a stirred solution of [trans-(1R,2R)-2-[5-fluoro-1-(p-toluenesulfonyl)indol-3-yl]cycloprop-1-yl]-N-methoxy-N-methylcarboxamide (2.2 g, 5.28 mmol) in anhydrous tetrahydrofuran (100 ml) at −78° C. The resulting mixture was stirred at −78° C. for 2 h. The reaction was quenched with ethyl acetate (15 ml) and allowed to warmed to room temperature. After 30 min, water (1.0 ml) was added followed by a solution of aqueous sodium hydroxide (15% w/v, 2.0 ml). After stirring for 30 min at room temperature the aluminum salts were removed by vacuum filtration. The salts were rinsed with ethyl acetate (100 ml) and the combined filtrates were concentrated in vacuo. The crude material was purified by silica gel column chromatography (hexane/ethyl acetate, 4:1, 3:1) to afford 1.43 g (76% yield) of trans-2-[5-fluoro-1-(p-toluenesulfonyl)indol-3-yl]cyclopropanecarboxaldehyde as a off-white solid: $^1$H NMR (400 MHz, DMSO-$d_6$) 9.08 (1H, d, J=5.6 Hz), 7.90 (1H, m), 7.84 (2H, d, J=8.4 Hz), 7.75 (1H, s), 7.51 (1H, dd, J=9.1, 2.6 Hz), 7.38 (2H, d, J=8.1 Hz), 7.20 (1H, t, J=9.2 Hz), 2.69 (1H, m), 2.32 (3H, s), 2.09 (1H, m), 1.68 (2H, m); MS m/e 358 (M+H)$^+$. Anal. calcd. for $C_{19}H_{16}FNO_3S$: C, 63.85; H, 4.51; N, 3.91. Found: C, 63.55; H, 4.69; N, 3.71.

A mixture of trans-2-[5-Fluoro-1-(p-toluenesulfonyl)indol-3-yl]cyclopropane-carboxaldehyde (3.18 g, 8.90 mmol), dimethylamine (8.9 ml, 17.8 mmol, 2.0 M/THF), and anhydrous ethanol (100 ml) were heated to 80° C. with stirring until all solids were dissolved (20 min). The reaction vessel was removed from the heating source and sodium triacetoxyborohydride (7.55 g, 35.6 mmol) was added. After stirring for 1 h, the reaction vessel was placed in an ice-bath and quenched with aqueous hydrochloric acid (40 ml, 1 N). The resulting mixture was stirred for 20 min and then poured into a saturated aqueous solution of sodium bicarbonate (100 ml) and brine (50 ml). The aqueous layer was extracted with ethyl acetate (3×100 ml). The combined organic extracts were washed with brine (20 ml), dried over anhydrous magnesium sulfate, filtered, and concentrated in vacuo. The solid residue was dried under vacuum for 24 h and the crude trans-1-(N,N-dimethylaminomethyl)-2-[5-fluoro-1-toluenesulfonyl)indol-3-yl]cyclopropane subjected directly to reaction conditions used for cleavage of the N-tosyl group: $^1$H NMR (400 MHz, DMSO-$d_6$) 7.90 (1H, m), 7.83 (2H, d, J=8.4 Hz), 7.64 (1H, s), 7.57 (1H, dd, J=9.1, 2.5 Hz), 7.38 (2H, d, J=8.0 Hz), 7.20 (1H, t, J=9.2 Hz), 3.04 (2H, m), 2.71 (6H, s), 2.32 (3H, s), 2.02 (1H, m), 1.40 (1H, m), 1.21 (1H, m), 1.03 (1H, m); MS m/e 387 (M+H)$^+$.

Water (5 ml) and an aqueous solution of sodium hydroxide (2 ml, 10 N) were sequentially added to a flask charged with a solution of crude trans-1-(N,N-dimethylamino-methyl)-2-[5-fluoro-1-(p-toluenesulfonyl)indol-3-yl] cyclopropane (3.40 g, 8.80 mmol) dissolved in anhydrous ethanol (50 ml). The resulting mixture was heated at 70° C. for 16 h. After cooling to room temperature, the reaction was quenched with aqueous hydrochloric acid (21 ml, 1 N) and then poured into a mixture of saturated aqueous sodium bicarbonate (100 ml) and brine (50 ml). The aqueous layer was extracted with 10% methanol/ethyl acetate (4×100 ml). The combined organic layers were washed with brine (25 ml), dried over anhydrous sodium sulfate, filtered, and concentrated in vacuo. The crude material was purified by silica gel column chromatography using silica gel pretreated with 2% triethylamine in chloroform/methanol (9:1). The column was eluted using a step gradient of a ternary solvent mixture [chloroform/methanol/(2 M ammonia/methanol), 90/10/0, 85/15/1, 80/20/1, 80/20/2]. Trans-2-[5-cyanoindol-3-yl]-1-(N,N-dimethylaminomethyl)cyclopropane was obtained as a yellow residue (1.34 g, 68% yield) after drying under vacuum: $^1$H NMR (400 MHz, DMSO-d$_6$) 10.8 (1H, br s), 7.29 (2H, m), 7.09 (1H, s), 6.90 (1H, t, J=9.2 Hz), 2.39 (1H, m), 2.19 (7H, m), 1.69 (1H, m), 1.06 (1H, m), 0.85 (1H, m), 0.68 (1H, m); MS m/e 233 (M+H)$^+$.

EXAMPLE 3

Trans-2-[5-Cyanoindol-3-yl]-1-[N,N-methyl-benzylaminomethyl]-cyclopropane

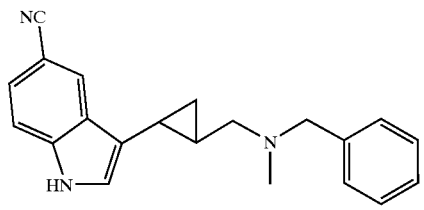

To a 1-dram vial were added trans-2-[5-cyano-1-(p-toluenesulfonyl)indol-3-yl]-cyclopropancarboxaldehyde (0.11 M in tetrahydrofuran, 0.5 ml, 0.055 mmol), N-methylbenzylamine (0.275 M in methanol, 1.0 ml, 0.275 mmol), and sodium triacetoxyborohydride (0.058 g, 0.275 mmol). The vial was sealed with a Teflon cap and gently heated at 40° C. for 4 hr on a shaken heating block. Sodium hydroxide (2.5 M in 50% methanol/water, 1.0 ml) was added and shaking at 55° C. continued for 1 hr. The solvent was evaporated by centrifugal evaporation and the solid residue partitioned between 1M sodium hydroxide and ethyl acetate. The organic phase was washed with 1M sodium hydroxide and evaporated. The residue was purified by preparative reverse phase high-performance liquid chromatography, eluting with a methanol/water/trifluoroacetic acid gradient, to afford the product as an oily trifluoroacetic acid salt (13.3 mg, 55%).

LC-MS: 1.09 min; 316.2 (MH)$^+$.

EXAMPLE 4

(1S,2S)-trans-1-(N,N-dimethylaminomethyl)-2-[5-fluoroindol-3-yl]-cyclopropane

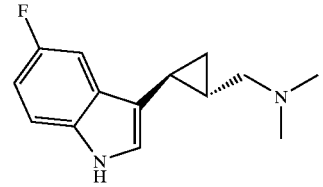

Sodium Hydride (66 mg of 60% in oil, 1.65 mmol) was washed with hexanes (2 ml) to remove oil and was suspended in THF (40 ml). (+)-3-(Diethylphosphonylacetyl) bornane-10,2-sultam (0.65 g, 1.65 mmol) in THF (10 ml) was then added over 10 min. The reaction was stirred for one hr at room temperature, then [5-fluoro-1-(p-toluenesulfonyl) indol-3-yl]carboxaldehyde (437 mg, 1.38 mmol) was added in one portion. The reaction was stirred 24 hr at room temperature and the solvent was removed in vacuo. The residue was taken up in water (100 ml) and was extracted with ethyl acetate (2×20 ml). The organic phase was dried with magnesium sulfate and evaporated to dryness. The crude product was purified by chromatography on silica. Elution with 15% to 25% ethyl acetate in hexanes provided 478 mg (62%) of (+)-N-[(E)-3-[5-fluoro-1-(p-toluenesulfonyl)indol-3-yl]-2-propenoyl]bornane-10,2-sultam as a white solid. $^1$H NMR (400 MHz, CDCl$_3$) 7.94 (1H, dd, J=9.1, 4.4 Hz), 7.90 (1H, s), 7.85 (1H, d, J=15.6 Hz), 7.76 (2H, d, J=8.4 Hz), 7.50 (1H, dd, J=9.0, 2.4 Hz), 7.26 (2H, d, J=8.1 Hz), 7.21 (1H, d, J=15.6 Hz), 7.10 (1H, td, J=8.9, 2.4 Hz), 3.99 (1H, dd, J=7.5, 5.1 Hz), 3.51 (2H, AB, Δv=28 Hz, J=13.7 Hz), 2.36 (3H, s), 2.26–2.10 (2H, m), 1.97–1.87 (3H, m), 1.49–1.32 (2H, m), 1.21 (3H, s), 1.00 (3H, s); MS m/e 557.3 (M+H)$^+$.

A solution of diazomethane in ether was prepared by slowly adding 1-methyl-3-nitro-1-nitrosoguanidine (872 mg, 5.9 mmol) to a mixture of diethyl ether (50 ml) and 5N NaOH (100 ml) at 0° C. and then decanting the ether layer. The ether layer was dried with potassium hydroxide and transferred to a dropping funnel. This ethereal diazomethane solution was then added dropwise over 15 min to a solution of (+)-N-[(E)-3-[5-fluoro-1-(p-toluenesulfonyl)indol-3-yl]-2-propenoyl]-bornane-10,2-sultam (330 mg, 0.59 mmol) and palladium(II)acetate (7 mg, 0.03 mmol) in dichloromethane (50 ml) at a temperature of –10° C. The reaction was stirred a further 15 min with the temperature maintained below –5° C., and was then quenched by the addition of acetic acid (2 ml). Water (50 ml) and 10 N NaOH (10 ml) were added and the layers were separated. The aqueous layer was extracted with ethyl acetate (2×20 ml) and the combined organic layers were dried with magnesium sulfate and evaporated to dryness. The crude product was purified by chromatography on silica (15% to 20% ethyl acetate/in hexanes) to afford 188 mg (56%) of N-[(1S,2S)-trans-2-[5-fluoro-1-(p-toluenesulfonyl)indol-3-yl]cycloprop-1-yl] carbonylbornane-10,2-sultam as a white solid.

A solution of N-[(1S,2S)-trans-2-[5-fluoro-1-(p-toluene-sulfonyl)indol-3-yl]cycloprop-1-yl]carbonylbornane-10,2-sultam (238 mg, 0.42 mmol) in THF (10 ml) was cooled to –40° C. (dry ice/acetonitrile). Lithium aluminum hydride (63 mg, 1.67 mmol) was added, with further additions (63 mg each) after 1 hr and 1.5 hr (reaction temperature maintained at –40° C. throughout). After a total reaction time of 2 hr ethyl acetate (5 ml) was added and the reaction was allowed to warm to room temperature. Water (200 ml) was added, and after 5 min, 1N NaOH (600 ml) was added. After another 5 min, more water (200 ml) was added, and the reaction was stirred a final 5 min. Some magnesium sulfate was added and the mixture was filtered through celite and sand and rinsed with ethyl acetate. The filtrate was evaporated to dryness. The crude material was partially purified on a short pad of silica by elution with 50% ethyl acetate in hexanes. (1S,2S)-trans-2-[5-fluoro-1-(p-toluenesulfonyl) indol-3-yl]cyclopropane-methanol appeared as an off-white solid (150 mg, 100%): $^1$H NMR (400 MHz, CDCl$_3$) 7.89 (1H, dd, J=9.0, 4.4 Hz) 7.70 (2H, d, J=8.4 Hz), 7.30–7.20 (4H, m), 7.03 (1H, td, J=9.0, 2.6 Hz), 3.73 (1H, dd, J=11.2, 6.4 Hz), 3.59 (1H, dd, J=11.2, 7.2 Hz), 2.34 (3H, s), 1.72 (1H, dt, J=9.6, 5.3 Hz), 1.34 (1H, m), 0.96–0.86 (2H, m); MS m/e 360.1 (M+H)$^+$.

Oxalyl chloride (58 ml, 0.67 mmol) in dichloromethane (10 ml) at −78° C. was treated with DMSO (54 ml, 0.76 mmol) dropwise. After addition the reaction was stirred for 10 min and a solution of (1S,2S)-trans-2-[5-fluoro-1-(p-toluenesulfonyl)indol-3-yl]-cyclopropanemethanol (150 mg, 0.42 mmol) in dichloromethane (5 ml) was added dropwise. After a further 15 min, triethylamine (341 ml, 2.45 mmol) was added dropwise. The reaction was stirred a further 5 min at −78° C. and was then allowed to warm to room temperature. The reaction was washed with water (3×5 ml), dried with magnesium sulfate and evaporated to dryness to give (1S,2S)-trans-2-[5-fluoro-1-(p-toluenesulfonyl) indol-3-yl]-cyclopropanecarboxaldehyde as a yellow oil.

The (1S,2S)-trans-2-[5-fluoro-1-(p-toluenesulfonyl) indol-3-yl]-cyclopropanecarboxaldehyde was dissolved in hot ethanol (5 ml) and treated with dimethylamine (0.45 ml of a 2M solution in THF, 0.90 mmol). After stirring 5 min, sodium triacetoxyborohydride (380 mg, 1.8 mmol) was added and the reaction was stirred 30 min. The solvent was removed in vacuo and the residue was taken up in brine (5 ml) and extracted with ethyl acetate (4×10 ml). The organic layer was dried with magnesium sulfate and evaporated to 125 mg (78% over 3 steps from sultam) (1S,2S)-trans-1-(N, N-dimethylaminomethyl)-2-[5-fluoro-1-(p-toluenesulfonyl) indol-3-yl]cyclopropane as a yellow oil: $^1$H NMR (400 MHz, CDCl$_3$) 7.87 (1H, dd, J=9.0, 4.4 Hz), 7.73 (2H, d, J=8.4 Hz), 7.32–7.27 (2H, m), 7.23 (2H, d, J=8.1 Hz), 7.06 (1H, td, J=9.1, 2.5 Hz), 3.16 (1H, dd, J=11.1, 6.5 Hz), 2.96 (1H, dd, J=11.2, 7.3 Hz), 2.82 (3H, s), 2.08 (6H, s), 2.03 (1H, m), 1.44 (1H, m), 1.18 (2H, t, J=7.2 Hz); MS m/e 387.4 (M+H)$^+$.

A solution of (1S,2S)-trans-1-dimethylamino-2-[5-fluoro-1-(p-toluenesulfonyl)-indol-3-yl]-cyclopropane (125 mg, 0.32 mmol) and 10 N sodium hydroxide (0.48 ml, 4.9 mmol) in ethanol (10 ml) and water (1 ml) was heated at reflux for 5 hr. The reaction was cooled to room temperature, poured into brine (100 ml) and extracted with ethyl acetate (2×20 ml) and 9:1 ethyl acetate/methanol (3×50 ml). The organic layer was dried with magnesium sulfate and evaporated. The residue was purified by chromatography on silica with 90:10:1 chloroform/methanol/2M ammonia in methanol to provide (1S,2S)-trans-1-(N,N-dimethylaminomethyl)-2-[5-fluoroindol-3-yl]-cyclopane as a clear oil that solidified on standing (68 mg, 71% over 4 steps from sultam): mp 88–90° C.; [α$_D$]=+51.4° (c=2.45 mg/ml, ethanol); $^1$H NMR (400 MHz, CDCl$_3$) 8.05 (1H, brs), 7.33 (1H, dd, J=9.6, 2.5 Hz), 7.24 (1H, dd, J=8.8, 4.4 Hz), 6.98–6.88 (2H, m), 2.45 (1H, dd, J=11.0, 6.5 Hz), 2.37 (1H, dd, J=11.1, 6.8 Hz), 2.35 (6H, s), 1.68 (1H, m), 1.21 (1H, m), 0.87 (1H, m), 0.76 (1H, m); MS m/e 233.1 (M+H)$^+$.

EXAMPLE 5

(1S,2S)-trans-2-[5-cyanoindol-3-yl]-1-(N,N-dimethylaminomethyl)-cyclopropane

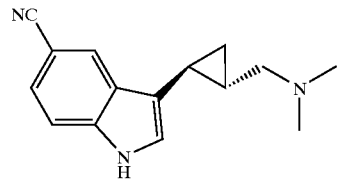

Sodium Hydride (0.69 g of 60% in oil, 17.3 mmol) was washed with hexanes (5 ml) to remove oil and was suspended in THF (500 ml) at 0° C. (+)-3-(Diethylphosphonylacetyl)bornane-10,2-sultam (6.8 g, 17.3 mmol) in THF (50 ml) was then added over 10 min. The reaction was stirred for 1 hr at room temperature, then re-cooled to 0° C. before adding [5-cyano-1-(p-toluenesulfonyl)indol-3-yl]carboxaldehyde (4.67 mg, 14.4 mmol) in one portion. The reaction was stirred 24 hr at room temperature and the solvent was removed in vacuo. The residue was taken up in water (100 ml) and was extracted with ethyl acetate (3×50 ml). The organic phase was dried with magnesium sulfate and allowed to stand for 16 hr. The resulting crystals were collected by filtration. The filtrate was evaporated and the residue was recrystallized from ethyl acetate and hexanes to give a second crop of crystals. A total of 4.71 g (58%) (+)-N-[(E)-3-[5-cyano-1-(p-toluenesulfonyl)indol-3-yl]-2-propenoyl]-bornane-10,2-sultam was collected as a white solid: mp 203–205° C.; $^1$H NMR (400 MHz, CDCl$_3$): δ 8.15 (1H, s), 8.09 (1H, d, J=8.8 Hz), 7.98 (1H, s), 7.81 (1H, d, J=15.7 Hz), 7.80 (2H, d, J=8.4 Hz), 7.62 (1H, dd, J=8.6, 1.4 Hz), 7.29 (2H, d, J=8.1 Hz), 7.25 (1H, d, J=15.6 Hz), 3.99 (1H, dd, J=7.4, 5.2 Hz), 3.53 (2H, AB, Δv=32 Hz, J=13.8 Hz), 2.38 (3H, s), 2.25–2.12 (2H, m), 2.01–1.87 (3H, m), 1.48–1.32 (2H, m), 11.21 (3H, s), 1.00 (3H, s); MS m/e 564.3 (M+H)$^+$.

The following reaction was performed behind a blast shield using glassware without ground glass joints. A solution of diazomethane in ether was prepared by slowly adding 1-methyl-3-nitro-1-nitrosoguanidine (13.3 g, 90 mmol) to a mixture of diethyl ether (200 ml) and 5N NaOH (200 ml) at 0° C. and then decanting the ether layer. The ether layer was dried with potassium hydroxide and transferred to a dropping funnel. This ethereal diazomethane solution was then added dropwise over 30 min to a solution of (+)-N-[(E)-3-[5-cyano-1-(p-toluenesulfonyl)indol-3-yl]-2-propenoyl] bornane-10,2-sultam (5.1 g, 9.0 mmol) and palladium(II) acetate (100 mg, 0.45 mmol) in dichloromethane (200 ml) at a temperature of −10° C. The reaction was stirred a further 20 min with the temperature maintained below −5° C., and was then quenched by the addition of acetic acid (6 ml). To the reaction 1 N NaOH (10 ml) was added and the layers were separated. The aqueous layer was extracted with ethyl acetate (2×30 ml) and the combined organic layers were dried with magnesium sulfate and evaporated to dryness. The crude product was purified by chromatography on silica (20% ethyl acetate/in hexanes) to afford the 3.23 g (62%) of the product as a white solid. This material was recrystallized from 350 ml of boiling EtOH to provide 1.18 g of crystals. The mother liquor was evaporated and recrystallized from 100 ml of boiling EtOH to provide a second crop of 1.22 g. The total amount of recrystallized N-[(1S,2S)-trans-2-[5- cyano-1-(p-toluenesulfonyl)indol-3-yl]cycloprop-1-yl] carbonylbornane-10,2-sultam was 2.40 g (46%) as a white solid: mp 188–190° C.; $^1$H-NMR (400 MHz, CDCl$_3$) 8.03 (1H, d, J=8.6 Hz), 7.99 (1H, d, J=1.0 Hz), 7.75 (2H, d, J=8.4 Hz), 7.57 (1H, d, J=1.2 Hz), 7.54 (1H, dd, J=8.6, 1.5 Hz), 7.25 (2H, m), 3.96 (1H, dd, J=7.4, 5.1 Hz), 3.53 (2H, AB, Δv=18 Hz, J=13.8 Hz), 2.57 (1H, dt, J=7.7, 4.8 Hz), 2.45 (1H, m), 2.36 (3H, s), 2.16–2.04 (2H, m), 2.00–1.87 (3H, m), 1.81 (1H, dt, J=9.1, 4.3 Hz), 1.55 (3H, s), 1.50–1.32 (2H, m), 1.29 (1H, m), 1.21 (3H, s), 1.00 (3H, s); MS m/e 578.2 (M+H)$^+$.

A solution of N-[(1S,2S)-trans-2-[5-cyano-1-(p-toluenesulfonyl)indol-3-yl]cycloprop-1-yl] carbonylbornane-10,2-sultam (2.30 g, 3.98 mmol) in THF (100 ml) was cooled to −40° C. (dry ice/acetonitrile). Lithium aluminum hydride (600 mg, 15.9 mmol) was added, with a further addition (600 mg) after 1 hr (reaction temperature maintained at −40° C. throughout). After a total reaction time of 1.5 hr ethyl acetate (50 ml) was added and the reaction was allowed to warm to room temperature. Water (1.2 ml) was added, and after 10 min 1N NaOH (3.6 ml) was added. After another 5 min, more water (1.2 ml) was added, and the reaction was stirred a final 15 min. Some magnesium sulfate was added and the mixture was filtered through celite and sand and rinsed with ethyl acetate. The filtrate was evaporated to dryness. The crude material was partially purified on a short pad of silica by elution with 50% ethyl acetate in hexanes. The (1S,2S)-trans-2-[5-cyano-1-(p-toluenesulfonyl)indol-3-yl]-cyclo-propanemethanol appeared as a white solid (1.18 mg, 81%): mp 140–141° C.; $^1$H NMR (400 MHz, CDCl$_3$) 8.03 (1H, dd, J=8.6, 0.6 Hz), 8.00 (1H, d, J=1.5 Hz), 7.74 (2H, d, J=8.6 Hz), 7.55 (1H, dd, J=8.6, 1.5 Hz), 7.33 (1H, d, J=1.0 Hz), 7.26 (2H, d, J=8.5 Hz), 3.77 (1H, m), 3.60 (1H, m), 2.37 (3H, s), 1.77 (1H, m,), 1.37 (1H, m), 0.95 (2H, t, J=7.0 Hz); MS m/e 349.1 (M−OH+H)$^+$.

Oxalyl chloride (0.42 ml, 4.8 mmol) in dichloromethane (50 ml) at −78° C. was treated with DMSO (0.39 ml, 5.4 mmol) dropwise. After addition the reaction was stirred for 15 min and a solution of (1S,2S)-trans-2-[5-cyano-1-(p-toluenesulfonyl)indol-3-yl]-cyclopropanemethanol (1.17 g, 3.2 mmol) in dichloromethane (10 ml) was added dropwise. After a further 15 min, triethylamine (2.45 ml, 17.6 mmol) was added dropwise. The reaction was stirred a further 5 min at −78° C. and was then allowed to warm to room temperature. The reaction was washed with water (2×10 ml), dried with magnesium sulfate and evaporated to dryness to give a yellow oil.

The crude (1S,2S)-trans-2-[5-cyano-1-(p-toluenesulfonyl)indol-3-yl]-cyclopropanecarboxaldehyde from the above procedure was dissolved in hot ethanol (50 ml) and treated with dimethylamine (3.2 ml of a 2M solution in THF, 6.4 mmol). After stirring 5 min, sodium triacetoxyborohydride (2.71 g, 12.8 mmol) was added in several portions over 10 min while the reaction was cooled in a 10° C. water bath. After stirring 45 min at room temperature the solvent was removed in vacuo and the residue was taken up in brine (10 ml) and 1N sodium hydroxide was added until solids disappeared. The reaction was extracted with ethyl acetate (4×10 ml), the organic layer was dried with magnesium sulfate and evaporated to give (1S,2S)-trans-1-(N,N-dimethylaminomethyl)-2-[5-cyano-1-(p-toluenesulfonyl) indol-3-yl]-cyclopropane as a yellow oil.

The crude (1S,2S)-trans-1-(N,N-dimethylaminomethyl)-2-[5-cyano-1-(p-toluenesulfonyl)indol-3-yl]-cyclopropane was dissolved in ethanol (25 ml) and water (4 ml) with 10 N sodium hydroxide (2 ml, 20 mmol) and was heated at 70° C. for 1 hr. The reaction was cooled to room temperature, poured into brine (100 ml) and extracted with ethyl acetate (2×50 ml) and 9:1 ethyl acetate/methanol (3×50 ml). The organic layer was dried with magnesium sulfate and evaporated. The residue was purified by chromatography on silica with 90:10:1 chloroform/methanol/2M ammonia in methanol to provide the product (1S,2S)-trans-2-[5-cyanoindol-3-yl]-1-(N,N-dimethylaminomethyl)cyclopropane as a yellow oil. (590 mg, 77% over 3 steps from alcohol): [α$_D$]=+17.5° (c=2.92 mg/ml, ethanol); $^1$H NMR (400 MHz, CDCl$_3$) 8.82 (1H, brs), 8.04 (1H, s), 7.38 (1H, dd, J=7.2, 1.4 Hz), 7.34 (1H, dd, 7.2, 0.5 Hz), 6.96 (1H, d, J=1.6 Hz), 2.49 (1H, dd, J=12.4, 6.4 Hz), 2.37 (1H, dd, J=12.4, 7.0 Hz), 2.37 (6H, s), 1.76 (1H, m), 1.23 (1H, m), 0.90 (1H, m), 0.84 (1H, m); MS m/e 240.1 (M+H)$^+$.

EXAMPLE 6 trans-2-[5-Cyanoindol-3-yl]-1-[N,N-methyl-2-amino (isopropylcarbamoyl)ethylaminomethyl]-cyclopropane

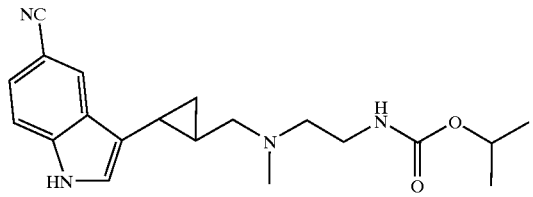

(2-Bromo-ethyl)-carbamic acid isopropyl ester

A mixture of bromoethylamine hydrobromide (5.0 g, 24.4 mmol), isopropyl chloroformate (1.0 M in tetrahydrofuran, 16.3 ml, 16.3 mmol), and anhydrous dichloromethane (100 ml) was treated with triethylamine (4.5 ml, 33 mmol) and stirred at ambient temperature for 18 hr. The mixture was diluted with dichloromethane (200 ml), washed with 1 M hydrochloric acid, 1 M sodium hydroxide, and brine, dried over sodium sulfate and evaporated to give (2-bromo-ethyl)-carbamic acid isopropyl ester clear oil. $^1$H-NMR δ (CDCl$_3$) 5.01 (1H, br s), 4.92 (m, 1H), 3.58 (m, 2H), 3,48 (m, 2H), 1.25 (m, 6H).

To a 1-dram vial were added (2-bromo-ethyl)-carbamic acid isopropyl ester (30 mg, 0.143 mmol), trans-2-[5-cyano-1-(p-toluenesulfonyl)indol-3-yl]-1-[N-methylaminomethyl]-cyclopropane (0.13 M in methanol, 1.0 ml, 0.13 mmol), and triethylamine (0.10 ml, 0.72 mmol). The vial was sealed with a Teflon cap and heated to 60° C. on a shaken heating block for 18 hr. Sodium hydroxide (1 M, 1 ml) was added and heating at 60° C. continued for 1 hr. The solvent was evaporated and the residue partitioned between 1 M sodium hydroxide and ethyl acetate. The aqueous phase was extracted with ethyl acetate and the pooled extracts dried over sodium sulfate and concentrated to an oily solid. Purification by preparative reverse phase high-performance liquid chromatography afforded the product as an oily trifluoroacetic acid salt. LC-MS: 1.15 min; 355.28 (MH)$^+$.

Examples 7–115 were prepared by the methods illustrated in previous examples:

EXAMPLE 7 trans-1-(N-Benzlyaminomethyl)-2-[5-cyanoindol-3-yl]-cyclopropane

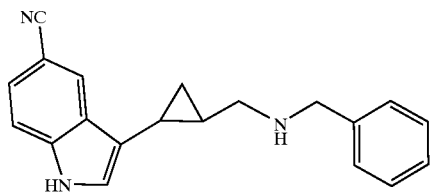

LC-MS: 1.08 min; 302.19 (MH)⁺.

EXAMPLE 8 trans-2-[5-Cyanoindol-3-yl]-1-[N-(2-methoxybenzyl)aminomethyl]-cyclopropane

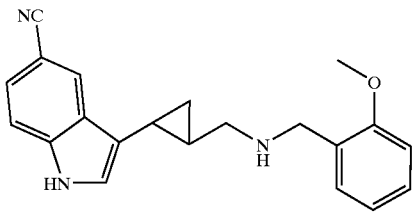

LC-MS: 1.16 min; 332.19 (MH)⁺.

EXAMPLE 9 trans-2-[5-Cyanoindol-3-yl]-1-[N-(3-methoxybenzyl)aminomethyl]-cyclopropane

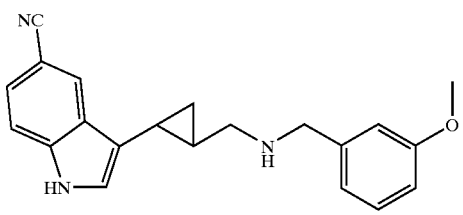

LC-MS: 1.13 min; 332.19 (MH)⁺.

EXAMPLE 10 trans-2-[5-Cyanoindol-3-yl]-1-[N-(4-methoxybenzyl)amnomethyl]-cyclopropane

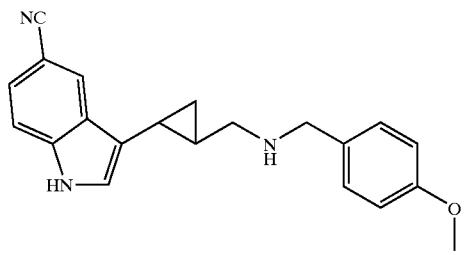

LC-MS: 1.13 min; 332.17 (MH)⁺.

EXAMPLE 11 trans-2-[5-Cyanoindol-3-yl]-1-[N-(2-fluorobenzyl)aminomethyl]-cyclopropane

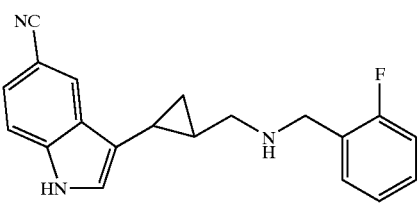

LC-MS: 1.08 min; 320.17 (MH)⁺.

EXAMPLE 12 trans-2-[5-Cyanoindol-3-yl]-1-[N-(3-fluorobenzyl)aminomethyl]-cyclopropane

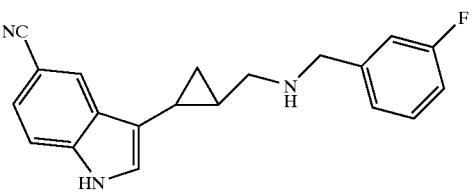

LC-MS: 1.09 min; 320.17 (MH)⁺.

EXAMPLE 13 trans-2-[5-Cyanoindol-3-yl]-1-[N-(4-fluorobenzyl)aminomethyl]-cyclopropane

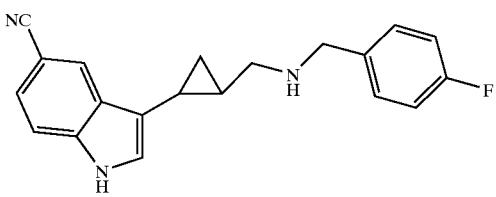

LC-MS: 1.10 min; 320.16 (MH)⁺.

EXAMPLE 14 trans-2-[5-Cyanoindol-3-yl]-1-[N-(2-pyridylmethyl)aminomethyl]-cyclopropane

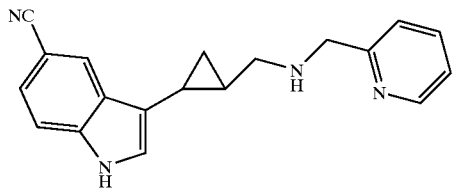

LC-MS: 0.95 min; 303.16 (MH)⁺.

EXAMPLE 15 trans-2-[5-Cyanoindol-3-yl]-1-[N-(3-pyridyl)methylaminomethyl]-cyclopropane

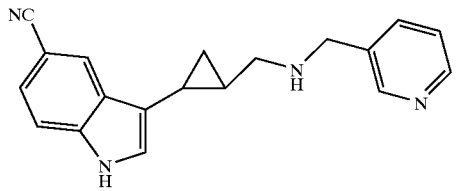

LC-MS: 0.71 min; 303.16 (MH)⁺.

EXAMPLE 16 trans-2-[5-Cyanoindol-3-yl]-1-[N-(4-pyridyl)methylaminomethyl]-cyclopropane

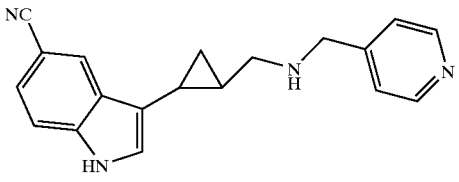

LC-MS: 0.69 min; 303.16 (MH)⁺.

EXAMPLE 17 trans-2-[5-Cyanoindol-3-yl]-1-[N-2-(2-fluorophenyl)ethylaminomethyl]-cyclopropane

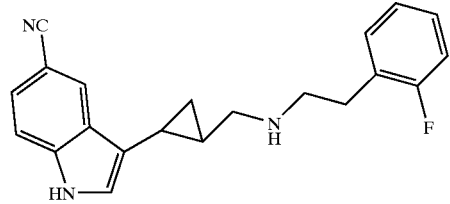

LC-MS: 1.15 min; 334.17 (MH)⁺.

EXAMPLE 18 trans-2-[5-Cyanoindol-3-yl]-1-[N-2-(3-fluorophenyl)ethylaminomethyl]-cyclopropane

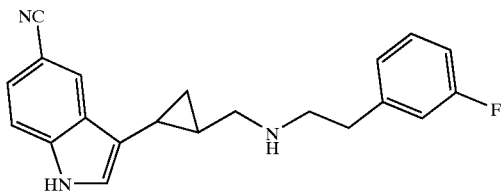

LC-MS: 1.15 min; 334.18 (MH)⁺.

EXAMPLE 19 trans-2-[5-Cyanoindol-3-yl]-1-[N-2-(4-fluorophenyl)ethylaminomethyl]-cyclopropane

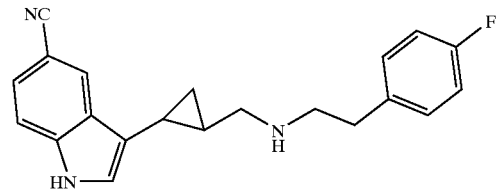

LC-MS: 1.15 min; 334.18 (MH)⁺.

EXAMPLE 20 trans-2-[5-Cyanoindol-3-yl]-1-[N-2-(3-pyridyl)ethylaminomethyl]-cyclopropane

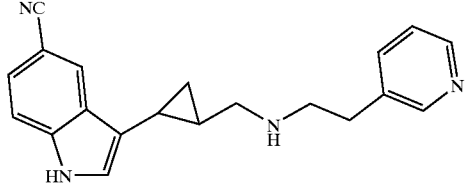

LC-MS: 0.77 min; 317.19 (MH)⁺.

EXAMPLE 21 trans-2-[5-Cyanoindol-3-yl]-1-[N-3-phenylpropylaminomethyl]-cyclopropane

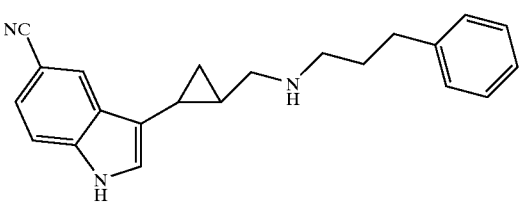

LC-MS: 1.20 min; 330.20 (MH)⁺.

EXAMPLE 22 trans-2-[5-Cyanoindol-3-yl]-1-[N-3-(3-pyridyl)
propylaminomethyl]-cyclopropane

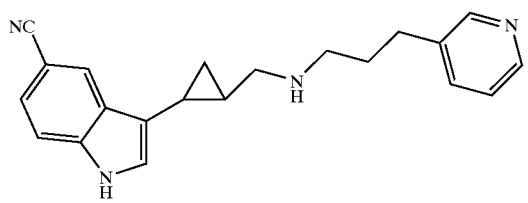

LC-MS: 0.67 min; 330.18 (MH)+.

EXAMPLE 23 trans-2-[5-Cyanoindol-3-yl]-1-[N-2-(4-imidazolyl)
ethylaminomethyl]-cyclopropane

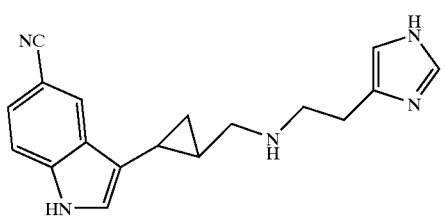

LC-MS: 0.68 min; 306.17 (MH)+.

EXAMPLE 24 trans-2-[5-Cyanoindol-3-yl]-1-[N-3-(1-imidazolyl)
propylaminomethyl]-cyclopropane

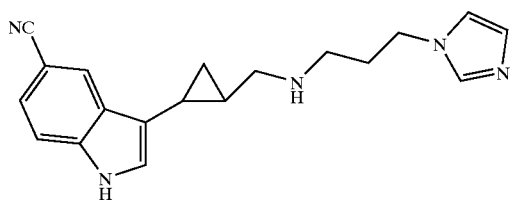

LC-MS: 0.69 min; 320.21 (MH)+.

EXAMPLE 25 trans-2-[5-Cyanoindol-3-yl]-1-[N-2-thiopheneyl)
ethylaminomethyl]-cyclopropane

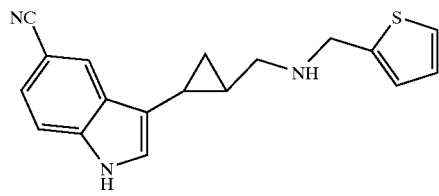

LC-MS: 1.03 min; 322.15 (MH)+.

EXAMPLE 26 trans-2-[5-Cyanoindol-3-yl]-1-[N-2-(2-thipheneyl)
ethylaminomethyl]-cyclopropane

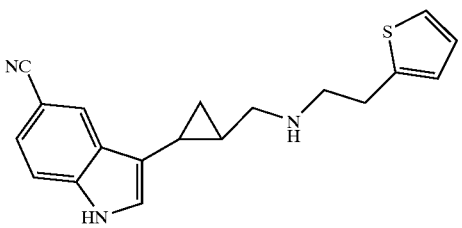

LC-MS: 1.07 min; 322.15 (MH)+.

EXAMPLE 27 trans-2-[5-Cyanoindol-3-yl]-1-[N-2-(3-indolyl)
ethylaminomethyl]-cyclopropane

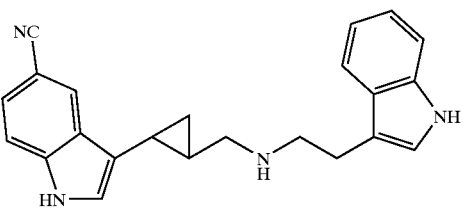

LC-MS: 1.16 min; 355.19 (MH)+.

EXAMPLE 28 trans-2-[5-Cyanoindol-3-yl]-1-[N-
cyclopropylmethylaminomethyl]-cyclopropane

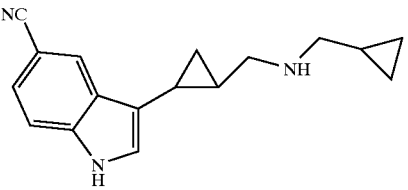

LC-MS: 0.91 min; 266.15 (MH)+.

EXAMPLE 29 trans-2-[5-Cyanoindol-3-yl]-1-[N-
cyclohexylaminomethyl]-cyclopropane

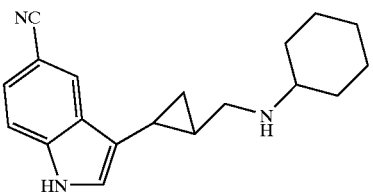

LC-MS: 1.08 min; 294.19 (MH)+.

EXAMPLE 30 trans-2-[5-Cyanoindol-3-yl]-1-[N-cyclohexylmethylaminomethyl]-cyclopropane

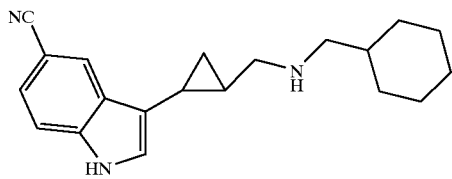

LC-MS: 1.19 min; 308.22 (MH)+.

EXAMPLE 31 trans-2-[5-Cyanoindol-3-yl]-1-[N-isobutylaminomethyl]-cyclopropane

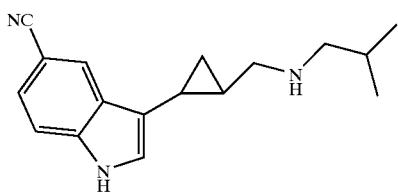

LC-MS: 1.10 min; 268.17 (MH)+.

EXAMPLE 32 trans-2-[5-Cyanoindol-3-yl]-1-[N-3-methyl-butylaminomethyl]-cyclopropane

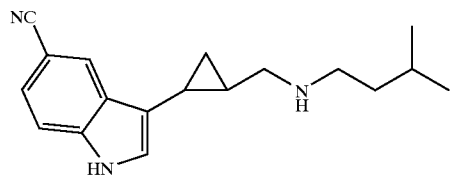

LC-MS: 1.08 min; 282.12 (MH)+.

EXAMPLE 33 trans-2-[5-Cyanoindol-3-yl]-1-(4-methyl-piperidin-1-yl-methyl)-cyclopropane

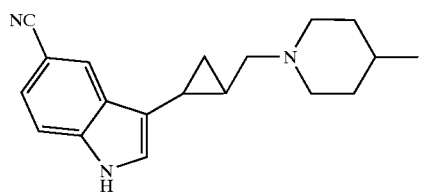

LC-MS: 0.98 min; 294.20 (MH)+.

EXAMPLE 34 trans-1-(4-Benzyl-piperidin-1-ylmethyl)-2-[5-cyanoindol-3-yl]-cyclopropane

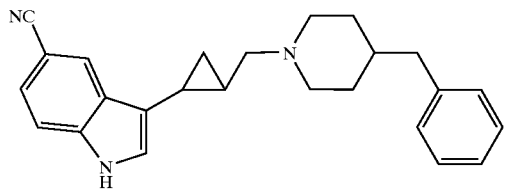

LC-MS: 1.26 min; 370.23 (MH)+.

EXAMPLE 35 trans-2-[5-Cyanoindol-3-yl]-1-(piperazin-1-yl-methyl)-cyclopropane

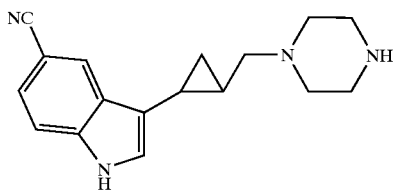

LC-MS: 0.64 min; 281.16 (MH)+.

EXAMPLE 36 trans-1-[4-Benzyl-piperazin-1-yl-methyl]-2-[5-cyanoindol-3-yl]-cyclopropane

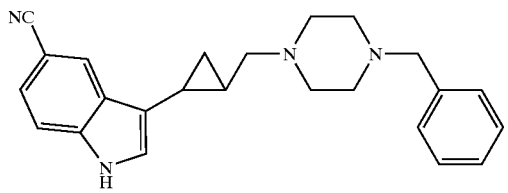

LC-MS: 0.87 min; 371.23 (MH)+.

EXAMPLE 37 trans-2-[5-Cyanoindol-3-yl]-1-[1,2,3,4-tetrahydro-1H-isoquinolin-2-yl-methyl]-cyclopropane

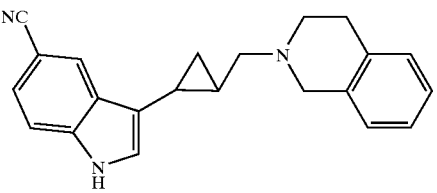

LC-MS: 1.06 min; 328.19 (MH)+.

EXAMPLE 38 trans-2-[5-Cyanoindol-3-yl]-1-[N,N-dipropylaminomethyl]-cyclopropane

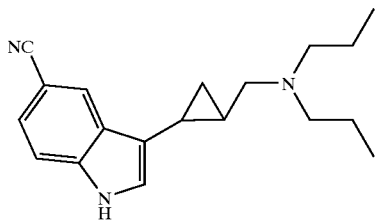

LC-MS: 1.01 min; 296.22 (MH)⁺.

EXAMPLE 39 trans-2-[5-Cyanoindol-3-yl]-1-[N,N-methyl-phenylethylaminomethyl]-cyclopropane

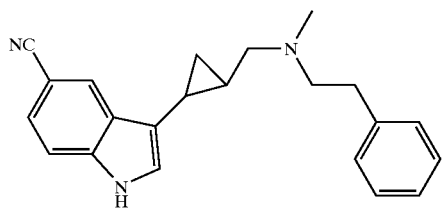

LC-MS: 1.13 min; 330.20 (MH)⁺.

EXAMPLE 40 trans-2-[5-Cyanoindol-3-yl]-1-[N-phenylethylamino]-cyclopropane

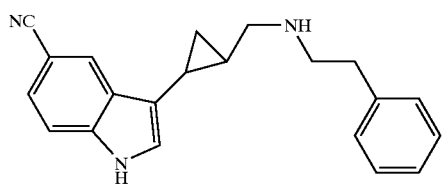

LC-MS: 1.12 min; 316.20 (MH)⁺.

EXAMPLE 41 trans-2-[5-Cyanoindol-3-yl]-1-[N-2-(2-methoxyphenyl)ethylamino]-cyclopropane

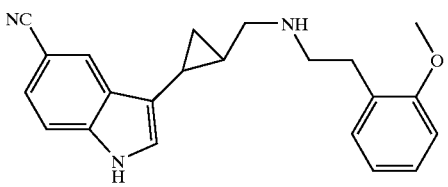

LC-MS: 1.20 min; 346.19 (MH)⁺.

EXAMPLE 42 trans-2-[5-Cyanoindol-3-yl]-1-[N-2-(3-methoxyphenyl)ethylamino]-cyclopropane

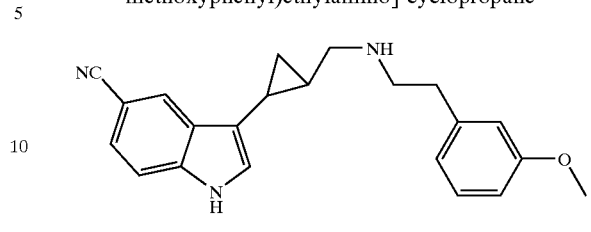

LC-MS: 1.15 min; 346.19 (MH)⁺.

EXAMPLE 43 trans-2-[5-Cyanoindol-3-yl]-1-[N-2-(4-methoxyphenyl)ethylamino]-cyclopropane

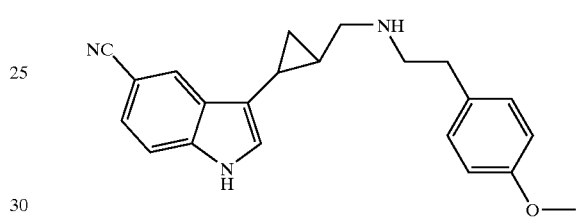

LC-MS: 1.15 min; 346.19 (MH)⁺.

EXAMPLE 44 trans-2-[5-Cyanoindol-3-yl]-1-[N-2-phenoxy-ethylamino]-cyclopropane

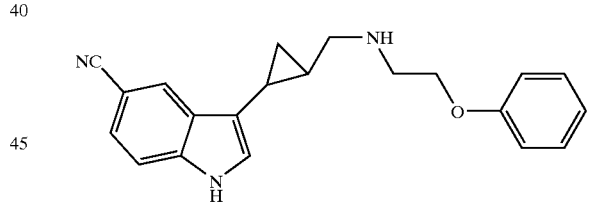

LC-MS: 1.15 min; 332.19 (MH)⁺.

EXAMPLE 45 trans-2-[5-Cyanoindol-3-yl]-1-[N-propylamino]-cyclopropane

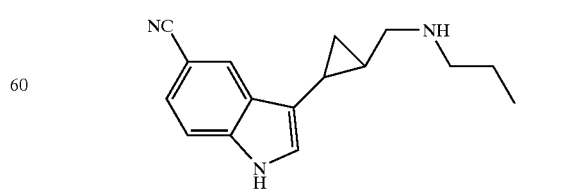

LC-MS: 0.77 min; 254.14 (MH)⁺.

EXAMPLE 46 trans-2-[5-Cyanoindol-3-yl]-1-[pyrrolidin-1-yl-methyl]-cyclopropane

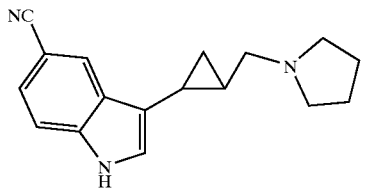

LC-MS: 0.85 min; 266.15 (MH)+.

EXAMPLE 47 trans-2-[5-Cyanoindol-3-yl]-1-[piperidin-1-yl-methyl]-cyclopropane

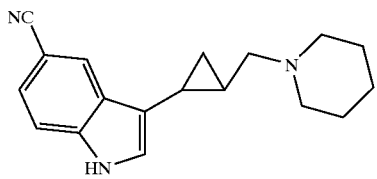

LC-MS: 0.90 min; 280.17 (MH)+.

EXAMPLE 48 trans-2-[5-Cyanoindol-3-yl]-1-[N,N-diethylamino]-cyclopropane

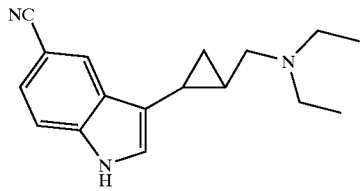

LC-MS: 0.89 min; 268.16 (MH)+.

EXAMPLE 49 trans-1-(N-Benzylaminomethyl)-2-[5-fluoroindol-3-yl]-cyclopropane

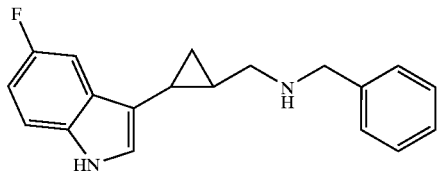

LC-MS: 1.17 min; 295.15 (MH)+.

EXAMPLE 50 trans-2-[5-Fluoroindol-3-yl]-1-[N-(2-methoxybenzyl)aminomethyl]-cyclopropane

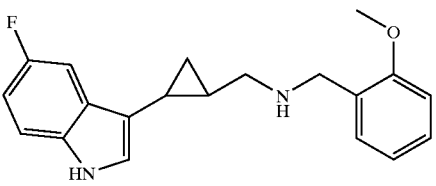

LC-MS: 1.24 min; 325.20 (MH)+.

EXAMPLE 51 trans-2-[5-Fluoroindol-3-yl]-1-[N-(3-methoxybenzyl)aminomethyl]-cyclopropane

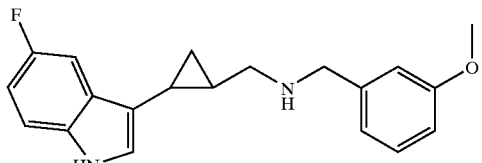

LC-MS: 1.21 min; 325.19 (MH)+.

EXAMPLE 52 trans-2-[5-Fluoroindol-3-yl]-1-[N-(4-methoxybenzyl)aminomethyl]-cyclopropane

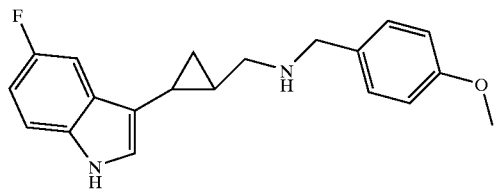

LC-MS: 1.21 min; 325.20 (MH)+.

EXAMPLE 53 trans-1-[N-(2-Fluorobenzyl)aminomethyl]2-[5-fluoroindol-3-yl]-cyclopropane

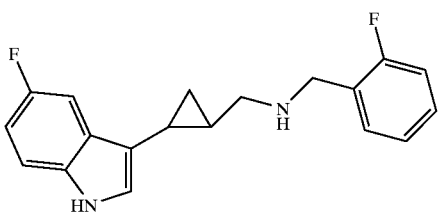

LC-MS: 1.17 min; 313.17 (MH)+.

EXAMPLE 54 trans-1-[N-(3-Fluorobenzyl)aminomethyl]2-[5-fluoroindol-3-yl]-cyclopropane

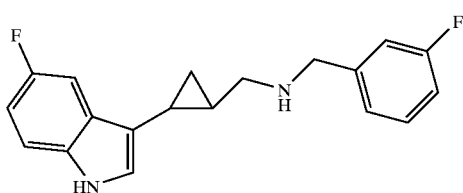

LC-MS: 1.18 min; 313.17 (MH)$^+$.

EXAMPLE 55 trans-1-[N-(4-Fluorobenzyl)aminomethyl]2-[5-fluoroindol-3-yl]-cyclopropane

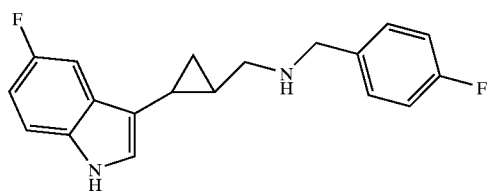

LC-MS: 1.20 min; 313.17 (MH)$^+$.

EXAMPLE 56 trans-2-[5-Fluoroindol-3-yl]-1-[N-(2-pyridylmethyl)aminomethyl]-cyclopropane

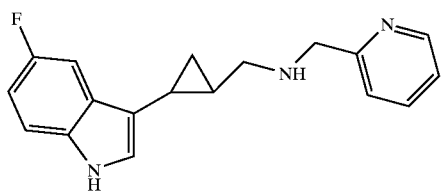

LC-MS: 1.02 min; 296.15 (MH)$^+$.

EXAMPLE 57 trans-2-[5-Fluoroindol-3-yl]-1-[N-(3-pyridylmethyl)aminomethyl]-cyclopropane

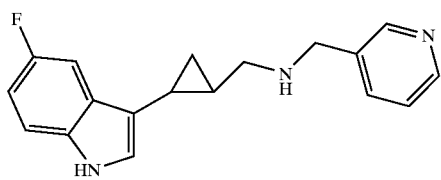

LC-MS: 0.71 min; 296.14 (MH)$^+$.

EXAMPLE 58 trans-2-[5-Fluoroindol-3-yl]-1-[N-(4-pyridylmethyl)aminomethyl]-cyclopropane

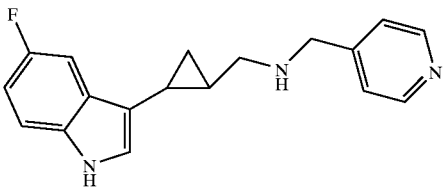

LC-MS: 0.70 min; 296.15 (MH)$^+$.

EXAMPLE 59 trans-2-[5-Fluoroindol-3-yl]-1-[N-(2-fluorophenyl)ethylaminomethyl]-cyclopropane

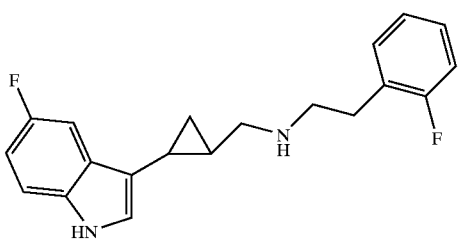

LC-MS: 1.25 min; 327.19 (MH)$^+$.

EXAMPLE 60 trans-2-[5-Fluoroindol-3-yl]-1-[N-(3-fluorophenyl)ethylaminomethyl]-cyclopropane

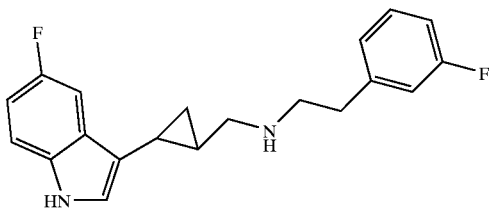

LC-MS: 1.24 min; 327.18 (MH)$^+$.

EXAMPLE 61 trans-2-[5-Fluoroindol-3-yl]-1-[N-(4-fluorophenyl)ethylaminomethyl]-cyclopropane

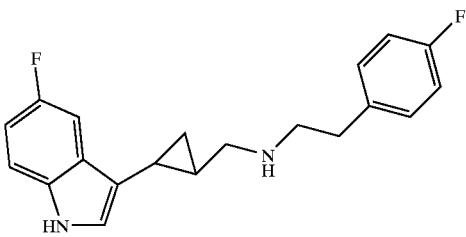

LC-MS: 1.24 min; 327.19 (MH)$^+$.

EXAMPLE 62 trans-2-[5-Fluoroindol-3-yl]-1-[N-3-phenylpropylaminomethyl]-cyclopropane

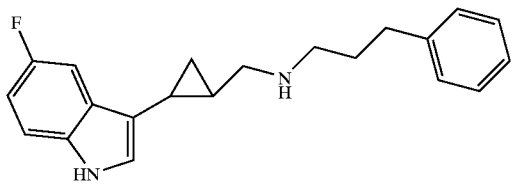

LC-MS: 1.31 min; 323.21 (MH)⁺.

EXAMPLE 63 trans-2-[5-Fluoroindol-3-yl]-1-[N-3-(3-pyridyl)propylaminomethyl]-cyclopropane

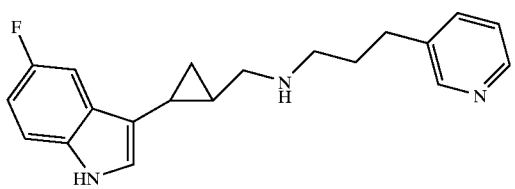

LC-MS: 0.77 min; 325.22 (MH)⁺.

EXAMPLE 64 trans-2-[5-Fluoroindol-3-yl]-1-[N-2-(4-imidazolyl)ethylaminomethyl]-cyclopropane

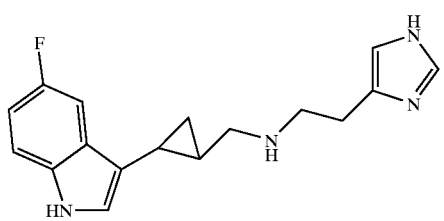

LC-MS: 0.69 min; 299.15 (MH)⁺.

EXAMPLE 65 trans-2-[5-Fluoroindol-3-yl]-1-[N-3-(1-imidazolyl)propylaminomethyl]-cyclopropane

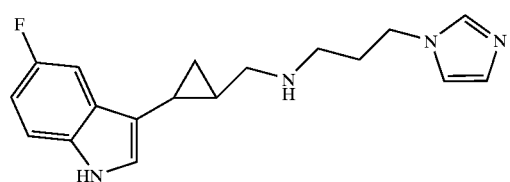

LC-MS: 0.71 min; 313.19 (MH)⁺.

EXAMPLE 66 trans-2-[5-Fluoroindol-3-yl]-1-[N-2-thiopheneylmethylaminomethyl]-cyclopropane

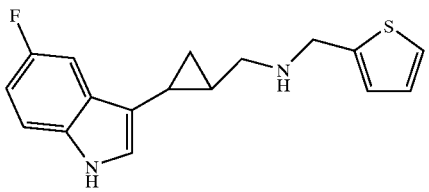

LC-MS: 1.10 min; 301.11 (MH)⁺.

EXAMPLE 67 trans-2-[5-Fluoroindol-3-yl]-1-[N-2-(2-thiopheneyl)ethylaminomethyl]-cyclopropane

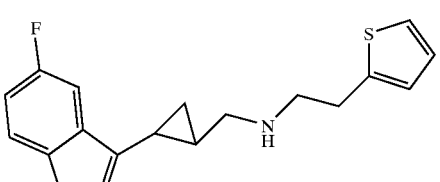

LC-MS: 1.15 min; 315.14 (MH)⁺.

EXAMPLE 68 trans-2-[5-Fluoroindol-3-yl]-1-[N-2-(3-indolyl)ethylaminomethyl]-cyclopropane

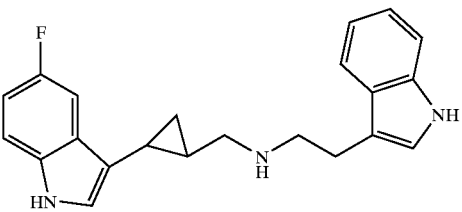

LC-MS: 1.25 min; 348.18 (MH)⁺.

EXAMPLE 69 trans-1-[N-Cyclopropylmethylaminomethyl]-2-[5-fluoroindol-3-yl]-cyclopropane

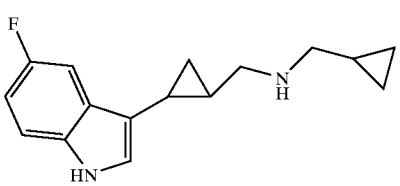

LC-MS: 0.82 min; 257.18 (MH)⁺.

EXAMPLE 70 trans-1-[N-Cyclohexylaminomethyl]-2-[5-fluoroindol-3-yl]-cyclopropane

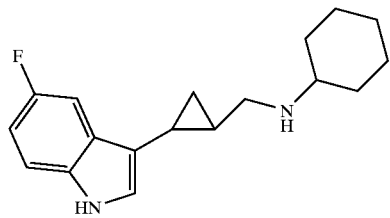

LC-MS: 1.16 min; 287.17 (MH)$^+$.

EXAMPLE 71 trans-1-[N-Cyclohexylmethylaminomethyl]-2-[5-fluoroindol-3-yl]-cyclopropane

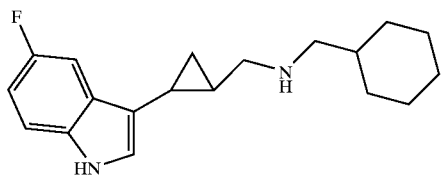

LC-MS: 1.28 min; 301.20 (MH)$^+$.

EXAMPLE 72 trans-2-[5-Fluoroindol-3-yl]-1-[N-3-methyl-butylaminomethyl]-cyclopropane

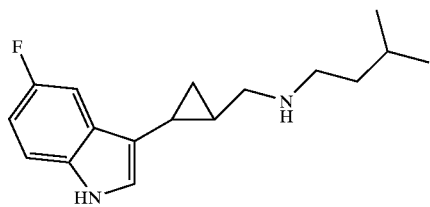

LC-MS: 1.17 min; 275.18 (MH)$^+$.

EXAMPLE 73 trans-1-(4-Benzyl-piperidin-1-yl-methyl)-2-[5-fluoroindol-3-yl]-cyclopropane

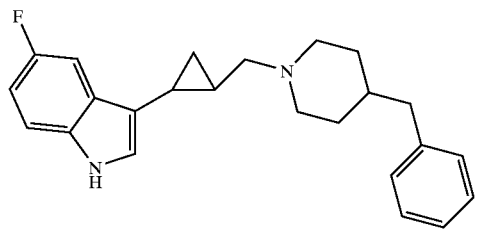

LC-MS: 1.35 min; 363.20 (MH)$^+$.

EXAMPLE 74 trans-2-[5-Fluoroindol-3-yl]-1-(piperazin-1-yl-methyl)-cyclopropane

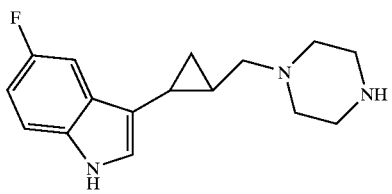

LC-MS: 0.62 min; 274.14 (MH)$^+$.

EXAMPLE 75 trans-1-[4-Benzyl-piperazin-1-yl-methyl]-2-[5-fluoroindol-3-yl]-cyclopropane

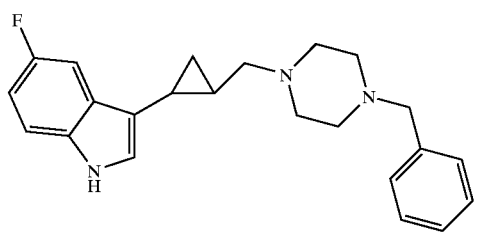

LC-MS: 0.91 min; 364.20 (MH)$^+$.

EXAMPLE 76 trans-1-[1,2,3,4-tetrahydro-1H-isoquinolin-2-yl-methyl]-2-[5-fluoroindol-3-yl]-cyclopropane

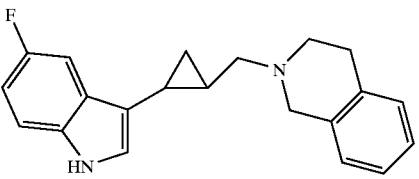

LC-MS: 1.15 min; 321.19 (MH)$^+$.

EXAMPLE 77 trans-1-[N,N-Dipropylaminomethyl]-2-[5-fluoroindol-3-yl]-cyclopropane

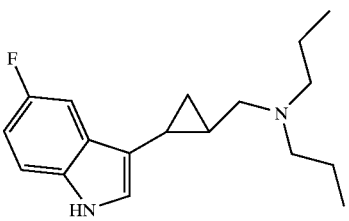

LC-MS: 1.08 min; 289.19 (MH)$^+$.

EXAMPLE 78 trans-2-[5-Fluoroindol-3-yl]-1-[N,N-methyl-phenylethylaminomethyl]-cyclopropane

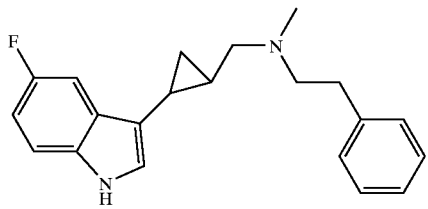

LC-MS: 1.22 min; 323.21 (MH)+.

EXAMPLE 79 trans-2-[5-Fluoroindol-3-yl]-1-[N-phenylethylamino]-cyclopropane

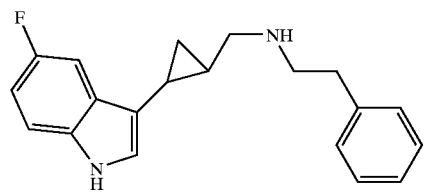

LC-MS: 1.22 min; 309.18 (MH)+.

EXAMPLE 80 trans-2-[5-Fluoroindol-3-yl]-1-[N-2-(2-methoxyphenyl)ethylamino]-cyclopropane

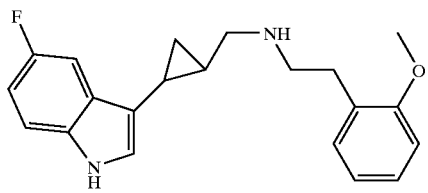

LC-MS: 1.30 min; 339.19 (MH)+.

EXAMPLE 81 trans-2-[5-Fluoroindol-3-yl]-1-[N-2-(3-methoxyphenyl)ethylamino]-cyclopropane

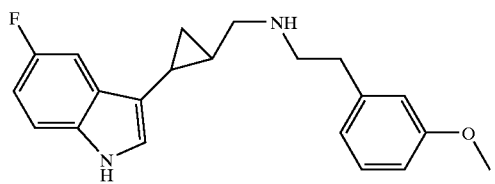

LC-MS: 1.25 min; 339.19 (MH)+.

EXAMPLE 82 trans-2-[5-Fluoroindol-3-yl]-1-[N-2-(4-methoxyphenyl)ethylamino]-cyclopropane

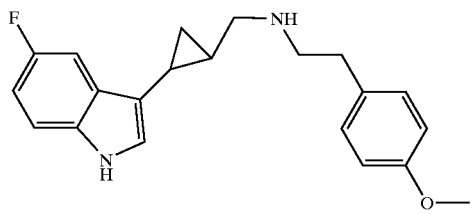

LC-MS: 1.24 min; 339.20 (MH)+.

EXAMPLE 83 trans-2-[5-Fluoroindol-3-yl]-1-[N-2-phenoxy-ethylamino]-cyclopropane

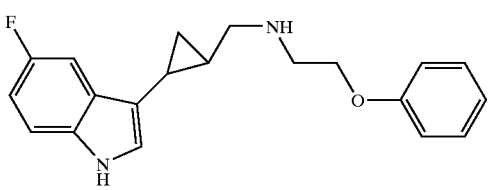

LC-MS: 1.24 min; 325.19 (MH)+.

EXAMPLE 84 trans-2-[5-Fluoroindol-3-yl]-1-[pyrrolidin-1-yl-methyl]-cyclopropane

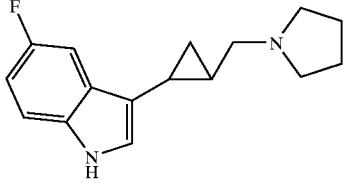

LC-MS: 0.89 min; 259.12 (MH)+.

EXAMPLE 85 trans-2-[5-Fluoroindol-3-yl]-1-[piperidin-1-yl-methyl]-cyclopropane

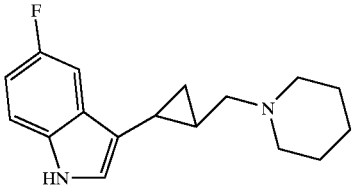

LC-MS: 0.95 min; 273.14 (MH)+.

EXAMPLE 86 trans-1-[N,N-Diethylamino]-2-[5-fluoroindol-3-yl]-cyclopropane

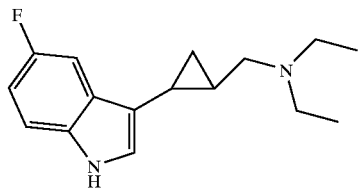

LC-MS: 0.94 min; 261.14 (MH)⁺.

EXAMPLE 87 trans-2-[5-Cyanoindol-3-yl]-1-[N,N-methyl-2-amino(ethylcarbamoyl)ethylaminomethyl]-cyclopropane

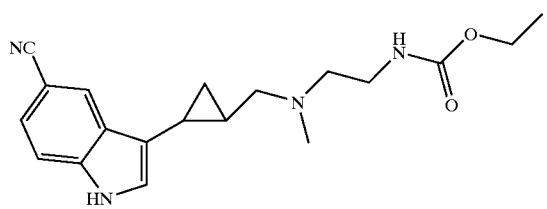

LC-MS: 0.99 min; 341.42 (MH)⁺.

EXAMPLE 88 trans-2-[5-Cyanoindol-3-yl]-1-[N,N-methyl-2-amino(propylcarbamoyl)ethylaminomethyl]-cyclopropane

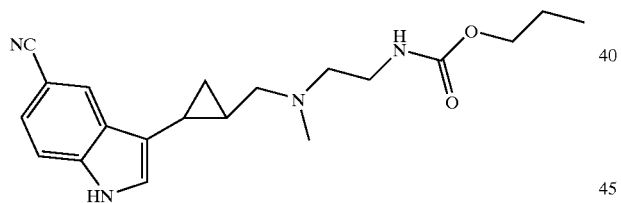

LC-MS: 1.11 min; 355.28 (MH)⁺.

EXAMPLE 89 trans-2-[5-Cyanoindol-3-yl]-1-[N,N-methyl-2-amino(methylcarbamoyl)propylaminomethyl]-cyclopropane

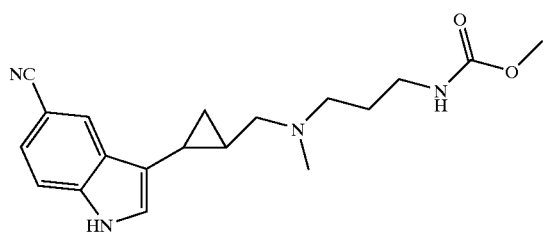

LC-MS: 0.91 min; 341.27 (MH)⁺.

EXAMPLE 90 trans-2-[5-Cyanoindol-3-yl]-1-[N,N-methyl-2-amino(ethylcarbamoyl)propylaminomethyl]-cyclopropane

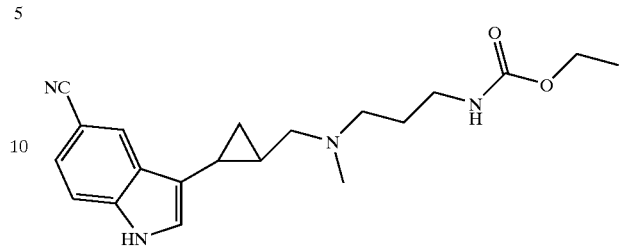

LC-MS: 1.01 min; 355.40 (MH)⁺.

EXAMPLE 91 trans-2-[5-Cyanoindol-3-yl]-1-[N,N-methyl-2-amino(propylcarbamoyl)propylaminomethyl]-cyclopropane

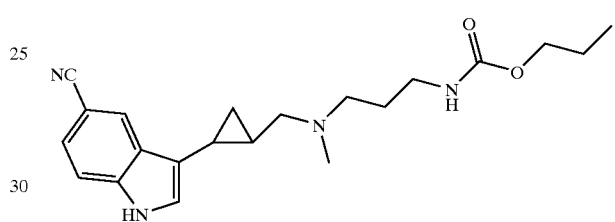

LC-MS: 1.11 min; 369.29 (MH)⁺.

EXAMPLE 92 trans-2-[5-Cyanoindol-3-yl]-1-[N,N-methyl-2-amino(isopropylcarbamoyl)propylaminomethyl]-cyclopropane

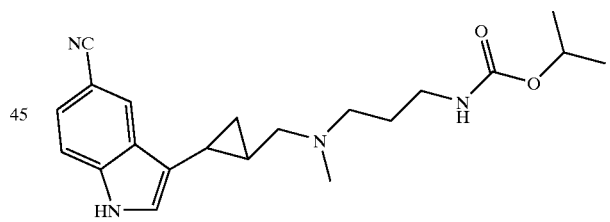

LC-MS: 1.10 min; 369.29 (MH)⁺.

EXAMPLE 93 trans-2-[5-Cyanoindol-3-yl]-1-[N,N-ethyl-2-amino(methylcarbamoyl)ethylaminomethyl]-cyclopropane

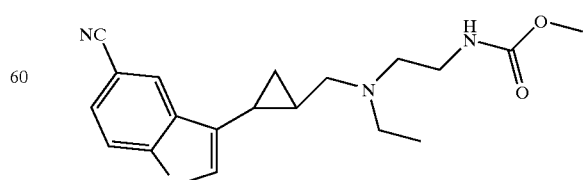

LC-MS: 0.93 min; 341.38 (MH)⁺.

EXAMPLE 94 trans-2-[5-Cyanoindol-3-yl]-1-[N,N-ethyl-2-amino(ethylcarbamoyl)ethylaminomethyl]-cyclopropane

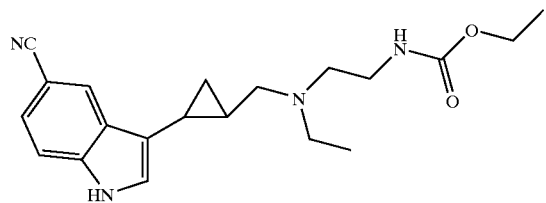

LC-MS: 1.03 min; 355.40 (MH)$^+$.

EXAMPLE 95 trans-2-[5-Cyanoindol-3-yl]-1-[N,N-ethyl-2-amino(propylcarbamoyl)ethylaminomethyl]-cyclopropane

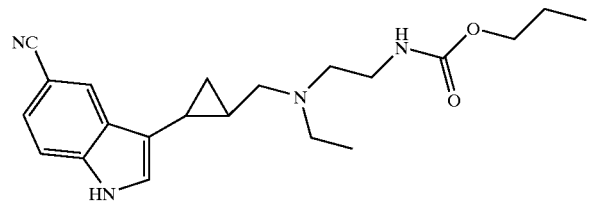

LC-MS: 1.36 min; 369.42 (MH)$^+$.

EXAMPLE 96 trans-2-[5-Cyanoindol-3-yl]-1-[N,N-ethyl-2-amino(isopropylcarbamoyl)ethylaminomethyl]-cyclopropane

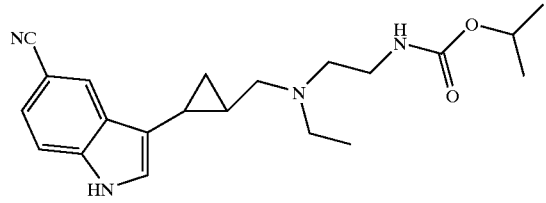

LC-MS: 1.36 min; 369.39 (MH)$^+$.

EXAMPLE 97 trans-2-[5-Cyanoindol-3-yl]-1-[N,N-ethyl-2-amino(methylcarbamoyl)propylaminomethyl]-cyclopropane

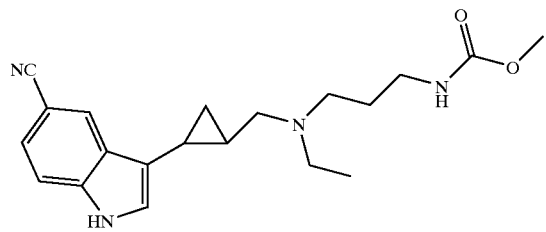

LC-MS: 1.01 min; 355.21 (MH)$^+$.

EXAMPLE 98 trans-2-[5-Cyanoindol-3-yl]-1-[N,N-ethyl-2-amino(ethylcarbamoyl)propylaminomethyl]-cyclopropane

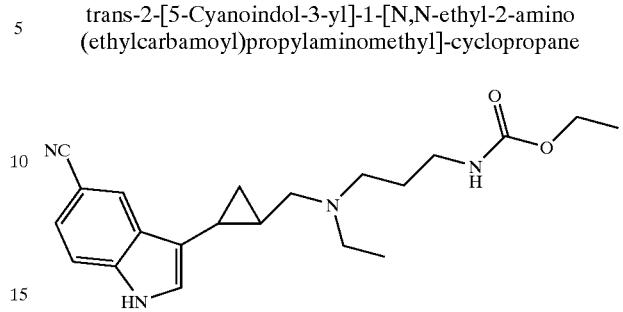

LC-MS: 1.08 min; 369.21 (MH)$^+$.

EXAMPLE 99 trans-2-[5-Cyanoindol-3-yl]-1-[N,N-ethyl-2-amino(propylcarbamoyl)propylaminomethyl]-cyclopropane

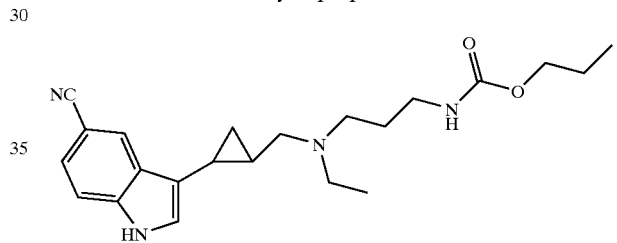

LC-MS: 1.35 min; 383.43 (MH)$^+$.

EXAMPLE 100 trans-2-[5-Cyanoindol-3-yl]-1-[N,N-ethyl-2-amino(isopropylcarbamoyl)propylaniinomethyl]-cyclopropane

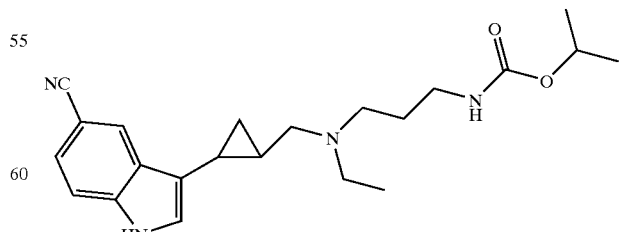

LC-MS: 1.36 min; 383.41 (MH)$^+$.

EXAMPLE 101 trans-2-[5-Fluoroindol-3-yl]-1-[N,N-methyl-2-amino(ethylcarbamoyl)ethylaminomethyl]-cyclopropane

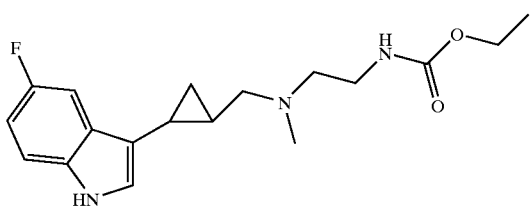

LC-MS: 1.29 min; 334.39 (MH)$^+$.

EXAMPLE 102 trans-2-[5-Fluoroindol-3-yl]-1-[N,N-methyl-2-amino(propylcarbamoyl)ethylaminomethyl]-cyclopropane

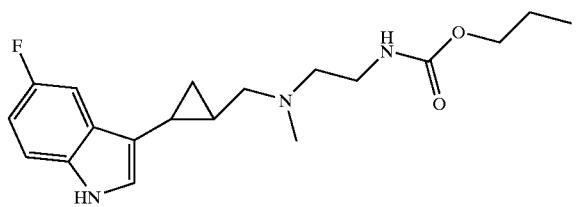

LC-MS: 1.46 min; 348.43 (MH)$^+$.

EXAMPLE 103 trans-2-[5-Fluoroindol-3-yl]-1-[N,N-methyl-2-amino(isopropylcarbamoyl)ethylaminomethyl]-cyclopropane

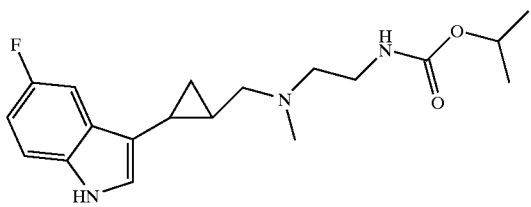

LC-MS: 1.42 min; 348.42 (MH)$^+$.

EXAMPLE 104 trans-2-[5-Fluoroindol-3-yl]-1-[N,N-methyl-2-amino(methylcarbamoyl)propylaminomethyl]-cyclopropane

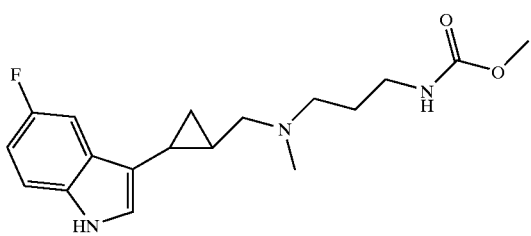

LC-MS: 1.20 min; 334.42 (MH)$^+$.

EXAMPLE 105 trans-2-[5-Fluoroindol-3-yl]-1-[N,N-methyl-2-amino(ethylcarbamoyl)propylaminomethyl]-cyclopropane

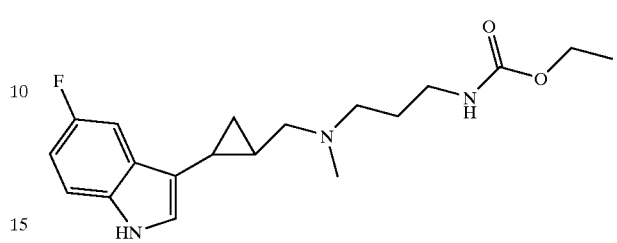

LC-MS: 1.33 min; 348.40 (MH)$^+$.

EXAMPLE 106 trans-2-[5-Fluoroindol-3-yl]-1-[N,N-methyl-2-amino(propylcarbamoyl)propylaminomethyl]-cyclopropane

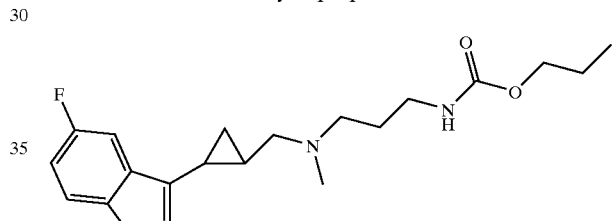

LC-MS: 1.46 min; 362.44 (MH)$^+$.

EXAMPLE 107 trans-2-[5-Fluoroindol-3-yl]-1-[N,N-methyl-2-amino(isopropylcarbamoyl)propylaminomethyl]-cyclopropane

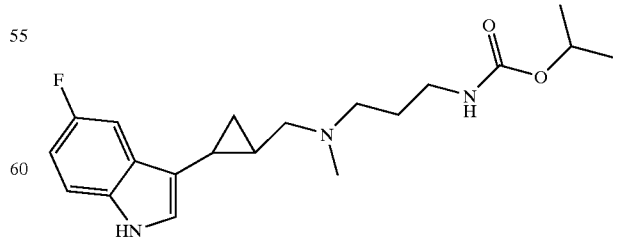

LC-MS: 1.44 min; 362.44 (MH)$^+$.

EXAMPLE 108 trans-1-[N,N-Ethyl-2-amino(methylcarbamoyl)ethylaminomethyl]-2-[5-fluoroindol-3-yl]-cyclopropane

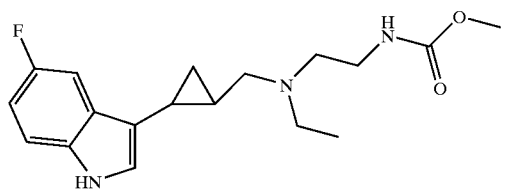

LC-MS: 1.22 min; 334.37 (MH)+.

EXAMPLE 109 trans-1-[N,N-Ethyl-2-amino(ethylcarbamoyl)ethylaminomethyl]-2-[5-fluoroindol-3-yl]-cyclopropane

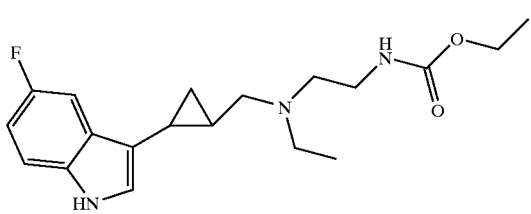

LC-MS: 1.17 min; 348.20 (MH)+.

EXAMPLE 110 trans-1-[N,N-Ethyl-2-amino(propylcarbamoyl)ethylaminomethyl]-2-[5-fluoroindol-3-yl]-cyclopropane

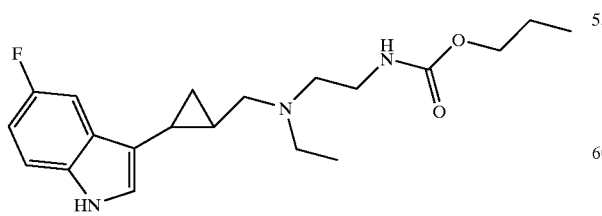

LC-MS: 1.51 min; 362.40 (MH)+.

EXAMPLE 111 trans-1-[N,N-Ethyl-2-amino(isopropylcarbamoyl)ethylaminomethyl]-2-[5-fluoroindol-3-yl]-cyclopropane

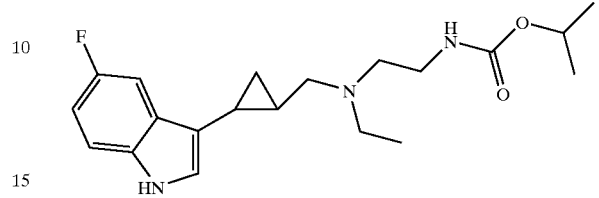

LC-MS: 1.28 min; 362.21 (MH)+.

EXAMPLE 112 trans-1-[N,N-Ethyl-2-amino(methylcarbamoyl)propylaminomethyl]-2-[5-fluoroindol-3-yl]-cyclopropane

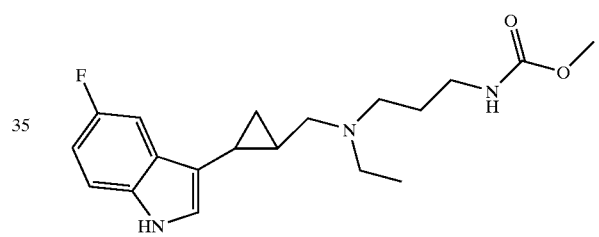

LC-MS: 1.08 min; 348.19 (MH)+.

EXAMPLE 113 trans-1-[N,N-Ethyl-2-amino(ethylcarbamoyl)propylaminomethyl]-2-[5-fluoroindol-3-yl]-cyclopropane

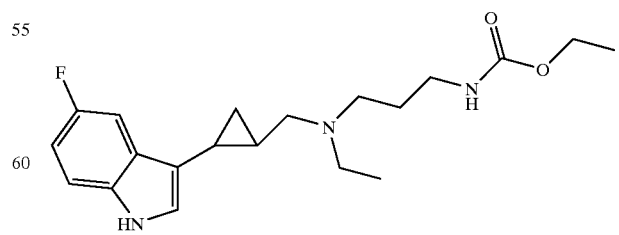

LC-MS: 1.17 min; 362.21 (MH)+.

EXAMPLE 114 trans-1-[N,N-Ethyl-2-amino(propylcarbamoyl) propylaminomethyl]-2-[5-fluoroindol-3-yl]-cyclopropane

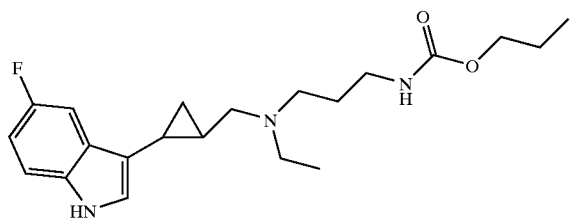

LC-MS: 1.49 min; 376.40 (MH)+.

EXAMPLE 115 trans-1-[N,N-Ethyl-2-amino(isopropylcarbamoyl) propylaminomethyl]-2-[5-fluoroindol-3-yl]-cyclopropane

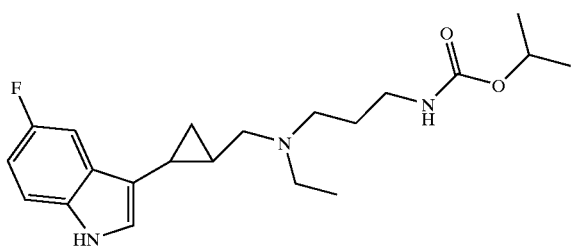

LC-MS: 1.47 min; 376.44 (MH)+.

EXAMPLE 117

Cis-2-[5-Cyanoindol-3-yl]-1-(N,N-dimethylaminomethyl)cyclopropane

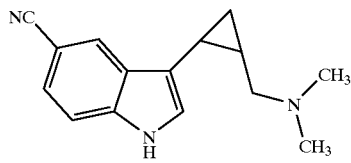

A solution of bis(2,2,2-trifluoroethyl)(methoxycarbonylmethyl)phosphonate (470 µL, 2.2 mmol) in anhydrous tetrahydrofuran (5 ml) was added to a stirred suspension of oil free sodium hydride (89 mg, 2.2 mmol) in anhydrous tetrahydrofuran (25 ml) maintained at 0° C. The reaction was warmed to room temperature and was stirred for 1.5 h. After cooling to 0° C., [5-cyano-1-(p-toluenesulfonyl)indol-3-yl]carboxaldehyde (600 mg, 1.85 mmol) was added. The resulting mixture was stirred at room temperature for 5 hr. The solvent was evaporated and the residue taken up in brine (20 ml) and extracted with ethyl acetate (3×10 ml). The organic layers were dried with anhydrous magnesium sulfate and the solvent removed in vacuo. The product was purified by silica gel column chromatogrpahy with 15% ethyl acetate in hexanes to give 192 mg (27% yield) of methyl (Z)-3-[5-Cyano-1-(p-toluenesulfonyl)indol-3-yl]-acrylate: $^1$H NMR (300 MHz, CDCl3): δ 9.08 (1H, s), 8.10 (1H, d, J=8.3 Hz), 7.92 (1H, d, J=1.0 Hz), 7.86 (2H, d, J=8.4 Hz), 7.59 (1H, dd, J=8.6, 1.5 Hz), 7.29 (2H, d, J=8.1 Hz), 6.98 (1H, d, J=13.0 Hz), 6.08 (1H, d, J=12.6 Hz), 3.80 (3H, s), 2.37 (3H, s); MS m/e 395.1 (M+H)+.

The following procedure was carried out behind a safety shield using plastic coated glassware free of scratches and ground glass joints. 1-Methyl-3-nitro-1-nitrosoguanidine (850 mg, 5.8 mmol) was carefully added portionwise over 10 min to a Erlenmeyer flask containing a swirled mixture of aqueous sodium hydroxide (100 ml, 5 N) and diethyl ether (50 ml) at 0° C. After vigorous bubbling had ceased, the organic layer (containing diazomethane) was decanted into a chilled (0° C.) Erlenmeyer flask containing potassium hydroxide chips (2 g). The mixture was swirled for 10 min and the yellow solution was decanted into a dropping funnel. The solution of diazomethane was added over 10 min to an open flask containing a stirred mixture of methyl (Z)-3-[5-Cyano-1-(p-toluenesulfonyl)indol-3-yl]-acrylate (220 mg, 0.58 mmol) and palladium acetate (7 mg, 0.029 mmol) in dichloromethane (50 ml) maintained at 0° C. After stirring for 30 min, the reaction was quenched with glacial acetic acid (2 ml) and poured into aqueous sodium hydroxide (0.5 N, 40 ml). The aqueous layer was extracted with ethyl acetate (3×10 ml). The organic layers were dried over anhydrous magnesium sulfate, and concentrated in vacuo. The product was purified by silica gel column chromatography with 15% ethyl acetate in hexanes to afford 187 mg (82% yield) of methyl [cis-2-[5-Cyano-1-(p-toluenesulfonyl)indol-3-yl]cycloprop-1-yl]-acrylate: $^1$H NMR (400 MHz, CDCl3): δ 7.98 (1H, d, J=8.7 Hz), 7.89 (1H, s), 7.73 (2H, d, J=6.7 Hz), 7.52 (2H, m), 7.24 (2H, d, J=8.0 Hz), 3.34 (3H, s), 2.38 (1H, m), 2.34 (3H, s), 2.22 (1H, m), 1.61 (1H, m), 1.25 (1H, m); MS m/e 473.2 (M+H)+.

Powdered lithium aluminum hydride (120 mg, 3.16 mmol) was carefully added to a stirred solution of methyl [cis-2-[5-Cyano-1-(p-toluenesulfonyl)indol-3-yl]cycloprop-1-yl]-acrylate (185 mg, 0.47 mmol) in anhydrous tetrahydrofuran (10 ml) at −30° C. The resulting mixture was stirred at −20° C. for 1.5 h. The reaction was quenched with ethyl acetate (5 ml) and allowed to warmed to room temperature. After 10 min, water (120 µL) was added and after 5 min followed by a solution of aqueous sodium hydroxide (1N, 360 µL). After a further 5 min water (120 ml) was added and the solution was stirred 20 min. The aluminum salts were removed by vacuum filtration. The salts were rinsed with ethyl acetate (100 ml) and the combined filtrates were concentrated in vacuo. The crude material was purified by silica gel column chromatography with 45% ethyl acetate in hexanes to afford 131 mg (76% yield) of cis-2-[5-Cyano-1-(p-toluenesulfonyl)indol-3-yl]cyclopropanemethanol as a white solid: $^1$H NMR (400 MHz, CDCl3): δ 8.04 (1H, d, J=8.6 Hz), 7.99 (1H, d, J=1.0 Hz), 7.74 (2H, d, J=6.8 Hz), 7.57 (1H, dd, J=8.6, 1.6 Hz), 7.44 (1H, d, J=1.3 Hz), 7.26 (2H, d, J=8.2 Hz), 3.50 (1H, m), 3.16 (1H, m), 2.36 (3H, s), 2.05 (1H, m), 1.60 (1H, m), 1.19 (1H, m), 0.99 (1H, t, J=5.5 Hz), 0.72 (1H, q, J=5.6 Hz); MS m/e 349 (M−OH)−.

To a −78° C. solution of oxalyl chloride (52 µL, 0.60 mmol) in anhydrous dichloromethane (20 ml) was added dimethylsulfoxide (50 µL, 0.70 mmol) dropwise. After stirring 10 min, a solution of cis-2-[5-Cyano-1-(p- toluenesulfonyl)indol-3-yl]cyclopropanemethanol (129 mg, 0.35 mmol) in dichloromethane (5 ml) was added dropwise. After stirring 20 min at −78° C., triethylamine (294 □L, 2.10 mmol) was added dropwise. The reaction was stirred for 5 min at −78° C. and then allowed to warm to room temperature. The reaction was washed with water (2×5 ml), dried with anhydrous magnesium sulfate and the solvent was evaporated to give the crude cis-2-[5-Cyano-1-(p-toluenesulfonyl)indol-3-yl]cyclopropanecarboxaldehyde.

A mixture of the crude cis-2-[5-Cyano-1-(p-toluenesulfonyl)indol-3-yl]cyclopropanecarboxaldehyde, dimethylamine (0.35 ml, 0.7 mmol, 2.0 M/THF), and anhydrous ethanol (10 ml) was heated with stirring until all solids were dissolved. The reaction vessel was removed from the heating source and sodium triacetoxyborohydride (300 mg, 1.41 mmol) was added. After stirring for 1 h, the solvent was evaporated. The residue was taken up in brine (10 ml) and aqueous 1N sodium hydroxide was added until solids disappeared. The aqueous layer was extracted with ethyl acetate ((4×10 ml), dried over anhydrous magnesium sulfate, and concentrated in vacuo to give the crude cis-2-[5-cyano-1-(p-toluenesulfonyl)indol-3-yl]-1-(N,N-dimethylaminomethyl)cyclopropane.

Water (4 ml) and an aqueous solution of sodium hydroxide (2 ml, 10 N) were sequentially added to a flask charged with a solution of crude cis-2-[5-cyano-1-(p-toluenesulfonyl)indol-3-yl]-1-(N,N-dimethylaminomethyl) cyclo-propane dissolved in anhydrous ethanol (15 ml). The resulting mixture was heated at 70° C. for 1 h. The solvent was evaporated and the residue was taken up in brine (10 ml). The aqueous layer was extracted with 10% methanol/ethyl acetate (3×5 ml). The combined organic layers were dried over anhydrous magnesium sulfate and concentrated in vacuo. The crude material was purified by silica gel column chromatography and eluted using a step gradient of a solvent mixture [chloroform/(2 M ammonia/methanol), 90/10, 80/20]. The cis-2-[5-cyanoindol-3-yl]-1-(N,N-dimethylaminomethyl)cyclopropane was obtained as a white solid (63 mg, 75% yield over 3 steps): $^1$H NMR (400 MHz, CDCl$_3$): δ 8.47 (1H, br s), 8.07 (1H, s), 7.41 (2H, apparent q, J=8.0 Hz), 7.03 (1H, s), 2.37 (1H, dd, J=12.6, 4.7 Hz), 2.18 (6H, s), 1.97 (1H, m), 1.69 (1H, dd, J=12.6, 8.6 Hz), 1.34 (1H, m), 1.22 (1H, m), 0.71 (1H, q, J=5.0 Hz); MS m/e 240 (M+H)$^+$.

EXAMPLE 118

Cis-2-[5-Fluoroindol-3-yl]-1-(N,N-dimethylaminomethyl)cyclopropane

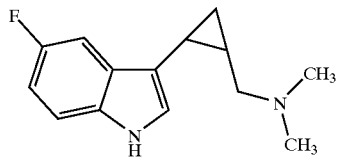

Cis-2-[5-fluoroindol-3-yl]-1-(N,N-dimethylaminomethyl)cyclopropane was prepared in a similar manner: $^1$H NMR (400 MHz, CDCl$_3$): δ 8.30 (1H, br s), 7.34 (1H, dd, J=9.6, 2.5 Hz), 7.24 (1H, dd, J=8.8, 4.4 Hz), 6.93 (2H, m), 2.42 (1H, dd, J=12.6, 4.8 Hz), 2.18 (6H, s), 2.03 (1H, m), 1.70 (1H, dd, J=12.6, 8.7 Hz), 1.27 (1H, m,) 1.18 (1H, m), 0.67 (1H, q, J=4.8 Hz); MS m/e 233 (M+H)$^+$.

EXAMPLE 119 trans-2-[5-Cyanoindol-3-yl]-1-(N-methylaminomethyl)cyclopropane

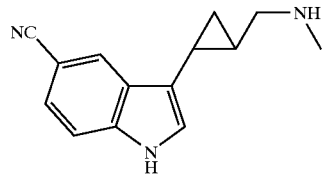

Racemic trans-2-[5-cyanoindol-3-yl]-1-(N-methylaminomethyl)cyclopropane was prepared in two steps and 67% overall yield from racemic (trans)-2-[5-cyano-1-(p-toluenesulfonyl)indol-3-yl]cyclopropanecarboxaldehyde following the procedures outlined for the preparation of (1S,2S)-trans-2-[5-cyanoindol-3-yl]-1-(N-methylaminomethyl)cyclopropane: LC-MS (column=YMC ODS-A C18 S7, 3×50 mm, start % B=0, final % B=100, gradient time=2 min, flow rate=5 ml/min) m/e 226 (M+H)$^+$, $t_R$ 0.80 min.

EXAMPLE 120

(1S,2S)-trans-2-[5-Cyanoindol-3-yl]-1-(N-methylaminomethyl)cyclopropane

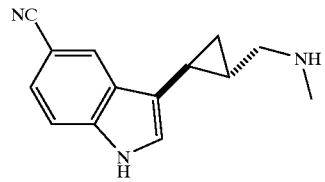

A mixture of (1S,2S)-(trans)-2-[5-cyano-1-(p-toluenesulfonyl)indol-3-yl]cyclopropanecarboxaldehyde (0.500 g, 1.37 mmol), methylamine (2.0 M/THF, 13.7 ml, 27.4 mmol, 20 equiv), acetic acid (1.57 ml, 27.4 mmol, 20 equiv) and anhydrous ethanol (20 ml) were heated to with stirring until all solids were dissolved (10 min). After cooling to rt, sodium triacetoxyborohydride (0.871 g, 4.11 mmol, 3 equiv) was added. The mixture was heated with stirring at 70° C. for 1 h. The reaction contents were poured into aqueous solution of sodium hydroxide (1 M, 150 ml). The aqueous layer was extracted with ethyl acetate (3×100 ml). The combined organic extracts were washed with brine (50 ml), dried over anhydrous magnesium sulfate, filtered, and concentrated in vacuo. The crude product was purified using silica gel column chromatography (90:10:2, CHCl$_3$/MeOH/Et$_3$N) to provide 460 mg (89% yield) of 3-[2-(1-dimethylamino-ethyl)-cyclopropyl]-1H-indole-5-carbonitrile: LC-MS (column=Phenomenex Luna C18 S10, 3×50 mm, start % B=0, final % B=100, gradient time=3 min, flow rate=4 ml/min) m/e 380 (M+H)$^+$, $t_R$ 1.92 min.

Water (1.5 ml) and an aqueous solution of sodium hydroxide (0.6 ml, 10 N) were sequentially added to a flask charged with a solution of (1S,2S)-trans-2-[5-cyano-1-(p-toluenesulfonyl)indol-3-yl]-1-(N-methylaminomethyl) cyclopropane dissolved in anhydrous ethanol (15 ml). The resulting mixture was heated at 70° C. for 45 min. The reaction contents were poured into aqueous solution of sodium hydroxide (1 M, 50 ml) and brine (50 ml). The aqueous layer was extracted with 10% methanolic ethyl acetate (2×100 ml). The combined organic extracts were washed with brine (50 ml), dried over anhydrous magnesium sulfate, filtered, and concentrated in vacuo. The crude product was purified using silica gel column chromatography using a step gradient (90:10:2, 82:15:2, CHCl$_3$/MeOH/Et$_3$N) to provide 204 mg (75% yield) (1S,2S)-trans-2-[5-cyanoindol-3-yl]-1-(N-methylaminomethyl)cyclopropane: $^1$H NMR (400 MHz, DMSO-d$_6$): δ 11.35 (1H, br s), 8.16 (1H, d, J=0.6 Hz), 7.47 (1H, d, J=6.8 Hz), 7.40 (1H, dd, J=6.7, 1.2 Hz), 7.21 (1H, s), 2.50 (2H, m), 2.34 (3H, s), 1.81 (1H, m), 1.10 (1H, m), 0.87 (1H, m), 0.76 (1H, m); LC-MS (column=Phenomenex Luna C18 S10, 3×50 mm, start % B=0, final % B=100, gradient time=4 min, flow rate=4 ml/min) m/e 226 (M+H)$^+$, t$_R$ 1.13.

EXAMPLE 121 trans-3-[2-(1-Dimethylamino-ethyl)-cyclopropyl]-1H-indole-5-carbonitrile

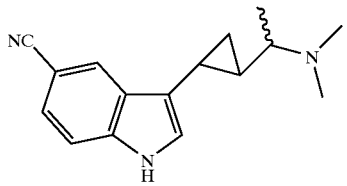

(Diastereomeric Mixture)

A solution of methylmagnesium bromide (3.0 M in diethyl ether, 0.826 ml, 2.48 mmol, 1.05 equiv) was added to a suspension of [trans-2-[5-cyano-1-(p-toluenesulfonyl)indol-3-yl]cycloprop-1-yl]-N-methoxy-N-methylcarboxamide (1 g, 2.36 mmol) in anhydrous diethyl ether (25 ml). The resulting mixture was stirred at 0° C. for 2 h. The reaction mixture was diluted anhydrous THF (15 ml) and stirred for an additional 3 h at 0° C. The cold mixture was quenched with aqueous 1 M hydrochloric acid (200 ml) and extracted with ethyl acetate (3×100 ml). The combined organic extracts were washed with brine (50 ml), dried over anhydrous magnesium sulfate, filtered, and concentrated. The crude reaction mixture was purified by silica gel column chromatography using a step gradient [2:1, 1:1 (hexanes/ethyl acetate)] to afford 0.518 g (58% yield) of trans-3-(2-acetyl-cyclopropyl)-1-(toluene-4-sulfonyl)-1H-indole-5-carbonitrile as a white solid: LC-MS (column=Phenomenex Luna C18 S10, 3×50 mm, start % B=0, final % B=100, gradient time=2 min, flow rate=5 ml/min) m/e 379 (M+H)$^+$, t$_R$ 2.45 min.

Sodium cyanoborohydride (51 mg, 0.792 mmol, 3 equiv) was added to a stirred mixture of trans-3-(2-acetyl-cyclopropyl)-1-(toluene-4-sulfonyl)-1H-indole-5-carbonitrile (100 mg, 0.264 mmol), dimethylamine (2.0 M in THF, 2.64 ml, 5.28 mmol, 20 equiv), acetic acid (302 uL, 5.28 mmol, 20 equiv) and powdered 4 A molecular sieves (150 mg, actived) in 2-propanol (2.0 ml). The resulting mixture was stirred at 50° C. for 20 h. Ethanol (5 ml), water (0.5 ml), and a solution of sodium hydroxide (10 M in water, 0.6 ml) were added to the reaction. The mixture was heated with stirring at 50° C. for 1 h. The reaction contents were poured into an aqueous solution of sodium hydroxide (1 M, 25 ml) and brine (25 ml). The aqueous layer was extracted with ethyl acetate (3×100 ml). The combined organic extracts were washed with brine (20 ml), dried over anhydrous magnesium sulfate, filtered, and concentrated in vacuo. The crude product was purified using silica gel column chromatography (90:10:1, CHCl$_3$/MeOH/Et$_3$N) to provide 67 mg (100% yield) of 3-[2-(1-dimethylamino-ethyl)-cyclopropyl]-1H-indole-5-carbonitrile as a 1:1 mixture of diastereomers. viscous oil: LC-MS (column=Phenomenex Luna C18 S10, 3×50 mm, start % B=0, final % B=100, gradient time=3 min, flow rate=4 ml/min) m/e 254 (M+H)$^+$, t$_R$ 1.19 min.

EXAMPLE 122

Separation of the diasteromers of trans-3-[2-(1-Dimethylamino-ethyl)-cyclopropyl]-1H-indole-5-carbonitrile

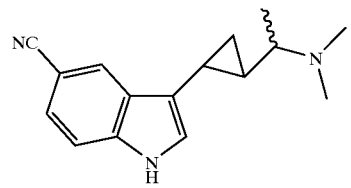

The two diastereomers were separated using reverse phase preparatory HPLC (column: YMC S5 ODS, 30×100 mm). The relative stereochemistry for the individual diastereomers was not determined.

EXAMPLE 122A

Analytical data for diastereomer A: $^1$H NMR (400 MHz, DMSO): δ 11.48 (1H, br s), 8.15 (1H, d, J=0.6 Hz), 7.51 (1H, dd, J=8.4, 0.4 Hz), 7.43 (1H, dd, J=8.5, 1.5 Hz), 7.32 (1H, d, J=2.2 Hz), 3.01 (1H, m), 2.80 (3H, s), 2.79 (3H, s), 2.05 (1H, m), 1.42 (3H, d, J=6.7 Hz), 1.22 (3H, m); LC-MS (column=Phenomenex Luna C18 S10, 3×50 mm, start % B=0, final % B=100, gradient time=2 min, flow rate=5 ml/min) m/e 254 (M+H)$^+$, t$_R$ 0.84 min.

EXAMPLE 122B

Analytical data for diastereomer B: $^1$H NMR (400 MHz, DMSO) 11.48 (1H, br s), 8.19 (1H, m), 7.50 (1H, dd, J=8.4, 0.4 Hz), 7.43 (1H, dd, J=8.4, 1.5 Hz), 7.33 (1H, d, J=2.2 Hz), 3.05 (1H, m), 2.80 (3H, s), 2.79 (3H, s), 2.28 (1H, m), 1.36 (1H, m), 1.34 (3H, d, J=6.7 Hz), 1.08 (1H, m), 0.97 (1H, m); LC-MS (column=Phenomenex Luna C18 S10, 3×50 mm, start % B=0, final % B=100, gradient time=2 min, flow rate=5 ml/min) m/e 254 (M+H)$^+$, t$_R$ 0.87 min.

EXAMPLE 123 trans-3-[2-(1-Diethylamino-ethyl)-cyclopropyl]-1H-indole-5-carbonitrile

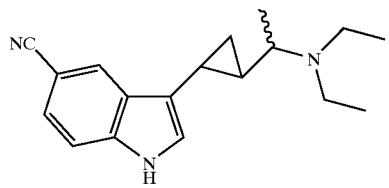

(Diastereomeric Mixture)

Analytical data for trans-3-[2-(1-diethylamino-ethyl)-cyclopropyl]-1H-indole-5-carbonitrile: LC-MS (column=Phenomenex Luna C18 S10, 3×50 mm, start % B=0, final % B=100, gradient time=3 min, flow rate=4 ml/min) m/e 282 (M+H)$^+$, t$_R$ 1.28 min.

EXAMPLE 124 trans-3-[2-(1-Pyrrolidin-1-yl-ethyl)-cyclopropyl]-1H-indole-5-carbonitrile

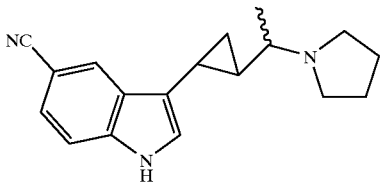

(Diastereomeric Mixture)

Analytical data for trans-3-[2-(1-pyrrolidin-1-yl-ethyl)-cyclopropyl]-1H-indole-5-carbonitrile: LC-MS (column=Phenomenex Luna C18 S10, 3×50 mm, start % B=0, final % B=100, gradient time=3 min, flow rate=4 ml/min) m/e 280 (M+H)$^+$, $t_R$ 1.26 min.

EXAMPLE 125 trans-3-[2-(1-Methylamino-ethyl)-cyclopropyl]-1H-indole-5-carbonitrile

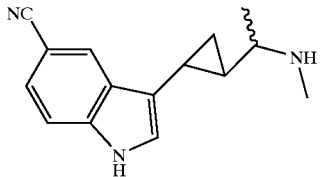

(Diastereomeric Mixture)

Analytical data for trans-3-[2-(1-methylamino-ethyl)-cyclopropyl]-1H-indole-5-carbonitrile: LC-MS (column=Phenomenex Luna C18 S10, 3×50 mm, start % B=0, final % B=100, gradient time=3 min, flow rate=4 ml/min) m/e 240 (M+H)$^+$, $t_R$ 1.15, 1.23 min.

EXAMPLE 126 trans-3-[2-(1-Ethylamino-ethyl)-cyclopropyl]-1H-indole-5-carbonitrile

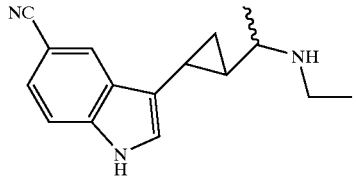

(Diastereomeric Mixture)

Analytical data for trans-3-[2-(1-ethylamino-ethyl)-cyclopropyl]-1H-indole5-carbonitrile: LC-MS (column=Phenomenex Luna C18 S10, 3×50 mm, start % B=0, final % B=100, gradient time=3 min, flow rate=4 ml/min) m/e 254 (M+H)$^+$, $t_R$ 1.24 min.

Preparative Chiral HPLC Resolution of Racemic Indole-Cyclopropanes

The racemates were separated into their corresponding enantiomers on a 50×500 mm Chiralpak AD column using an eluent mixture of ethanol and hexane containing diethylamine modifier. With a flow rate of 60 ml/min, separation times were between 65 and 75 min. Injection loads were determined by the combination of compound solubility in 50:50 ethanol/hexane (more hexane if possible), and by the length of baseline separation time between each pair of enantiomers. Maximum loading for a single run with baseline separation was approximately 100–250 mg. The following preparative and analytical HPLC data exemplify these methods:

EXAMPLE 127

Preparative chiral HPLC separation of racemic trans-2-[5-Cyanoindol-3-yl]-1-(N,N-dimethylaminomethyl)cyclopropane Method:
Chiralpak AD column, 50×500 mm with 20 μm packing
Solvents: 10% Ethanol/hexane (0.15% diethyl amine added in hexane as modifier)
Flow: 60 ml/min for 65 min
UV detector at 280 nm
Loop volume: 10 ml
Injection load: 165 mg in 6.5 ml of 1:3 ethanol/hexane

EXAMPLE 127a (1R,2R)-trans-2-[5-Cyanoindol-3-yl]-1-(N,N-dimethylaminomethyl)cyclopropane maleate salt

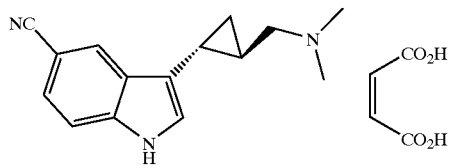

(1R,2R)-trans-2-[5-Cyanoindol-3-yl]-1-(N,N-dimethylaminomethyl)cyclopropane (240 mg) eluted at 29.9 min. 100% purity with >99% ee (Chiralpak AD 4.6×250 mm, 10% methanol, 90% hexane (0.15% diethylamine), 1.0 ml/min, $R_t$=7.62 min). ESI-LRMS: m/z 238.05 (M–H)$^-$. Optical rotation: −17.0 (ethanol, 22 C, c=2.59 mg/ml). This material was converted to the maleate salt: >97% purity (reverse-phase HPLC), >99.5% purity with >99% ee (Chiralpak AD 4.6 mm×250 mm, 10% methanol, 90% hexane (0.15% diethylamine), 1.0 ml/min, $R_t$=7.30 min) ESI-LRMS: m/z 238.04 (M–H)$^-$ Optical rotation: +3.2 (ethanol, 22 C, c=2.54 mg/ml) and −9.9 (water, 22 C, c=3.33 mg/ml). EA calculated for $C_{15}H_{17}N_3.C_4H_4O_4$: C, 64.21; H, 5.96; N, 11.82. Found: C, 63.31; H, 5.94; N, 11.34. $^1$H NMR (DMSO-d6): δ 11.47 (s, 1H), 9.65 (br, 1H), 9.35 (br, 1H) 8.18 (d, 1H, J=0.6 Hz), 7.44 (dd, 2H, J=15.9, 8.4 Hz), 7.32 (d, 1H, J=0.6 Hz), 3.21 (dq, 2H, J=57.0, 7.1, 33.2, 7.1 Hz), 2.84 (s, 6H), 2.10 (q, 1H, J=4.2 Hz), 1.18 (m, 1H), 1.15 (m, 1H) and 1.02 (m, 1H).

A sample of (1R,2R)-trans-2-[5-Cyanoindol-3-yl]-1-(N,N-dimethylamino methyl)cyclopropane maleate salt was enantioselectively synthesized in a manner similar to Example 5 using opposite camphorsultam chiral auxhiliary: Optical rotation: [α]$_D$−10.64 (concentration=7.83 mg/ml, $H_2O$); LC-MS (column=Phenomenex Luna C18 S10, 3×50 mm, start % B=0, final % B=100, gradient time=2 min, flow rate=5 ml/min) m/e 240 (M+H)$^+$, $t_R$ 0.77 min. Anal. calcd. for $C_{19}H_{21}N_3O_4$: C, 64.21; H, 5.95; N, 11.82. Found: C, 64.02; H, 5.83; N, 11.73.

(S,S)-trans-2-[5-Cyanoindol-3-yl]-1-(N,N-dimethylaminomethyl)cyclopropane (230 mg) eluted at 49.0 min and was identical to material enantioselectively synthesized in Example 5.

Total recovery: 240 mg of the (R,R)-enantiomer, 230 mg of the (S,S)-enantiomer; 470 mg of 500 mg submitted (94%). Analytical Chiral HPLC Conditions: Chiralcel AD column, 4.6×250 mm, 10 um; 90% (0.15% DEA) hexane/10% EtOH; 1.0 ml/min for 16 min; Abs.:280 nm

EXAMPLE 128

Preparative chiral HPLC separation of racemic trans-1-(N,N-dimethylaminomethyl)-2-[5-fluoroindol-3-yl]cyclopropane Method:
Chiralpak AD column, 50×500 mm with 20 μm packing
Solvents: 5% Ethanol/hexane (0.15% diethyl amine added in hexane as modifier)
Flow: 60 ml/min for 75 min
UV detector at 280 nm
Loop volume: 10 ml
Injection load: 80 mg in 6.5 ml of 4:5 ethanol/hexane

EXAMPLE 128a (1R,2R)-trans-1-(N,N-dimethylaminomethyl)-2-[5-fluoroindol-3-yl]-cyclopropane maleate salt

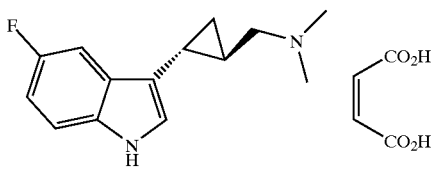

(R,R)-trans-1-(N,N-dimethylaminomethyl)-2-[5-fluoroindol-3-yl]cyclopropane (90 mg) eluted at 47.6 min. 96% purity with >99% ee (Chiralpak AD 4.6×250 mm, 5% methanol, 95% hexane (0.15% diethylamine), 0.5 ml/min, $R_t$=21.57 min). ESI-LRMS: m/z 231.05 (M–H)⁻ Optical rotation: −51.1 (ethanol, 22 C, c=4.64 mg/ml)

A sample of (1R,2R)-trans-1-(N,N-dimethylaminomethyl)-2-[5-fluoroindol-3-yl]-cyclopropane maleate salt was enantioselectively synthesized in a manner similar to Example 4 using opposite camphorsultam chiral auxhiliary: Optical rotation: $[\alpha]_D$ −29.52 (concentration=3.93 mg/ml, $H_2O$). LC-MS (column=Phenomenex Luna C18 S10, 3×50 mm, start % B=0, final % B=100, gradient time=3 min, flow rate=4 ml/min) m/e 233 (M+H)⁺, $t_R$ 1.18 min. Anal. calcd. for $C_{18}H_{21}FN_2O_4$: C, 62.06; H, 6.07; N, 8.04. Found: C, 62.10; H, 6.05; N, 8.02.

(S,S)-trans-1-(N,N-dimethylaminomethyl)-2-[5-fluoroindol-3-yl]cyclopropane (120 mg) eluted at 60.8 min and was identical to material enantioselectively synthesized in Example 4. Total recovery: 90 mg of (R,R)-enantiomer, 120 mg of (S,S)-enantiomer; 210 mg of 231 mg submitted (91%).

EXAMPLE 129

Preparative chiral HPLC resolution of racemic Cis-2-[5-Cyanoindol-3-yl]-1-(N,N-dimethylaminomethyl)cyclopropane

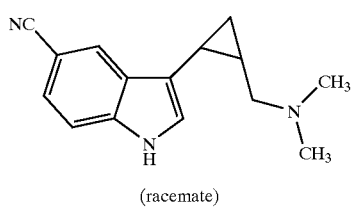

(racemate)

Method:

Chiralpak AD column, 21×250 mm with 20 μm packing
Solvents: 10% Ethanol/hexane (0.15% diethylamine added in hexane as modifier)
Flow: 20 ml/min for 45 min
UV detector at 241 nm
Loop volume: 10 ml
Injection load: 18 mg in 1 ml of 1:3 ethanol/hexane

EXAMPLE 129a

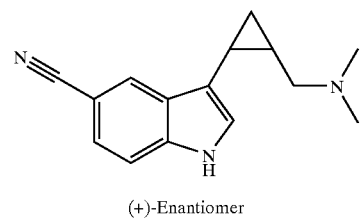

(+)-Enantiomer

The (+)-enantiomer eluted at 21.02 min. >99% purity (reverse-phase HPLC), >97% purity with >99% ee (Chiralpak AD 4.6×250 mm, 10% methanol, 90% hexane (0.15% diethylamine), 1.0 ml/min, $R_t$=8.02 min, sign of rotation determined by laser polarimetry) ESI-LRMS: m/z 237.94 (M–H)⁻

EXAMPLE 129b

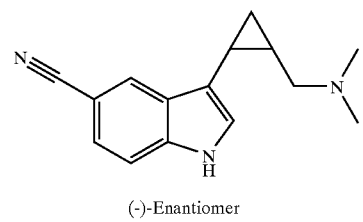

(−)-Enantiomer

The (−)-enantiomer at 34.84 min. >97% purity (reverse-phase HPLC), >98% purity with >99% ee (Chiralpak AD 4.6×250 mm, 10% methanol, 90% hexane (0.15% diethylamine), 1.0 ml/min, $R_t$=10.91 min, sign of rotation determined by laser polarimetry). ESI-LRMS: m/z 237.96 (M–H)⁻.

EXAMPLE 130

Preparative chiral HPLC resolution of racemic Cis-2-[5-Fluoroindol-3-yl]-1-(N,N-dimethylaminomethyl)cyclopropane

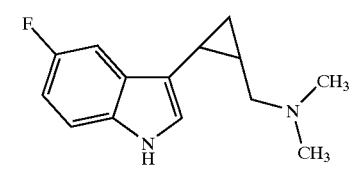

Method:
Chiralpak AD column, 21×250 mm with 20 μm packing
Solvents: 5% Ethanol/hexane (0.15% diethylamine added in hexane as modifier)
Flow: 10 ml/min for 55 min
UV detector at 241 nm
Loop volume: 10 ml
Injection load: 17 mg in 1.1 ml of 1:1 ethanol/hexane

EXAMPLE 130a

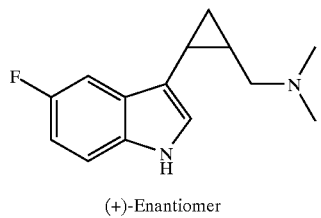

(+)-Enantiomer

The (+)-enantiomer eluted at 23.47 min. >99% purity (reverse-phase HPLC), >94% purity with >99% ee (Chiralpak AD 4.6×250 mm, 5% methanol, 95% hexane (0.15% diethylamine), 10.5 ml/min, $R_t$=20.18 min, sign of rotation determined by laser polarimetry). ESI-LRMS: m/z 230.92 (M–H)⁻.

EXAMPLE 130b

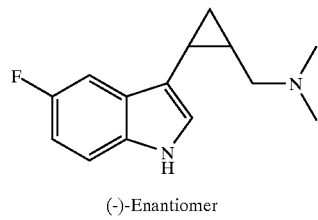

(–)-Enantiomer

The (–)-enantiomer at 39.08 min. >99% purity (reverse-phase HPLC), >96% purity with >99% ee (Chiralpak AD 4.6×250 mm, 5% methanol, 95% hexane (0.15% diethylamine), 0.5 ml/min, $R_t$=30.97 min, sign of rotation determined by laser polarimetry). ESI-LRMS: m/z 230.94 (M–H)⁻.

The following examples were prepared by the methods illustrated above:

| Example | Structure | LC-MS retention time (min)** | LC-MS (MH)+ |
|---|---|---|---|
| 131 | 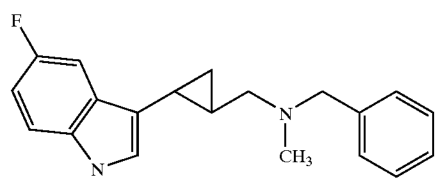 | 1.1 | 309.4 |
| 132 | 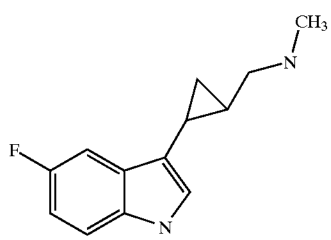 | 0.89 | 219.1 |
| 133 | 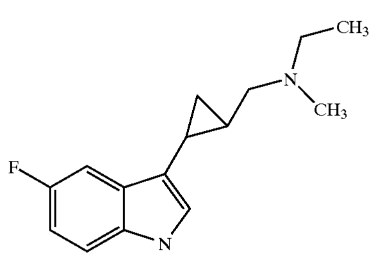 | 0.81 | 247.4 |

-continued

| Example | Structure | LC-MS retention time (min)** | LC-MS (MH)+ |
|---------|-----------|------------------------------|-------------|
| 134 | 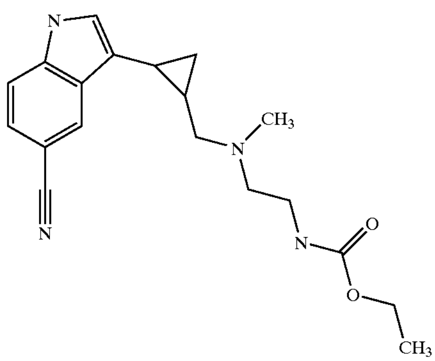 | 0.99 | 341.42 |
| 135 | 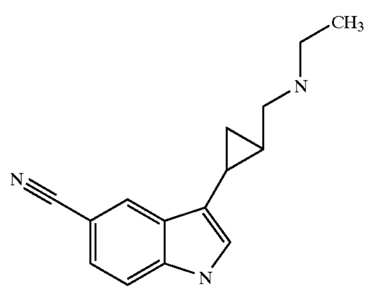 | 0.75 | 240.17 |
| 136 | 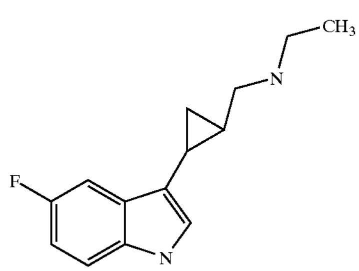 | 0.84 | 233.18 |
| 137 | 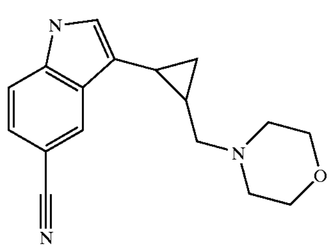 | 0.76 | 282.16 |
| 138 | 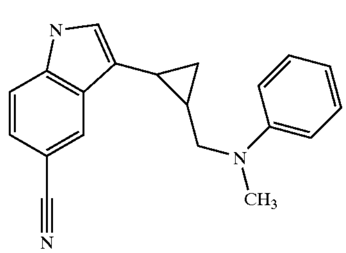 | 1.04 | 302.17 |

-continued
| Example | Structure | LC-MS retention time (min)** | LC-MS (MH)+ |
|---|---|---|---|
| 139 | 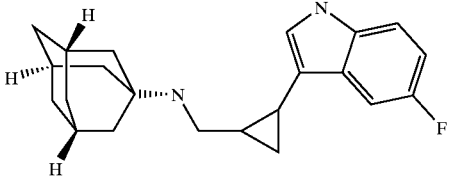 | 1.36 | 339.22 |
| 140 | 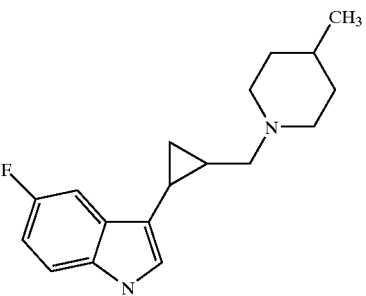 | 1.04 | 287.17 |
| 141 | 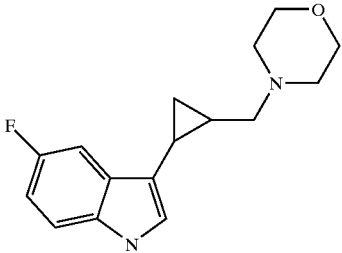 | 0.8 | 275.13 |
| 142 | 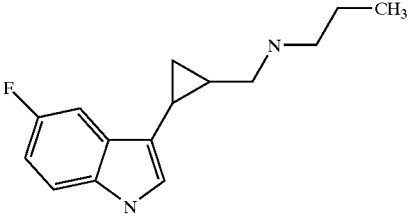 | 0.94 | 247.14 |
| 143 | 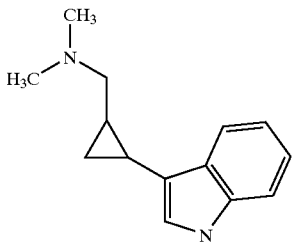 | 0.89 | 215.17 |
**See LCMS method below

EXAMPLE 144

3-[2-(2-Diethylamino-ethyl)-cyclopropyl]-1H-indole-5-carbonitrile

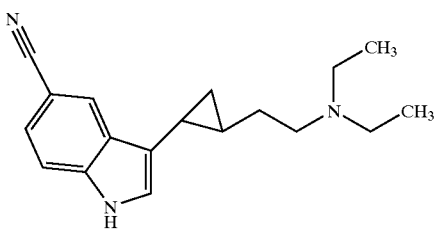

Butyl lithium (1.4 ml of 2.4M in hexane, 3.36 mmol) was added drop wise over a five min period under a nitrogen atmosphere to a stirred solution of methyltriphenylphosphonium bromide (1.186 g, 3.32 mmol) in dry THF (25 ml). The solution was stirred for 30 min at ambient temperature and then added dropwise to a solution of 3-(2-formyl-cyclopropyl)-1-(toluene-4-sulfonyl)-1H-indole-5-carbonitrile (1.10 g, 3.018 mmol) in 25 ml THF. The mixture was stirred for 24 hr, and then quenched with saturated aqueous ammonium acetate (2 ml). The mixture was concentrated in vacuo and then extracted with ethyl acetate (20 ml). The ethyl acetate extract was washed with water (10 ml), then washed with brine (10 ml), dried over sodium sulfate, and concentrated in vacuo. The residue was chromatographed on silica gel using methylene chloride as the eluent to give 1-(toluene-4-sulfonyl)-3-(2-vinyl-cyclopropyl)-1H-indole-5-carbonitrile (755 mg, 71%). $^1$H NMR (300 MHz, CDCl$_3$): δ 8.04 (d, 1H), 7.91 (s, 1H), 7.74 (d, 2H), 7.56 (d, 1H), 7.54 (s, 1H), 7.25(m, 2H), 5.57 (m, 1H), 5.19 (d, 1H), 5.01 (d, 1H), 2.36 (s, 3H), 1.86 (m, 1H), 1.63 (m, 1H), 1.16 (m, 2H). MS m/e 363.16 (MH$^+$).

9-Borabicyclo[3.3.1]nonane (4.1 ml of 0.5 M THF solution, 2.05 mmol) was added drop wise under a nitrogen atmosphere to a stirred solution of 1-(toluene-4-sulfonyl)-3-(2-vinyl-cyclopropyl)-1H-indole-5-carbonitrile (735 mg, 2.01 mmol) in dry THF (6 ml). The solution was heated to 30° C. for 6 hr and then cooled to 20° C. Absolute ethanol (12 ml), sodium hydroxide (2.6 ml of a 1N solution, 2.6 mmol), and hydrogen peroxide (0.85 ml of a 30% solution) were added sequentially to the stirred solution. The mixture was heated to 40° C. for 1 hr and then cooled to room temperature. Sodium hydroxide (2 ml of a 1N solution) was added and the mixture was extracted with ethyl acetate. The ethyl acetate extract was dried over sodium sulfate and concentrated in vacuo. The residue was chromatographed on silica gel using 3% acetone in methylene chloride as the eluent to give 3-[2-(2-hydroxy-ethyl)-cyclopropyl]-1-(toluene-4-sulfonyl)-1H-indole-5-carbonitrile (300 mg, 45%). $^1$H NMR (300 MHz, CDCl$_3$): δ 8.01 (d, 2H), 7.97 (s, 1H), 7.73(d, 1H), 7.28(s, 1H), 7.24 (d, 2H), 3.80 (m, 2H), 2.35 (s, 3H), 1.74–1.62 (m, 4H), 1.08 (m, 1H), 0.90 (m, 1H), 0.83 (m, 1H). MS m/e 381.17 (MH$^+$).

Oxalyl chloride (0.5 ml of 2.0 M solution in methylene chloride, 1.0 mmol) was diluted with dry methylene chloride (5.0 ml) and cooled to −78° C. under a nitrogen atmosphere. DMF (0.08 ml, 1.12 mmol) was added via a micro syringe and the solution was stirred at −78° C. for 10 min. A solution of 3-[2-(2-hydroxy-ethyl)cyclopropyl]-1-(toluene-4sulfonyl)-1H-indole-5-carbonitrile (250 mg, 0.657 mmol) in dry methylene chloride (5 ml) was added drop wise, and the solution was stirred at −78° C. for 1 hr, and then triethylamine (1.0 ml) was added. The solution was concentrated in vacuo, and the residue was dissolved in ethyl acetate (10 ml). The ethyl acetate solution was extracted with HCl (5 ml of 1 N solution), and with brine (5 ml). The ethyl acetate solution was dried over sodium sulfate and concentrated in vacuo. The residue was chromatographed on silica gel using methylene chloride as the eluent to give 3-[2-(2-oxo-ethyl)-cyclopropyl]-1-(toluene-4-sulfonyl)-1H-indole-5-carbonitrile (167 mg, 67%). $^1$H NMR (500 MHz, CDCl$_3$): δ 9.87 (s, 1H), 8.03 (d,1H), 7.96 (s, 1H), 7.74 (d, 2H), 7.56 (d, 1H), 7.35 (s, 1H), 7.25 (d, 2H), 2.59 (m, 2H), 2.36 (s, 3H), 1.67 (m, 1H), 1.30 (m, 1H), 1.30 (m, 1H), 1.02 (m, 1H), 0.89 (m, 1H). MS m/e 379.16 (MH$^+$).

A mixture of 3-[2-(2-oxo-ethyl)-cyclopropyl]-1-(toluene-4-sulfonyl)-1H-indole-5-carbonitrile (50 mg, 0.13 mmol), dimethylamine (0.2 ml of a 2M solution in THF, 0.4 mmol), and 112 mg (0.53 mmol) sodium triacetoxyborohydride in ethyl alcohol (2 ml), was stirred for 12 hr at 70° C. Sodium hydroxide (15 equivalents of a 1N solution) was added and the mixture was stirred for 45 min at 75° C. The reaction mixture was cooled, diluted with water (3 ml), and extracted twice with ethyl acetate (10 ml). The ethyl acetate extracts were dried over sodium sulfate and concentrated in vacuo. The residue was purified by preparative HPLC to give 3-[2-(2-diethylaminoethyl)-cyclopropyl]-1-(toluene-4-sulfonyl)-1H-indole-5-carbonitrile (8.2 mg, 22%). MS m/e 282.22 (MH$^+$).

EXAMPLE 145

3-[2-(2-Pyrrolidin-1-yl-ethyl)-cyclopropyl]-1H-indole-5-carbonitrile

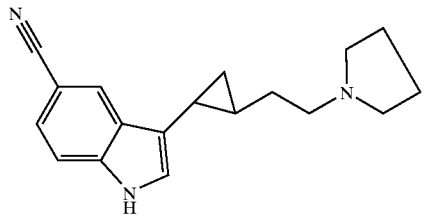

A procedure similar to Example 144, but using pyrrolidine in the last step, was used to give 3-[2-(2-pyrrolidin-1-yl-ethyl)-cyclopropyl]-1H-indole-5-carbonitrile (3.4 mg, 9.4%). MS m/e 280.19 (MH$^+$).

EXAMPLE 146

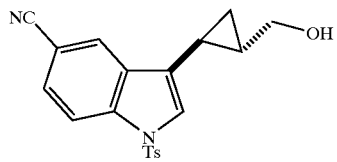

Alternate synthesis of (1S,2S)-trans-2-[5-cyano-1-(p-toluenesulfonyl)indol-3-yl]-cyclopropanemethanol (1S,2S)-trans-2-[5-cyano-1-(p-toluenesulfonyl)indol-3-yl]-cyclopropanemethanol is a key intermediate in the synthesis of (1S,2S)-trans-2-[5-cyanoindol-3-yl]-1-(N,N-dimethylaminomethyl)-cyclopropane (Example 5). This intermediate can be alternatively prepared by the following method:

Butyllithium (2.5 M solution in hexanes, 10 ml, 25 mmol, 1.25 equiv) was added over 5 min to a suspension of the methyltriphenylphosphonium bromide (10.7 g, 30 mmol, 1.5 equiv) in anhydrous tetrahydrofuran (250 ml) maintained at 0° C. under an atmosphere of dry nitrogen. After complete addition, the reaction mixture was allowed to warm to room temperature and stir for 1 h. The resulting orange colored solution, containing a small amount of unreacted solid phosphonium salt, was chilled to −15° C. Solid (5-cyanoindol-3-yl)carbox-aldehyde was added and the reaction mixture was allowed to warm to −5° C. over a period of 1 h. The reaction was quenched with water (250 ml) and extracted with ethyl acetate (3×100 ml). The organic extract was washed with brine (50 ml), dried over anhydrous magnesium sulfate, filtered, and concentrated in vacuo. The crude product was purified using silica gel column chromatography (step gradient: 5:1, 4:1 hexane/ethyl acetate) to afford 4.56 g (71% yield) of 1-(p-toluenesulfonyl)-3-vinylindole-5-carbonitrile as a white solid. An analytically sample was obtained by recrystallization from ethyl acetate/hexane: mp 134–135° C.; $^1$H NMR (400 MHz, CDCl$_3$): δ 8.08 (1H, d, 7.3 Hz), 8.06 (1H, d, 1.1 Hz), 7.78 (2H, d, J=8.4 Hz), 7.70 (1H, s), 7.58 (1H, dd, J=7.5, 1.5 Hz), 7.27 (2H, d, J=8.8 Hz), 6.73 (1H, dd, J=17.8, 11.3), 5.78 (1H, d, J=17.8 Hz), 5.43 (1H, d, J=11.5 Hz), 2.37 (3H, s); MS m/e 323 (M+H)$^+$. Anal. calcd. for $C_{18}H_{14}N_2O_2S$: C, 67.06; H, 4.37; N, 8.69. Found: C, 66.86; H, 4.36; N, 8.42.

A solution of ethyl diazoacetate (0.489 g, 4.29 mmol, 2.75 equiv) in toluene (4.5 ml) was added via syringe pump over a period of 16 h to a mixture of 1-(p-toluenesulfonyl)-3-vinylindole-5-carbonitrile (0.5 g, 1.56 mmol) and (R)-trans-Cl$_2$Ru(pybox-ip)(CH$_2$=CH$_2$) (39 mg, 0.078 mmol, 0.05 equiv) in toluene (15 ml) maintained at 50° C. under an atmosphere of dry nitrogen. After 16 h, a small aliquot of the crude reaction mixture was withdrawn and passed through a silica gel plug (2:1, hexanes/ethyl acetate). $^1$H-NMR analysis of the plugged aliquot revealed a 8.6:1 (trans/cis) mixture of product diastereomers. Without concentration, the crude reaction mixture was purified using silica gel column chromatography (3.5:1, hexanes/ethyl acetate) to afford 0.315 g (49% yield) of (1S,2S)-trans-2-[5-cyano-1-(p-toluenesulfonyl)indol-3-yl]-cyclopropane-carboxylic acid ethyl ester as a white crystalline solid. Chiral HPLC analysis revealed the mixture to be enriched to the extent of 88.4% enantiomeric excess: $^1$H NMR (400 MHz, CDCl$_3$): δ 8.04 (1H, dd, 8.6, 0.4 Hz), 7.90 (1H, dd, J=1.4, 0.5 Hz), 7.75 (2H, d, J=8.4 Hz), 7.57 (1H, dd, J=8.6, 1.6 Hz), 7.38 (1H, d, J=1.0 Hz), 7.27 (2H, d, J=7.8 Hz), 4.22 (2H, q, J=7.1), 2.46 (1H, m), 2.37 (3H, s), 1.86 (1H, m), 1.61 (1H, m), 1.31 (3H, t, J=7.1 Hz), 1.26 (1H, m); MS (CI) m/e 409 (M+H)$^+$. Chiral HPLC: Chiralpak AD (4.6×250 mm, 10 um), 85:15 (hexanes/EtOH), 0.5 ml/min, absorbance 225 nm; $t_R$ (RR)-25.2 min (5.8%), $t_R$ (S,S) 41.4 min (94.2%). Optical rotation: $[α]_D$ 59.3 (concentration=5.85 mg/ml, CH$_2$Cl$_2$).

A solution of diisobutylaluminumhydride (1M solution in THF, 3.34 ml, 3.34 mmol, 5 equiv) was added to a solution of (1S,2S)-trans-2-[5-cyano-1-(p-toluenesulfonyl)indol-3-yl]-cyclopropanecarboxylic acid ethyl ester (0.272 g, 0.665 mmol, 87.5% enantiomeric excess, contaminated with approximately 12% of the diastereomeric cis-cyclopropane isomer) in THF (15 ml) at −25° C. The resulting mixture was left to stir for 1.5 h and subsequently quenched with 0.1 N aqueous hydrochloric acid (10 ml). The crude mixture was poured into 1 N aqueous hydrochloric acid (100 ml) and extracted with ethyl acetate (2×100 ml). The organic layers were combined, washed with brine (25 ml), dried over anhydrous magnesium sulfate, and concentrated in vacuo. The crude product was purified using silica gel column chromatography (step gradient: 2.5:1, 2:1 hexane/ethyl acetate) to afford 204 mg of a white solid. The solid was recrystallized from ethyl acetate/hexanes to afford 167 mg (68% yield) of (1S,2S)-trans-2-[5-cyano-1-(p-toluenesulfonyl)indol-3-yl]-cyclopropanemethanol (87.5% enantiomeric excess, based on enantiomeric purity of starting ethyl ester): $^1$H NMR (400 MHz, CDCl$_3$): δ 8.03 (1H, dd, J=8.6, 0.6 Hz), 8.00 (1H, dd, J=1.5, 0.6 Hz), 7.74 (2H, d, J=8.4 Hz), 7.55 (1H, dd, J=8.6, 1.6 Hz), 7.33 (1H, d, J=1.0 Hz), 7.26 (2H, d, J=8.0 Hz), 3.69 (2H, m), 2.37 (3H, s), 1.78 (1H, m), 1.37 (1H, m), 0.95 (2H, t, J=7.0 Hz); MS (ESI) m/e 365 (M-H)$^-$.

Yet another alternative method for preparing (1S,2S)-trans-2-[5-cyano-1-(p-toluenesulfonyl)indol-3-yl]-cyclopropanemethanol is as follows:

A solution of tert-butyl diazoacetate (0.608 g, 4.28 mmol, 2.75 equiv) in toluene (4.4 ml) was added via syringe pump over a period of 16 h to a mixture of 1-(p-toluenesulfonyl)-3-vinylindole-5-carbonitrile (0.5 g, 1.56 mmol) and (R)-trans-Cl$_2$Ru(pybox-ip)(CH$_2$=CH$_2$) (39 mg, 0.078 mmol, 0.05 equiv) in toluene (15 ml) maintained at 62° C. under an atmosphere of dry nitrogen. HPLC analysis of a crude reaction aliquot revealed a 18:1 (trans/cis) mixture of product diastereomers. Without concentration, the crude reaction mixture was purified using silica gel column chromatography (5:1, hexanes/ethyl acetate) to afford 0.537 g (79% yield) of enantiomerically enriched (1S,2S)-trans-2-[5-cyano-1-(p-toluenesulfonyl)indol-3-yl]-cyclopropanecarboxylic acid tert-butyl ester as a white solid. An analytical sample was obtained by recrystallization from EtOAc/hexane. The extent of enantiomeric enrichment (% ee) was determined after diisobutylaluminum hydride reduction of the t-butyl ester to the corresponding alcohol (see subsequent experiment for details). $^1$H-NMR (400 MHz, CDCl$_3$): δ 8.04 (1H, dd, 8.6, 0.4 Hz), 7.89 (1H, d, J=1.0 Hz), 7.75 (2H, d, J=8.4 Hz), 7.57 (1H, dd, J=8.6, 1.5 Hz), 7.37 (1H, d, J=0.9 Hz), 7.27 (2H, d, J=8.6 Hz), 2.36 (4H, m), 1.79 (1H, m), 1.53 (1H), 1.50 (9H, s), 1.19 (1H, m); MS (ESI) m/e 454 (M+NH$_4$)$^+$. Optical rotation: $[α]_D$ 91.9 (concentration=5.89 mg/ml, CH$_2$Cl$_2$). Anal. calcd. for $C_{24}H_{24}N_2O_4S$: C, 66.03; H, 5.54; N, 6.41. Found: C, 66.02; H, 5.54; N, 6.29.

A solution of diisobutylaluminumhydride (1M solution in THF, 3.88 ml, 3.88 mmol, 5 equiv) was added to a solution of enantiomerically enriched (1S,2S)-trans-2-[5-cyano-1-(p-toluenesulfonyl)indol-3-yl]-cyclopropane-carboxylic acid tert-butyl ester (0.338 g, 0.0.776 mmol, contaminated with approximately 6% of the diastereomeric cis-cyclopropane isomer) in THF (15 ml) at −10° C. The resulting mixture was left to stir for 2 h and subsequently quenched with 1 N aqueous hydrochloric acid (10 ml). The crude mixture was poured into 1 N aqueous hydrochloric acid (100 ml) and extracted with ethyl acetate (2×100 ml). The organic layers were combined, washed with brine (25 ml), dried over anhydrous magnesium sulfate, and concentrated in vacuo. The crude product was purified using silica gel column chromatography (step gradient: 2.5:1, 2:1 hexane/ethyl acetate) to afford 108 mg (38% yield) of (1S,2S)-trans-2-[5-cyano-1-(p-toluenesulfonyl)indol-3-yl]-cyclopropanemethanol (77% enantiomeric excess as determined by chiral HPLC): $^1$H NMR (400 MHz, CDCl$_3$) 8.03 (1H, dd, J=8.6, 0.6 Hz), 8.00 (1H, dd, J=1.5, 0.6 Hz), 7.74 (2H, d, J=8.4 Hz), 7.55 (1H, dd, J=8.6, 1.6 Hz), 7.33 (1H, d, J=1.0 Hz), 7.26 (2H, d, J=8.0 Hz), 3.69 (2H, m), 2.37 (3H, s), 1.78 (1H, m), 1.37 (1H, m), 0.95 (2H, t, J=7.0 Hz). Chiral HPLC: Chiralpak AD (4.6×250 mm, 10 um), 60:40 (hexanes/EtOH), 0.8 ml/min, absorbance 220 run; $t_R$ (R,R)-7.83 min (11.6%), $t_R$ (S,S) 24.82 min (88.4%).

EXAMPLE 147

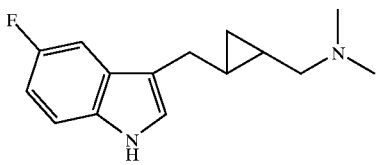

[2-(5-Fluoro-1H-indol-3-ylmethyl)-cyclopropylmethyl]-dimethylamine

A solution of diethylaluminum chloride in dichloromethane (16 ml, 1 M, 16 mmol) was added to a solution of 5-fluoroindole in dichloromethane at 0°. After stirring for 10 min at 0°, a solution of trans-2-ethoxycarbonylcyclopropanecarboxylic acid chloride (16 mmol, prepared from 2.5 g 16 mmol 2-ethoxycarbonylcyclopropanecarboxylic acid and 1.9 g, 16 mmol, thionyl chloride) in dichloromethane was added at 0°. The reaction was stirred 1 hr at 0° and 3 hr at 20°. The reaction was poured over a mixture of 1 N HCl and ice. The mixture was extracted with ethyl acetate. The extracts were washed with 1 N NaOH solution and brine, dried and concentrated in vacuo. The residue was triturated with isopropyl ether and the crude trans-2-(5-fluoro-3-indolylcarbonyl)cyclopropanecarboxylic acid ethyl ester (1.25 g) as beige solid.

The crude trans-2-(5-fluoro-3-indolylcarbonyl)cyclopropanecarboxylic acid ethyl ester (0.55 g, 2 mmol) was suspended in ethanol and sodium hydroxide solution (4 ml, 1N, 4 mmol) was added. The resultant solution was stirred for 4 hr at 20° and 0.5 hr at reflux. The ethanol was removed in vacuo and the residue mixed with water. The mixture was extracted with ethyl acetate. The aqueous layer was separated and made acidic with 12 N HCl. The precipitate was collected and air dried to give trans-2-(5-fluoro-3-indolylcarbonyl)cyclopropanecarboxylic acid as an off-white solid (0.30 g), mp 276–277 dec. LC/MS mw=247; retention time 1.19 min. Mol wt calc$^1$d for $C_{13}H_{10}FNO_2$: 247.

A solution of trans-2-(5-fluoro-3-indolylcarbonyl)cyclopropanecarboxylic acid (1.5 g, 6 mmol) and carbonyl diimidazole in tetrahydrofuran was stirred for 0.5 hr. A solution of dimethylamine in tetrahydrofuran (3 ml, 2 M solution, 6 mmol) was added and the solution stirred for 3 hr. The solution was concentrated in vacuo and the residue dissolved in ethyl acetate. The organic solution was washed with 1 N HCl and saturated sodium bicarbonate solution. The solution was dried over sodium sulfate and concentrated in vacuo. The residue was triturated with isopropyl ether to give 1.5 g of trans-2-(5-fluoro-3-indolylcarbonyl)cyclopropanecarboxylic acid dimethylamide, mp 239–241° C. LC/MS mw=274; retention time 1.23 min. Mol wt calc$^1$d for $C_{15}H_{15}FN_2O_2$: 274.

Trans-2-(5-fluoro-3-indolylcarbonyl)cyclopropanecarboxylic acid dimethylamide (0.27 g, 1 mmol) in tetrahydrofuran was added to a suspension of lithium aluminum hydride (0.2 g, 0.5 mmol) in tetrahydrofuran. The mixture was heated at reflux for 4 hr and stirred at 20° for 12 hr. The reaction was quenched by the sequential addition of 0.5 ml of water, 0.5 ml 15% NaOH solution and 0.5 ml water. After stirring for 1 hr, the insoluble solids were removed by filtration and washed with acetone. The organic solution was concentrated in vacuo and the residue dissolved in methanol and purified by absorption on SCX resin washing with methanol and elution with 1 M methanolic ammonia solution. The basic elutants were concentrated in vacuo, dissolved in fresh methanol and made acidic with 12 N HCl. The acidic solution was thoroughly concentrated in vacuo to give racemic [2-(5-fluoro-1H-indol-3-ylmethyl)-cyclopropyl-methyl]-dimethylamine (165 mg). LC/MS mw=247; retention time 0.96 min. Mol wt calc$^1$d for $C_{15}H_{19}FN_2$: 246.

EXAMPLE 148

(+)-[2-(5-Fluoro-1H-indol-3-ylmethyl)-cyclopropylmethyl]-dimethylamine

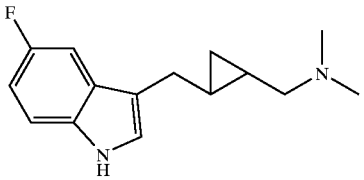

Racemic trans-2-(5-fluoro-3-indolylcarbonyl)-cyclopropanecarboxylic acid dimethylamide was resolved by chiral HPLC chromatography on a Chiralcel OD column (50×500 mm with 20 μm packing) using 10% Isopropanol/hexane as the eluent at a flow rate of 60 mL/min for 60 minutes and a UV detector set at 220 nm. (−)-Trans-2-(5-fluoro-3-indolylcarbonyl)-cyclopropanecarboxylic acid dimethylamide eluted at 9.6 minutes, and (+)-trans-2-(5-fluoro-3-indolylcarbonyl)-cyclopropanecarboxylic acid dimethylamide at 41.8 minutes.

A solution of (−)-trans-2-(5-fluoro-3-indolylcarbonyl)-cyclopropanecarboxylic acid dimethylamide (180 mg, 0.66 mmol) in THF was added dropwise to a suspension of LAH (100 mg, 2.63 mmol) in THF at room temperature with stirring. The reaction was heated to reflux and stirred for 1 h. The reaction was then cooled to room temperature, diluted with ether, and quenched with aqueous NaOH (1 mL of 1 N solution). The resulting precipitate was filtered and washed with ether. The organic filtrate was concentrated in vacuo. The residue was dissolved in methylene chloride, and transferred directly to an SCX resin cartridge. The cartridge was washed with methanol, and then with methanolic ammonia (2.0 M) to give (+)-[2-(5-fluoro-1H-indol-3-ylmethyl)-cyclopropyl-methyl]-dimethylamine [150 mg, 94% yield, optical rotation +19.26° (c=1.38 mg/mL, ethanol, 20° C.)]. $^1$H NMR (MeOH-d4): δ 7.25 (dd, J=8.8, 4.5 Hz, 1H), 7.17 (dd, J=9.9, 2.5 Hz, 1H), 6.82 (dt, J=2.4 Hz, 1H), 2.69 (dd, J=6.5 Hz, 2H), 2.29 (dd, J=4.86 Hz, 1H), 2.20 (s, 6H), 2.15 (dd, J=12.8 Hz, 1H), 0.90 (m, 1H), 0.70 (m, 1H), 0.51 (m, 1H), and 0.39 (m, 1H), FIMS: 247.3 (M+H)$^+$.

EXAMPLE 149

(−)-[2-(5-Fluoro-1H-indol-3-ylmethyl)-cyclopropylmethyl]-dimethylamine

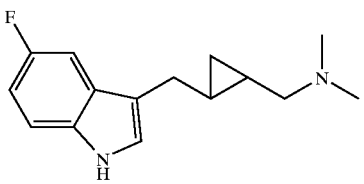

In a manner similar to example 148, (+)-trans-2-(5-fluoro-3-indolylcarbonyl)-cyclopropanecarboxylic acid dimethylamide was reduced to give (−)-[2-(5-fluoro-1H-indol-3-ylmethyl)-cyclopropyl-methyl]-dimethylamine [140 mg, 88% yield, optical rotation −22.86° (c=1.08 mg/mL, ethanol, 20° C.)].

EXAMPLE 150

N,N-dimethyl-2-(3-bromoindol-5-yl)cycloprop-1-yl methylamine

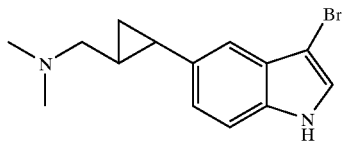

A mixture of sodium hydride (0.44 g of a 60% suspension in mineral oil, 11 mmol) and diethyl-(N-methoxy-N-methyl-carbamoylmethyl)-phosphonate (3.0 g, 3 equiv.) in anhydrous THF was stirred at room temperature for 30 minutes. A solution of indole-5-carboxaldehyde (0.61 g, 4.18 mmol) was added dropwise to the mixture. The reaction was complete after 2 h after the addition of the starting indole. The mixture was quenched with water (50 ml), then diluted with ether. The organic layer was separated, dried over anhydrous magnesium sulfate, filtered, and concentrated in vacuo to give N-methoxy-N-methyl-3-(indol-5-yl)acrylamide as a yellow oil which solidified on standing to an off-white solid (1.53 g, quantitative yield. $^1$H NMR (CDCl$_3$): δ 8.55 (br, 1H), 7.87 (d, J=18.6 Hz, 1H), 7.85 (s, 1H), 7.38 (d, J=8.5 Hz, 1H), 7.25 (d, J=8.5 Hz, 1H), 7.23 (m, 1H), 7.0 (d, J=18.6 Hz, 1H), 6.58 (m, 1H), 3.78 (s, 3H), and 3.32 (s, 3H). FIMS: 229.1 (M−H)$^−$, reverse-phase HPLC purity: 88%.

A mixture of trimethyl sulfoxonium iodide (4.03 g, 18.3 mmol) and sodium hydride (0.61 g of a 60% suspension in mineral oil, 18.3 mmol) in anhydrous THF was stirred at room temperature for 3 h. A solution of N-methoxy-N-methyl-3-(indol-5-yl)acrylamide (1.4 g,) in anhydrous THF was added dropwise to the reaction. The reaction was stirred and heated to a gentle reflux for 16 hours. The reaction was quenched with an excess of water and extracted with ethyl acetate. The organic extract was dried over anhydrous magnesium sulfate, filtered, and concentrated in vacuo a yellow oil. This oil was purified by chromatography on silica gel using 15–50% ethyl acetate in hexane as the eluent, to trans N-methoxy-N-methyl-2-(indol-5-yl)cycloprop-1-yl) carboxamide (0.28 g, 28%) $^1$H NMR (CDCl$_3$): δ 8.10 (br, 1H), 7.41 (s, 1H), 7.31 (d, J=8.4 Hz, 1H), 7.20 (t, J=2.8 Hz, 1H), 7.00 (dd, J=8.4, 1.7 Hz, 1H), 6.50 (m, 1H), 3.69 (s, 3H), 3.25 (s, 3H), 2.61 (m, 1H), 2.40 (br, 1H), 1.64 (m, 1H) and 1.37 (m, 1H).

Lithium aluminum hydride (87 mg, 2.30 mmol) was suspended in anhydrous THF at −45° C. A THF solution of trans N-methoxy-N-methyl-2-(indol-5-yl)cycloprop-1-yl) carboxamide (0.28 g, 1.15 mmol) was added slowly over a period of 10 min with stirring. The reaction was stirred for 1 h at −45° C., diluted with ether, and then quenched with aqueous NaOH (1 mL of 1 N solution) and warmed to room temperature. The white precipitate was filtered, washed with ether, and the organic filtrate was concentrated in vacuo. The residue was dissolved in ethyl acetate, dried over anhydrous magnesium sulfate, filtered, and concentrated in vacuo to give 2-(indol-5-yl)cycloprop-1-yl)carboxaldehyde (230 mg, 100%) as a yellow oil which was used without purification. $^1$H NMR (CDCl$_3$): δ 9.32 (d, J=4.8 Hz, 1H), 8.15 (br, 1H), 7.41 (s, 1H), 7.27 (d, J=9.5 Hz, 1H), 7.21 (t, J=2.9 Hz, 1H), 6.97 (dd, J=8.4, 1.2 Hz, 1H), 6.50 (m, 1H), 2.76 (s, 1H), 2.17 (s, 1H), 1.76 (m, 1H), and 1.58 (m, 1H).

A solution of 2-(Indol-5-yl)cycloprop-1-yl) carboxaldehyde (230 mg) and dimethyl amine (2.84 mL of 2 M solution in THF, 5.68 mmol) in absolute ethanol was stirred at room temperature as sodium triacetoxyborohydride (1.20 g, 5.68 mmol) was added. After 15 minutes of stirring, the colorless, clear solution was concentrated to dryness in vacuo. The residue was dissolved in ethyl acetate and 1 N NaOH solution. The organic layer was separated, dried over anhydrous magnesium sulfate, and concentrated in vacuo to give N,N-dimethyl-2-(indol-5-yl)cycloprop-1-yl methylamine (240 mg, 100%) as an oil.
$^1$H NMR (CDCl$_3$): δ 8.10 (br, 1H), 7.35 (s, 1H), 7.27 (d, J=8.4 Hz, 1H), 7.16 (t, J=2.7 Hz, 1H), 6.94 (dd, J=11.4, 1.8 Hz, 1H), 6.45 (m, 1H), 2.49 (dd, J=6.3 Hz, 1H), 2.38 (dd, J=19.2 Hz, 1H), 2.35 (s, 6H), 1.81 (m, 1H), 1.20 (m, 1H), 0.98 (m, 1H), and 0.82 (m, 1H).

A solution of trans N,N-dimethyl-2-(indol-5-yl) cycloprop-1-yl methylamine (75 mg, 0.35 mmol), and potassium t-butoxide (29 mg, 0.35 mmol) in anhydrous THF at 0° C. was stirred at 0° C. for 30 min before cyanogen bromide (37 mg, 0.35 mmol) was added. The reaction was warmed to room temperature and stirred for 16 h. The reaction was concentrated in vacuo, and the residue was dissolved in water, and extracted with ethyl acetate. The organic extracts were dried over anhydrous magnesium sulfate, filtered, and concentrated in vacuo to give N,N-dimethyl-2-(3-bromoindol-5-yl)cycloprop-1-yl methylamine (100 mg, 98%) as a colorless oil. $^1$H NMR (MeOH-d4): δ 7.26 (d, J=8.4 Hz, 1H), 7.22 (s, 1H), 7.16 (s, 1H), 6.94 (dd, J=8.7, 1.5 Hz, 1H), 2.58 (dd, J=6.0, 1H), 2.35 (s, 6H), 2.31 (m, 1H), 1.80 (m, 1H), 1.22 (m, 1H), 1.03 (m, 1H), and 0.88 (m, 1H). FIMS: 293.1 (M−H), reverse-phase HPLC purity: 85%.

EXAMPLE 151

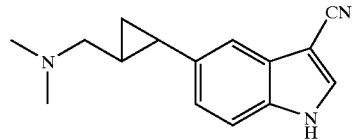

5-(2-Dimethylaminomethyl-cyclopropyl)-1H-indole-3-carbonitrile

Phosphorous oxychloride (0.08 mL, 0.85 mmol, 0.91 equiv.) and dimethyl formamide (0.32 mL, 4.09 mmol, 4.4 equiv.) were combined at room temperature with stirring. After 15 min, N,N-dimethyl-2-(indol-5-yl)cycloprop-1-yl-methylamine was added dropwise in DMF (5 mL). After 2 hs of stirring at room temperature, ice and 1 N NaOH were added, then the mixture was diluted further with water and extracted with ethyl acetate. The organic layer was dried over anhydrous magnesium sulfate, filtered, and concentrated in vacuo to give N,N-dimethyl-2-(3-formyl-indol-5-yl)cycloprop-1-yl-methylamine (120 mg) as an oil. $^1$H NMR (MeOH-d4): δ 9.84 (s, 1H), 8.04 (s, 1H), 7.97 (s, 1H), 7.36 (d, J=8.4 Hz, 1H), 7.05 (dd, J=15.5, 1.7 Hz, 1H), 2.59 (dd, J=12.7, 6.7, 1H), 2.35 (s, 6H), 2.30 (m, 1H), 1.80 (m, 1H), 1.20 (m, 1H), 1.05 (m, 1H), and 0.88 (m, 1H).

In 5 mL of acetic acid was combined 120 mg of crude N,N-dimethyl-2-(3-formyl-indol-5-yl)cycloprop-1-yl-methylamine, ammonium hydrogen phosphate (0.48 g, 3.62 mmol, 7.3 equiv.), and nitropropane (0.04 mL, 0.5 mmol, 1 equiv.). The mixture was stirred and heated to a gentle reflux for 16 h. Water was added after cooling reaction to room temperature, and the mixture was made basic by the addition of 1 N NaOH. The mixture was extracted with ethyl acetate and dried over anhydrous magnesium sulfate, filtered, and concentrated in vacuo to give N,N-dimethyl-2-(3-cyanoindol-5-yl)cycloprop-1-yl methylamine (90 mg, 75%) as a brown oil. The oil was purified by flash chromatography to give a brown solid with 92% purity by reverse-phase HPLC. $^1$H NMR (MeOH-d4): δ 7.88 (s, 1H), 7.40 (d, J=7.5 Hz, 1H), 7.36 (d, J=1.9 Hz, 1H), 7.04 (dd, J=8.5, 1.7 Hz, 1H), 2.62 (dd, J=7.3 Hz, 1H), 2.42 (m, 1H), 2.38 (s, 6H), 1.89 (m, 1H), 1.20 (m, 1H), 1.08 (m, 1H), and 0.90 (m, 1H). IR: 2214.5 cm$^{-1}$. FIMS: 238.2 (M–H)$^-$.

EXAMPLE 152

[2-(5,6-Difluoro-1H-indol-3-yl)-cyclopropylmethyl]-dimethyl-amine

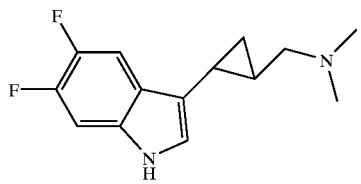

3,4-Difluorotoluene (9.00 g, 70.3 mmol), ammonium nitrate (6.75 g, 84.3 mmol) and trifluoroacetic acid (25 ml) were stirred at ambient temperature for 18 h. The resulting solution was made basic to pH>10 with 5 N sodium hydroxide and, after cooling to ambient temperature, extracted with diethyl ether (3×40 ml). The combined organic layers were washed with brine (40 ml) and dried over anhydrous sodium sulfate. The filtrate was concentrated in vacuo. The crude product was purified by silica gel column chromatography, eluting with hexanes/ethyl acetate (9:1), to afford 3,4-difluoro-5-nitrotoluene (4.63 g, 40%) as a light yellow oil. $^1$H-NMR δ (400 MHz, CDCl$_3$) 7.94 (1H, dd, J=9.9, 7.3 Hz), 7.17 (1H, dd, J=10.3, 7.6 Hz), 2.61 (3H, s).

A solution of 3,4-difluoro-5-nitrotoluene (7.33 g, 42.3 mmol) in anhydrous dimethylformamide (20 ml) was treated with dimethylformamide-dimethylacetal (6.06 g, 50.8 mmol) and stirred at 110° C. for 3 h, then at 70° C. for 18 h. The resulting deep red solution was diluted with brine (150 ml) and extracted with dichloromethane (5×30 ml). The pooled organic extracts were washed once with brine and dried over anhydrous sodium sulfate. The filtrate was concentrated in vacuo to afford [2-(4,5-difluoro-2-nitro-phenyl)-vinyl]-dimethyl-amine (7.0 g, 73%) as a deep red oil that solidified upon standing. The crude product was used without further characterization.

A suspension of [2-(4,5-difluoro-2-nitro-phenyl)-vinyl]-dimethyl-amine (7.0 g, 30.7 mmol) and 10% palladium on charcoal (1.4 g) in methyl alcohol was hydrogenated in a Parr apparatus at 50 psi for 2 h and then filtered through Celite. The filtrate was concentrated in vacuo and the crude product purified by silica gel column chromatography (hexanes/ethyl acetate, 8:2) to afford 5,6-difluoroindole (1.28 g, 28%) as a yellow solid. $^1$H-NMR δ (400 MHz, CDCl$_3$) 8.10 (1H, br s), 7.36 (1H, dd, J=10.7, 7.8 Hz), 7.22 (1H, t, J=2.8 Hz), 7.17 (1H, dd, J=7.4, 3.1 Hz), 6.50 (1H, m).

5,6-Difluoroindole was converted to 5,6-difluoroindole carboxaldehyde in a manner similar to (5-cyanoindol-3-yl) carboxaldehyde in Example 1. $^1$H-NMR (400 MHz, CDCl$_3$) 9.87 (1H, s), 8.15 (s, 1H), 7.96 (1H, dd, J=8.0, 2.8 Hz), 7.38 (1H, dd, J=6.8, 3.8 Hz).

5,6-difluoroindole carboxaldehyde was then converted to 5,6-difluoro-1-(toluene-4-sulfonyl)-1H-indole-3-carbaldehyde in a manner similar to [5-cyano-1-(p-toluenesulfonyl)indol-3-yl]carbox-aldehyde in Example 1. $^1$H-NMR (400 MHz, CDCl$_3$) 10.04 (1H, s), 8.22 (1H, s), 8.05 (1H, dd, J=7.7, 2.1 Hz), 7.83 (2H, d, J=6.7 Hz), 7.79 (1H, dd, J=10.4, 6.6 Hz), 7.34 (2H, dd, J=8.0, 2.7 Hz), 2.41 (3H, s).

5,6-difluoro-1-(toluene-4-sulfonyl)-1H-indole-3-carbaldehyde was then converted to (trans)-3-[5,6-Difluoro-1-(toluene-4-sulfonyl)-1H-indol-3-yl]-N-methoxy-N-methyl-acrylamide in a manner similar to (trans)-[5-cyano-1-(p-toluenesulfonyl)-indol-3-yl]-N-methoxy-N-methylacrylamide in Example 1. LC-MS: 2.74 min; 421.1 (MH)$^+$.

(Trans)-3-[5,6-Difluoro-1-(toluene-4-sulfonyl)-1H-indol-3-yl]-N-methoxy-N-methyl-acrylamide was converted to 2-[5,6-Difluoro-1-(toluene-4-sulfonyl)-1H-indol-3-yl]-cyclopropanecarboxylic acid methoxy-methyl-amide in a manner similar to [trans-2-[5-Cyano-1-(p-toluenesulfonyl) indol-3-yl]cycloprop-1-yl]-N-methoxy-N-methylcarboxamide in Example 1. LC-MS: 2.71 min; 435.1 (MH)$^+$.

2-[5,6-Difluoro-1-(toluene-4-sulfonyl)-1H-indol-3-yl]-cyclopropane-carboxylic acid methoxy-methyl-amide was converted to 2-[5,6-Difluoro-1-(toluene--4-sulfonyl)-1H-indol-3-yl]-cyclopropanecarbaldehyde trans-2-[5-Cyano-1-(p-toluenesulfonyl)-indol-3-yl]cyclopropane-carboxaldehyde in Example 1. $^1$H-NMR (400 MHz, CDCl$_3$) 9.44 (1H, d, J=4.2 Hz), 7.81 (1H, dd, J=10.6, 6.7 Hz), 7.72 (2H, dd, J=6.6, 1.6), 7.28 (4H, m), 2.51 (1H, m), 2.37 (3H, s), 2.09 (1H, m), 1.71 (1H, m), 1,46 (1H, m). LC-MS: 2.63 min; 376.1 (MH)$^+$.

A solution of trans-2-[5,6-difluoro-1-(p-toluenesulfonyl) indol-3-yl]cyclopropane-carboxaldehyde (0.48 g, 1.28 mmol), dimethylamine (3 ml, 6 mmol, 2M/THF) and tetrahydrofuran (15 ml) was treated with sodium triacetoxyborohydride (1.35 g, 6.39 mmol) and stirred at ambient temperature for 1 h. The resulting solution was evaporated in vacuo and the residue treated with 10 N sodium hydroxide (10 ml) and methyl alcohol (10 ml). The solution was heated at a gentle reflux for 2 h then cooled and concentrated in vacuo. The residue was dissolved in ethyl acetate and washed with 1 N sodium hydroxide, and brine, and dried over anhydrous sodium sulfate. The filtrate was concentrated in vacuo to an amber colored oil. Silica gel column chromatography (chloroform/2M ammonia in methanol, 9:1) afforded [2-(5,6-difluoro-1H-indol-3-yl)-cyclopropylmethyl]-dimethyl-amine (100 mg, 31%) as a light oil which solidified upon standing. $^1$H-NMR (400 MHz, CDCl$_3$) 8.09 (1H, br s), 7.40 (1H, m), 7.10 (1H, dd, J=10.6, 6.6), 6.89 (1H, d, J=2.2 Hz), 2.38 (2H, m), 2.34 (6H, s), 1.69 (1H, m), 1.18 (1H, m), 0.90 (1H, m), 0.78 (1H, m). LC-MS: 1.95 min; 251 (MH)$^+$.

EXAMPLE 153

5-(2-Dimethylaminomethyl-cyclopropylmethyl)-1H-indole-3-carbonitrile

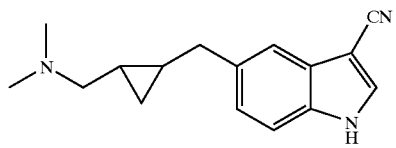

Commercially available 5-bromoindole-3-carboxaldehyde (11.3 g, 50.4 mmol), ammonium hydrogen phosphate (47.0 g, 353 mmol), 1-nitropropane (4.49 g, 50.4 mmol), and glacial acetic acid (100 ml) were heated at a gentle reflux for 18 h. The resulting mixture was concentrated in vacuo and the residue mixed with 5 N sodium hydroxide (500 ml) and ice chips. The precipitate was collected by filtration and rinsed several times with water. The filtrate was concentrated in vacuo to afford 5-bromo-3-cyanoindole (7.23 g, 65%) as a dark solid. $^1$H-NMR (400 MHz, CDCl$_3$) δ 10.0 (1H, s), 8.68 (1H, br s), 8.51 (1H, s), 7.85 (1H, s), 7.43 (1H, dd, J=8.6, 1.9 Hz), 7.32 (1H, d, J=8.6 Hz).

A suspension of potassium hydride (2.16 g, 18.8 mmol, 35% mineral oil dispersion) and anhydrous tetrahydrofuran at 0° C. was treated with a solution of 5-bromo-3-cyanoindole dissolved in tetrahydrofuran (15 ml) by dropwise addition. After 15 min the solution was cooled to −78° C. and treated with n-butyllithium (21 ml, 52.5 mmol, 2.5M/hexanes) by dropwise addition. The resulting mixture was stirred for 30 min after the addition was complete and then treated with commercially available diethyl-trans-cyclopropane carboxylate (12.7 g, 68.4 mmol) in a steady stream. The solution was stirred for 18 h, gradually warming to ambient temperature, and then carefully poured into 1 N hydrochloric acid (100 ml) and extracted with ethyl acetate (3×50 ml). The combined organic extracts were washed with brine (1×50 ml), dried over anhydrous sodium sulfate and concentrated in vacuo. Silica gel column chromatography (hexanes, ethyl acetate 1:1) afforded 2-(3-Cyano-1H-indole-5-carbonyl)-cyclopropanecarboxylic acid ethyl ester (1.12 g, 23%) as tan solid. LC-MS: 1.40 min; 283 (MH)$^+$.

A suspension of lithium aluminum hydride (0.3 g, 7.94 mmol) in anhydrous tetrahydrofuran (50 ml) was cooled to −45° C. and treated with a solution of the 2-(3-Cyano-1H-indole-5-carbonyl)-cyclopropanecarboxylic acid ethyl ester (1.12 g dissolved in 10 ml THF). The mixture was stirred for 1 h and quenched with water followed by sodium hydroxide solution. The aluminum salts were removed by filtration. The filtrate was concentrated in vacuo to afford 2-[(3-cyano-1H-indol-5-yl)-hydroxy-methyl]-cyclopropanecarboxlic acid ethyl ester (1.0 g) as an amber oil.

LC-MS: 1.49 min; 291.1 (MNa)$^+$.

A solution of the 2-[(3-cyano-1H-indol-5-yl)-hydroxy-methyl]-cyclopropane-carboxylic acid ethyl ester (1.0 g, 3.5 mmol), dichloromethane (25 ml), and trifluoroacetic acid (5 ml) was cooled to 0° C. and treated with triethylsilane (0.57 g, 5.0 mmol). The solution was stirred for 30 min and then diluted with an additional 50 ml dichloromethane and neutralized with 1 N sodium hydroxide. The organic layer was washed with brine (1×50 ml) and dried over anhydrous sodium sulfate. The filtrate was concentrated in vacuo to a deep amber oil. Silica gel column chromatography (hexanes, ethyl acetate 1:1) afforded 2-(3-cyano-1H-indol-5-ylmethyl)-cyclopropane-carboxylic acid ethyl ester (0.62 g, 56%) as a light yellow oil. LC-MS: 1.38 min; 269.1 (MH)$^+$.

2-(3-Cyano-1H-indol-5-ylmethyl)-cyclopropanecarboxylic acid ethyl ester (0.62 g, 2.31 mmol), methanol (10 ml), and lithium hydroxide monohydrate (0.48 g, 11.6 mmol) were heated at a gentle reflux for 2 h. The solution was concentrated in vacuo and the residue taken up in 1 N hydrochloric acid (30 ml) and extracted with ethyl acetate (3×10 ml). The combined organic extracts were dried over anhydrous sodium sulfate and concentrated in vacuo to afford 2-(3-Cyano-1H-indol-5-ylmethyl)-cyclopropanecarboxylic acid (0.45 g, 81%) as a light brown oil which solidified upon standing. LC-MS: 1.21 min; 263.2 (MNa)$^+$.

A solution of 2-(3-cyano-1H-indol-5-ylmethyl)-cyclopropanecarboxylic acid (0.080 g, 0.33 mmol), N,N-dimethylhydroxylamine hydrochloride (0.065 g, 0.67 mmol), 1-(3-dimethylaminopropyl)-3-ethylcarbodiimide hydrochloride (0.077 g, 0.40 mmol), triethylamine (0.13 g, 1.33 mmol), and dichloromethane (5 ml) was stirred at ambient temperature for 1 h then diluted further with an additional 10 ml dichloromethane. The solution was washed with 1N hydrochloric acid (1×5 ml), 1N sodium hydroxide (1×5 ml), and brine (1×5 ml) and dried over anhydrous sodium sulfate. The filtrate was concentrated in vacuo to afford 2-(3-cyano-1H-indol-5-ylmethyl)-cyclopropanecarboxylic acid methoxy-methyl-amide (0.075 g, 79%) as a light brown film. $^1$H-NMR (400 MHz, CDCl$_3$) 7.69 (1H, m), 7.57 (1H, s), 7.22 (1H, d, J=2.7 Hz), 7.11 (1H, d, J=1.52 Hz), 3.69 (3H, s), 3.20 (3H, s), 2.81 (2H, m), 2.10 (1H, m), 1.73 (1H, m), 1.28 (1H, m), 0.91 (1H, m).

A suspension of lithium aluminum hydride (0.020 g, 0.53 mmol) in anhydrous tetrahydrofuran (5 ml) at −45° C. was treated with a solution 2-(3-cyano-1H-indol-5-ylmethyl)-cyclopropanecarboxylic acid methoxy-methyl-amide in 5 ml tetrahydrofuran. After 30 min at −45° C. an additional 0.53 mmol lithium aluminum hydride was added. The reaction was quenched with water followed by 1 N sodium hydroxide after another 30 min. The aluminum salts were removed by filtration and the filtrate was concentrated in vacuo to afford 5-(2-Formyl-cyclopropylmethyl)-1H-indole-3-carbonitrile (0.034 g, 57%) as a light yellow film. $^1$H-NMR (400 MHz, CDCl$_3$) 9.07 (1H, d, J=5.16 Hz), 7.71 (1H, s), 7.58 (1H, s), 7.39 (1H, d, J=8.2 Hz), 7.22 (1H, m), 6.98 (1H, s), 2.80 (2H, m), 1.86 (2H), 1.40 (1H, m), 1.11 (1H, m).

A solution of 2-(3-cyano-1H-indol-5-ylmethyl)-cyclopropanecarboxylic acid methoxy-methyl-amide (0.029 g, 0.13 mmol), dimethylamine (0.7 ml, 1.4 mmol, 2M/THF), and methyl alcohol (5 ml) was treated with sodium triacetoxyborohydride (0.28 g, 1.13 mmol) and stirred at ambient temperature for 1 h. The solution was concentrated in vacuo and the residue applied directly to a silica gel column and eluted with chloroform, methyl alcohol, triethylamine 95:5:0.1 to afford 5-(2-Dimethylaminomethyl-cyclopropylmethyl)-1H-indol-3-carbonitrile (23 mg, 69%) as a light salmon colored solid. $^1$H-NMR (400 MHz, CDCl$_3$) 8.88 (1H, br s), 7.66 (2H, dd, J=19.4, 2.3 Hz), 7.33 (1H, d, J=8.4 Hz), 7.18 (1H, dd, J=8.4, 1.5 Hz), 2.72 (2H, m), 2.25 (6H, s), 2.24 (2H, m), 0.88 (2H, m), 0.53 (1H, m), 0.45 (1H, m).

LC-MS: 0.90; 254.2 (MH)$^+$.

EXAMPLE 154

Methyl-[2-(5-trifluoromethyl-1H-indol-3-yl)-cyclopropylmethyl]-amine

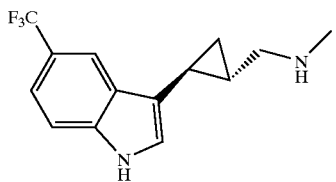

A mixture of 4-Nitrobenzotrifluoride (25.0 g, 131 mmol) and 4-chlorophenoxyacetonitrile (24.1 g, 144 mmol) in dry DMF (200 mL) was added dropwise over 1 h to a stirred solution of potassium tert-butoxide (32.3 g, 288 mmol) in dry DMF (200 mL) at −10° C. After complete addition the resulting purple solution was maintained at −10° C. for 3 h then poured into a mixture of ice water (200 mL) and 5 N aqueous HCl (200 mL). The resulting mixture was extracted with dichloromethane (3×300 mL). The combined extracts were washed with 10% aqueous NaOH, 5 N HCl, brine, dried over sodium sulfate, and concentrated in vacuo to give the crude (2-nitro-5-trifluoromethylphenyl) acetonitrile. The crude (2-nitro-5-trifluoromethylphenyl) acetonitrile (24.6 g, 107 mmol) was dissolved in 9:1 EtOH:H2O (300 mL) and glacial acetic acid (3.0 mL). This mixture was hydrogenated over 10% Pd/C (10.0 g) at 50 psi for 16 h at room temperature. The reaction was filtered through celite and evaporated in vacuo. The residue was partitioned between saturated aqueous sodium carbonate and dichloromethane (2×200 mL) and the combined organic extract was dried over sodium sulfate, filtered, and concentrated in vacuo. The crude material was purified by silica gel column chromatography (hexanes/ethyl acetate, 20:1, 9:1, 5:1) to afford 12.9 g (65% yield) of 5-trifluoromethyl-1H-indole as a yellow solid: $^1$H NMR (400 MHz, CDCl3) 8.34, (1H, br s), 7.95 (1H, s), 7.45 (2H, m), 7.32 (1H, m), 6.65 (1H, m); MS m/e 184 (M−H)−. Anal calcd. for $C_9H_6F_3N.0.15\ H_2O$: C, 57.55; H, 3.38; N, 7.46. Found: C, 57.25; H, 2.98; N, 7.29.

(5-trifluoromethyindol-3-yl)carboxaldehyde (6.35 g, 43%) was prepared from 5-trifluoromethyl-1H-indole to afford from in a similar manner to (5-cyanoindol-3-yl) carboxaldehyde in Example 1. $^1$H NMR (400 MHz, DMSO-d6) 12.5, (1H, br s), 10.0 (1H, s), 8.50 (1H, s), 8.41 (1H, s), 7.73 (1H, d, J=8.6 Hz); MS m/e 212 (M−H)−. Anal calcd. for $C_{10}H_6F_3NO.0.10\ H_2O$: C, 55.88; H, 2.91; N, 6.52. Found: C, 55.82; H, 2.64; N, 6.62.

(5-trifluoromethyl-1-(p-toluenesulfonyl)indol-3-yl) carboxaldehyde (8.40 g, 77%) was prepared from (5-trifluoromethyindol-3-yl)carboxaldehyde in a similar manner to (5-cyano-1-(p-toluenesulfonyl)indol-3-yl) carboxaldehyde in Example 1. $^1$H NMR (400 MHz, DMSO-d6) 10.1 (1H, s), 9.08 (1H, s), 8.41 (1H, s), 8.21 (1H, d, J=8.8 Hz), 8.05 (2H, d, J=8.4 Hz), 7.80 (1H, d, J=8.8 Hz), 7.48 (2H, d, J=8.2 Hz), 2.36 (3H, s); MS m/e 366 (M−H)−. Anal calcd. for $C_{17}H_{12}F_3NO_3S.4.27\ H_2O$: C, 55.58; H, 3.29; N, 3.81. Found: C, 55.42; H, 3.29; N, 3.75.

(E)-[5-trifluoromethyl-1-(p-toluenesulfonyl)indol-3-yl]-N-methoxy-N-methyl-acrylamide (9.01 g, 87%) was prepared from (5-trifluoromethyl-1-(p-toluenesulfonyl)indol-3-yl)carboxaldehyde in a similar manner to (E)-[5-cyano-1-(p-toluenesulfonyl)indol-3-yl]-N-methoxy-N-methylacrylamide in Example 1. $^1$H NMR (400 MHz, DMSO-d6) 8.69 (1H, s), 8.21 (2H, m), 7.97 (2H, d, J=8.4 Hz), 7.76 (2H, m), 7.44 (2H, d, J=8.1 Hz), 7.22 (1H, d, J=16 Hz), 3.78 (3H, s), 3.23 (3H, s), 2.33 (3H, s); MS m/e 453 (M+H)+. Anal calcd. for $C_{21}H_{19}F_3N_2O_4S.0.5\ H_2O$: C, 54.66; H, 4.37; N, 6.07. Found: C, 54.96; H, 4.08; N, 6.05.

Racemic [trans-2-[5-trifluoromethyl-1-(p-toluenesulfonyl)indol-3-yl]cycloprop-1-yl]-N-methoxy-N-methylcarboxamide (5.48 g, 76%) was prepared from (E)-[5-trifluoromethyl-1-(p-toluenesulfonyl)indol-3-yl]-N-methoxy-N-methylacrylamide in a similar manner to [trans-2-[5-cyano-1-(p-toluenesulfonyl)indol-3-yl]cycloprop-1-yl]-N-methyl-carboxamide in Example 1. $^1$H NMR (400 MHz, DMSO-d6) 8.12 (1H, d, J=8.7 Hz), 8.03 (1H, s), 7.90 (2H, d, J=8.4), 7.84 (1H, s), 7.68 (1H, dd, J=8.7, 1.3 Hz), 7.40 (2H, d, J=8.2 Hz), 3.64 (3H, s), 3.16 (3H, s), 2.43 (2H, m), 2.32 (3H, s), 1.44 (2H, m); MS m/e 465 (M−H)−. Anal calcd. for $C_{22}H_{21}F_3N_2O_4S$: C, 56.64; H, 4.53; N, 6.00. Found: C, 56.63; H, 4.60; N, 5.93

Racemic [trans-2-[5-trifluoromethyl-1-(p-toluenesulfonyl)indol-3-yl]-cyclo-propane-carboxaldehyde (4.13 g, 95%) was prepared from racemic [trans-2-[5-trifluoromethyl-1-(p-toluenesulfonyl)indol-3-yl]cycloprop-1-yl]-N-methoxy-N-methyl-carboxamide in a similar manner to [trans-2-[5-cyano-1-(p-toluenesulfonyl)indol-3-yl] cyclopropane-carboxaldehyde in Example 1. $^1$H NMR (400 MHz, DMSO-d6) 9.06 (1H, d, J=5.7 Hz), 8.11 (2H, d, J=8.9 Hz), 7.89 (3H, m), 7.69 (1H, d, J=8.8 Hz), 7.40 (2H, d, J=8.0 Hz), 2.86 (1H, m), 2.32 (3H, s), 2.12 (1H, m), 1.71 (2H, m); MS m/e 406 (M−H)−. Anal calcd. for $C_{20}H_{16}F_3NO_3S$: C, 58.96; H, 3.95; N, 3.43. Found: C, 58.95; H, 3.96; N, 3.28

Racemic [trans-2-[5-trifluoromethylindol-3-yl]-1-(N-methylaminomethyl)cyclo-propane was prepared (two steps, 24% overall yield) from racemic [trans-2-[5-trifluoromethyl-1-(p-toluenesulfonyl)indol-3-yl]-cyclopropane-carboxaldehyde following the procedures outlined for the preparation of (1S,2S)-trans-2-[5-cyanoindol-3-yl]-1-(N-methylaminomethyl)cyclopropane in Example 1. LC-MS (column=Phenomenex Luna C18 S5, 4.6×50 mm, start % B=0, final % B=100, gradient time=3 min, flow rate=5 mL/min) m/e 269 (M+H)+, $t_R$ 1.43 min.

EXAMPLE 155

Methyl-[2-(6-trifluoromethyl-1H-indol-3-yl)-cyclopropylmethyl]-amine

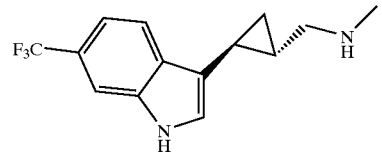

The commercially available (2-nitro-4-trifluoromethylphenyl) acetonitrile (14.0 g, 60.8 mmol) was dissolved in 9:1 EtOH:H2O (50 mL) and glacial acetic acid (1.4 mL). This mixture was hydrogenated over 10% Pd/C (5.0 g) at 50 psi for 16 h at room temperature. The reaction was filtered over celite and evaporated in vacuo. The residue was partitioned between saturated aqueous sodium carbonate and dichloromethane (2×200 mL) and the combined organic extract was dried over sodium sulfate, filtered, and concentrated in vacuo. The crude material was purified by silica gel column chromatography (hexanes/ethyl acetate, 20:1, 9:1, 5:1) to afford 12.9 g (65% yield) of 6-trifluoromethyl-1H-indole as a yellow solid: $^1$H NMR (400 MHz, CDCl3) 8.36, (1H, br s), 7.72 (2H, m), 7.37 (2H, m), 6.63 (1H, m); MS m/e 184 (M–H)⁻. Anal calcd. for C₉H₆F₃N: C, 58.38; H, 3.26; N, 7.56. Found: C, 58.30; H, 2.92; N, 7.49.

(6-trifluoromethyindol-3-yl)carboxaldehyde was prepared in 48% yield from 6-trifluoromethyl-1H-indole in a similar manner to (5-cyanoindol-3-yl)carboxaldehyde in Example 1. ¹H NMR (400 MHz, DMSO-d₆) 12.5, (1H, br s), 10.0 (1H, s), 8.52 (1H, s), 8.28 (1H, d, J=8.3 Hz), 7.86 (1H, s), 7.54 (1H, d, J=8.3 Hz); MS m/e 212 (M–H)⁻. Anal calcd. for C₁₀H₆F₃NO: C, 56.34; H, 2.83; N, 6.57. Found: C, 56.23; H, 2.76; N, 6.61.

(6-trifluoromethyl-1-(p-toluenesulfonyl)indol-3-yl)carboxaldehyde was prepared in a 93% yield from (6-trifluoromethyindol-3-yl)carboxaldehyde in a similar manner to (5-cyano-1-(p-toluenesulfonyl)indol-3-yl)carboxaldehyde in Example 1. ¹H NMR (400 MHz, DMSO-d₆) 10.1 (1H, s), 9.13 (1H, s), 8.33 (1H, d, J=8.3 Hz), 8.19 (1H, s), 8.05 (2H, d, J=8.4 Hz), 7.77 (1H, d, J=8.3 Hz), 7.49 (2H, d, J=8.2 Hz), 2.35 (3H, s); MS m/e 366 (M–H)⁻. Anal calcd. for C₁₇H₁₂F₃NO₃S: C, 55.58; H, 3.29; N, 3.81. Found: C, 55.48; H, 3.42; N, 3.82.

(E)-[6-trifluoromethyl-1-(p-toluenesulfonyl)indol-3-yl]-N-methoxy-N-methylacrylamide was prepared in an 85% yield from (6-trifluoromethyl-1-(p-toluenesulfonyl)indol-3-yl)carboxaldehyde in a similar manner to (E)-[5-cyano-1-(p-toluenesulfonyl)indol-3-yl]-N-methoxy-N-methylacrylamide in Example 1. ¹H NMR (400 MHz, DMSO-d₆) 8.75 (1H, s), 8.21 (1H, s), 8.13 (1H, d, J=8.4 Hz), 7.96 (2H, d, J=8.4 Hz), 7.73 (2H, m), 7.45 (2H, d, J=8.2 Hz), 7.22 (1H, d, J=16 Hz), 3.78 (3H, s), 3.23 (3H, s), 2.33 (3H, s); MS m/e 451 (M–H)⁻. Anal calcd. for C₂₁H₁₉F₃N₂O₄S: C, 55.74; H, 4.23; N, 6.19. Found: C, 55.78; H, 4.13; N, 6.13.

Racemic [trans-2-[6-trifluoromethyl-1-(p-toluenesulfonyl)indol-3-yl]cycloprop-1-yl]-N-methoxy-N-methylcarboxamide was prepared in an 83% yield from (E)-[6-trifluoromethyl-1-(p-toluenesulfonyl)indol-3-yl]-N-methoxy-N-methylacrylamide in a similar manner to [trans-2-[5-cyano-1-(p-toluenesulfonyl)indol-3-yl]cycloprop-1-yl]-N-methoxy-N-methylcarboxamide in Example 1. ¹H NMR (400 MHz, DMSO-d₆) 8.15 (1H, s), 7.89 (4H, m), 7.62 (1H, dd, J=8.3, 1.1 Hz), 7.41 (2H, d, J=8.1 Hz), 3.64 (3H, s), 3.16 (3H, s), 2.41 (2H, m), 2.32 (3H, s), 1.50 (1H, br s), 1.42 (1H, m); MS m/e 465 (M–H)⁻. Anal calcd. for C₂₂H₂₁F₃N₂O₄S: C, 56.64; H, 4.53; N, 6.00. Found: C, 56.56; H, 4.46; N, 5.95

Racemic [trans-2-[6-trifluoromethyl-1-(p-toluenesulfonyl)indol-3-yl]-cyclopropane-carboxaldehyde was prepared in an 89% yield from racemic [trans-2-[6-trifluoromethyl-1-(p-toluenesulfonyl)indol-3-yl]cycloprop-1-yl]-N-methoxy-N-methyl-carboxamide in a similar manner to [trans-2-[5-cyano-1-(p-toluenesulfonyl)indol-3-yl]cyclopropane-carboxaldehyde in Example 1. ¹H NMR (400 MHz, DMSO-d₆) 9.12 (1H, d, J=5.4 Hz), 8.15 (1H, s), 7.92 (4H, m), 7.64 (1H, dd, J=8.3, 1.1 Hz), 7.41 (2H, d, J=8.1 Hz), 2.78 (1H, m), 2.32 (3H, s), 2.15 (1H, m), 1.71 (2H, m); MS m/e 406 (M–H)⁻. Anal calcd. for C₂₀H₁₆F₃NO₃S: C, 58.96; H, 3.95; N, 3.43. Found: C, 58.93; H, 3.93; N, 3.25.

Racemic [trans-2-[6-trifluoromethylindol-3-yl]-1-(N-methylaminomethyl)cyclopropane was prepared in two steps and 56% overall yield from racemic [trans-2-[6-trifluoromethyl-1-(p-toluenesulfonyl)indol-3-yl]-cyclopropane-carboxaldehyde following the procedures outlined for the preparation of (1S,2S)-trans-2-[5-cyanoindol-3-yl]-1-(N-methylaminomethyl)cyclopropane in Example 1. LC-MS (column=Phenomenex Luna C18 S5, 4.6×50 mm, start % B=0, final % B=100, gradient time=3 min, flow rate=5 mL/min) m/e 269 (M+H)⁺, t_R 1.43 min.

EXAMPLE 156

Ethyl-[2-(6-trifluoromethyl-1H-indol-3-yl)-cyclopropylmethyl]-amine

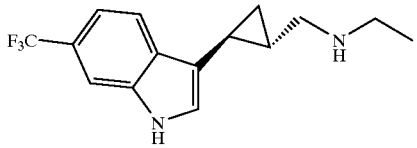

Racemic [trans-2-[6-trifluoromethylindol-3-yl]-1-(N-ethylaminomethyl)-cyclo-propane was prepared in 49% overall yield in a manner similar to the above example. LC-MS (column=Phenomenex Luna C18 S5, 4.6×50 mm, start % B=0, final % B=100, gradient time=3 min, flow rate=5 mL/min) m/e 283 (M+H)⁺, t_R 1.46 min.

EXAMPLE 157

Benzyl-methyl-[2-(6-trifluoromethyl-1H-indol-3-yl)-cyclopropylmethyl]-amine

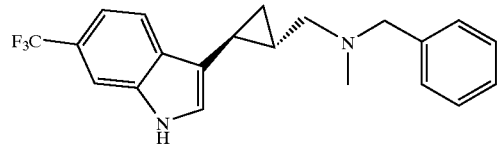

Racemic [trans-2-[6-trifluoromethylindol-3-yl]-1-(N-benzyl-N-methylaminomethyl)-cyclopropane was prepared in 78% overall yield in a manner similar to the above example. LC-MS (column=Phenomenex Luna C18 S5, 4.6×50 mm, start % B=0, final % B=100, gradient time=3 min, flow rate=5 mL/min) m/e 359 (M+H)⁺, t_R 1.64 min.

EXAMPLE 158

3-(2-Methylaminomethyl-cyclopropyl)-1H-indole-6-carbonitrile

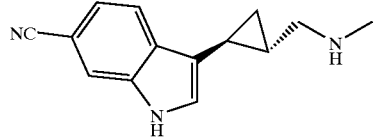

A mixture of 3-nitro-p-tolunitrile (30.0 g, 185 mmol), DMF (100 mL), and dimethylformamide dimethylamine (24.3 g, 204 mmol) was heated to 110° C. for 16 h. The deep red solution was poured into H₂O (1 L) and extracted with EtOAc (4×250 mL). The organic layers were washed with H₂O, brine, dried over sodium sulfate, filtered, and concentrated in vacuo. The solid residue was triturated with hexanes to give 4-(2-dimethylamino-vinyl)-3-nitro-benzonitrile (28.5 g, 74%) after filtration. ¹H NMR (400 MHz, DMSO-d₆) 8.22 (1H, s), 7.83 (2H, m), 7.65 (1H, m), 5.67 (1H, d, J=13 Hz), 2.98 (6H, s); MS m/e 219 (M+H)⁺. Anal calcd. for C₁₁H₁₁N₃O₂: C, 60.82; H, 5.10; N, 19.34. Found: C, 60.54; H, 4.99; N, 19.40.

4-(2-Dimethylamino-vinyl)-3-nitro-benzonitrile (28.5 g, 131 mmol) was dissolved in MeOH (850 mL) and hydrogenated over 10% Pd/C (6.0 g) at 60 psi for 1.5 h at room temperature. The reaction was filtered over celite and evaporated in vacuo. The residue was partitioned between 5% aqueous HCl solution and $Et_2O$ (2×200 mL) and the combined organic extract was washed with brine, dried over sodium sulfate, filtered, and concentrated in vacuo to give 6-cyano-$^1$H-indole (13.5 g, 72%) as a light brown solid. $^1$H NMR (400 MHz, DMSO-$d_6$) 11.7 (1H, br s), 7.89 (1H, s), 7.72 (1H, d, J=8.2 Hz), 7.65 (1H, m), 7.32 (1H, m), 6.59 (1H, m); MS m/e 141 (M−H)$^-$. Anal calcd. for $C_9H_6N_2$.0.10 $H_2O$ : C, 75.09; H, 4.34; N, 19.46. Found: C, 74.92; H, 4.29; N, 19.34.

(6-Cyanoindol-3-yl)carboxaldehyde was prepared in 64% yield from 6-cyano-1H-indole in a similar manner to (5-cyanoindol-3-yl)carboxaldehyde in Example 1. $^1$H NMR (400 MHz, DMSO-$d_6$) 12.5, (1H, br s), 10.0 (1H, s), 8.55 (1H, m), 8.23 (1H, d, J=8.2 Hz), 8.04 (1H, m), 7.58 (1H, dd, J=8.2, 1.4 Hz); MS m/e 169 (M−H)$^-$. Anal calcd. for $C_{10}H_6N_2O$.0.10 $H_2O$ : C, 69.84; H, 3.63; N, 16.29. Found: C, 69.68; H, 3.54; N, 16.36.

(6-cyano-1-(p-toluenesulfonyl)indol-3-yl)carboxaldehyde was prepared in an 88% yield from (6-cyanoindol-3-yl)carboxaldehyde in a similar manner to (5-cyano-1-(p-toluenesulfonyl)indol-3-yl)carboxaldehyde in Example 1. $^1$H NMR (400 MHz, DMSO-$d_6$) 10.1 (1H, s), 9.14 (1H, s), 8.46 (1H, s), 8.27 (1H, d, J=8.2 Hz), 8.16 (2H, d, J=8.4 Hz), 7.81 (1H, dd, J=8.2, 1.3 Hz), 7.48 (2H, d, J=8.2 Hz), 2.36 (3H, s); MS m/e 323 (M−H)$^-$.

(E)-[6-cyano-1-(p-toluenesulfonyl)indol-3-yl]-N-methoxy-N-methylacrylamide was prepared in a 77% yield from (6-cyano-1-(p-toluenesulfonyl)indol-3-yl)carboxaldehyde in a similar manner to (E)-[5-cyano-1-(p-toluenesulfonyl)indol-3-yl]-N-methoxy-N-methylacrylamide in Example 1. $^1$H NMR (300 MHz, DMSO-$d_6$) 8.77 (1H, s), 8.42 (1H, m), 8.07 (3H, dd, J=8.5, 2.4 Hz), 7.73 (2H, m), 7.45 (2H, d, J=8.2 Hz), 7.20 (1H, d, J=16 Hz), 3.77 (3H, s), 3.23 (3H, s), 2.34 (3H, s); MS m/e 408 (M−H)$^-$. Anal calcd. for $C_{21}H_{19}N_3O_4S$: C, 61.60; H, 4.67; N, 10.26. Found: C, 61.43; H, 4.56; N, 10.05.

Racemic [trans-2-[6-cyano-1-(p-toluenesulfonyl)indol-3-yl]cycloprop-1-yl]-N-methoxy-N-methylcarboxamide was prepared in a 64% yield from (E)-[6-cyano-1-(p-toluenesulfonyl)indol-3-yl]-N-methoxy-N-methylacrylamide in a similar manner to [trans-2-[5-cyano-1-(p-toluenesulfonyl)indol-3-yl]cycloprop-1-yl]-N-methoxy-N-methylcarboxamide in Example 1. $^1$H NMR (400 MHz, DMSO-$d_6$) 8.33 (1H, d, J=1.0 Hz), 7.98 (3H, m), 7.83 (1H, m), 7.67 (1H, dd, J=8.2, 1.3 Hz), 7.41 (2d, J=8.1 Hz), 3.63 (3H, s), 3.15 (3H, s), 2.40 (2H, m), 2.33 (3H, s), 1.45 (2H, m); MS m/e 422 (M−H)$^-$. Anal calcd. for $C_{22}H_{21}N_3O_4S$: C, 62.39; H, 4.99; N, 9.92. Found: C, 62.15; H, 4.78; N, 9.84.

Racemic [trans-2-[6-cyano-1-(p-toluenesulfonyl)indol-3-yl]-cyclopropane carboxaldehyde was prepared in a 37% yield from racemic [trans-2-[6-cyano-1-(p-toluenesulfonyl)indol-3-yl]cycloprop-1-yl]-N-methoxy-N-methylcarboxamide in a similar manner to [trans-2-[5-cyano-1-(p-toluenesulfonyl)indol-3-yl]cyclopropane-carboxaldehyde in Example 1. $^1$H NMR (400 MHz, DMSO-$d_6$) 9.11 (1H, d, J=5.5 Hz), 8.33 (1H, d, J=1.0 Hz), 7.99 (3H, m), 7.88 (1H, d, J=8.1 Hz), 7.69 (1H, dd, J=8.2, 1.4 Hz), 7.41 (2H, d, J=8.0 Hz), 2.76 (1H, m), 2.33 (3H, s), 2.14 (1H, m), 1.70 (2H, m); MS m/e 363 (M−H)$^-$. Anal calcd. for $C_{20}H_{16}N_2O_3S$: C, 65.91; H, 4.42; N, 7.68. Found: C, 65.91; H, 4.45; N, 7.47.

Racemic [trans-2-[6-cyanoindol-3-yl]-1-(N-methylaminomethyl)cyclopropane was prepared in two steps and 33% overall yield from racemic [trans-2-[6-cyano-1-(p-toluenesulfonyl)indol-3-yl]-cyclopropane-carboxaldehyde following the procedures outlined for the preparation of (1S,2S)-trans-2-[5-cyanoindol-3-yl]-1-(N-methylaminomethyl)-cyclopropane in Example 1. LC-MS (column=Phenomenex Luna C18 S5, 4.6×50 mm, start % B=0, final % B=100, gradient time=3 min, flow rate=5 mL/min) m/e 266 (M+H)$^+$, $t_R$ 1.07 min.

EXAMPLE 159

3-(2-Ethylaminomethyl-cyclopropyl)-1H-indole-6-carbonitrile

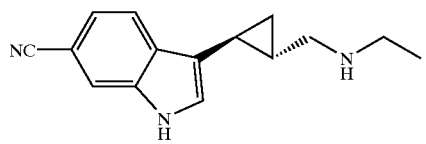

Racemic [trans-2-[6-cyanoindol-3-yl]-1-(N-ethylaminomethyl)-cyclopropane was prepared in 35% overall yield in a manner similar to the above example. LC-MS (column=Phenomenex Luna C18 S5, 4.6×50 mm, start % B=0, final % B=100, gradient time=3 min, flow rate=5 mL/min) m/e 240 (M+H)$^+$, $t_R$ 1.08 min.

EXAMPLE 160

3-(2-Diethylaminomethyl-cyclopropyl)-1H-indole-6-carbonitrile

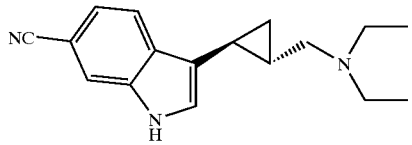

Racemic [trans-2-[6-cyanoindol-3-yl]-1-(N,N-diethylaminomethyl)-cyclopropane was prepared in 60% overall yield in a manner similar to the above example. LC-MS (column=Phenomenex Luna C18 S5, 4.6×50 mm, start % B=0, final % B=100, gradient time=3 min, flow rate=5 mL/min) m/e 268 (M+H)$^+$, $t_R$ 1.10 min.

EXAMPLE 161

3-{2-[(Ethyl-methyl-amino)-methyl]-cyclopropyl}-1H-indole-6-carbonitrile

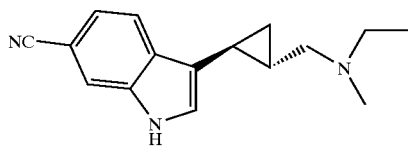

Racemic [trans-2-[6-cyanoindol-3-yl]-1-(N-ethyl-N-methylaminomethyl)-cyclo-propane was prepared in 55% overall yield in a manner similar to the above example. LC-MS (column=Phenomenex Luna C18 S5, 4.6×50 mm, start % B=0, final % B=100, gradient time=3 min, flow rate=5 mL/min) m/e 254 (M+H)$^+$, $t_R$ 1.05 min.

EXAMPLE 162

3-{2-[(Benzyl-methyl-amino)-methyl]-cyclopropyl}-1H-indole-6-carbonitrile

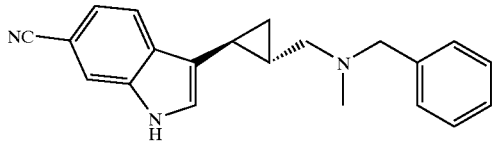

Racemic [trans-2-[6-cyanoindol-3-yl]1-(N-benzyl-N-methylaminomethyl)-cyclopropane was prepared in 70% overall yield in a manner similar to the above example. LC-MS (column=Phenomenex Luna C18 S5, 4.6×50 mm, start % B=0, final % B=100, gradient time=3 min, flow rate=5 mL/min) m/e 316 (M+H)$^+$, $t_R$ 1.34 min.

EXAMPLE 163

3-(2-Dimethylaminomethyl-cyclopropyl)-1H-indazole-5-carbonitrile

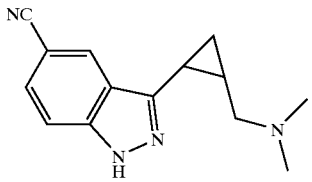

n-BuLi (1.9 M, 26.3 mL, 50 mmol) was added dropwise to a solution of diisopropylamine (7.71 mL, 55 mmol) in 100 mL anhydrous THF under $N_2$ at 0° C. After 10 minutes, the reaction was cooled to −78° C. A solution of 4-fluorobenzonitrile (6.06 g, 50 mmol) in 20 mL anhydrous THF was added dropwise, at such a rate to maintain an internal temperature of −78° C. After stirring for 1 h at this temperature, trimethyl borate (8.41 mL, 75 mmol) was added dropwise at such a rate to maintain an internal temperature of −78° C. The reaction was stirred and gradually warmed to room temperature over 16 h. The reaction was cooled to 10° C. and 25 mL 6N HCl was added. After stirring at room temperature for 4 h, the reaction was partitioned between water and ethyl acetate. The organic layer was washed three times with 100 mL 2N NaOH. The aqueous layers were pooled and adjusted to pH 6 with 6N HCl. The white solid which forms was extracted by three washes of 100 mL Ethyl acetate. The organic layers were pooled, dried over sodium sulfate, concentrated and dried under high vacuum to give 2-fluoro-5-cyanophenyl boronic acid (5.74 g, 70%). $^1$H NMR (500 MHz, acetone-d6) 8.08 (1H, dd, J=2.14, 5.5 Hz), 7.90 (1H, m), 7.31 (1H, t, J=8.85 Hz). Anal. calcd. for $C_7H_5BFNO_2$: C, 50.97; H, 3.05; N, 8.49. Found: C, 51.19; H, 3.19; N, 8.26.

To a solution of 2-chlorocarbonyl-cyclopropanecarboxylic acid ethyl ester (5.30 g, 30 mmol) and 4-methylbenzene thiol (3.73 g, 30 mmol) in 150 mL hexane at 0° C. was added a solution of $Et_3N$ in 25 mL hexane dropwise. The reaction was warmed to room temperature and stirred for 3 h. The solid precipitate was removed by filtration and washed with hexane. The filtrate was concentrated in vacuo to give 7.88 g (99%) of 2-p-tolylsulfanylcarbonyl-cyclopropanecarboxylic acid ethyl ester as an oil: $^1$H NMR (500 MHz, CDCl3) 7.30 (2H, d, J=7.93 Hz), 7.22 (2H, d, J=7.93 Hz), 4.17 (2H, q, J=7.02 Hz), 2.60 (1H, m), 2.37 (3H, s), 2.31 (1H, m), 1.54 (2H, m), 1.29 (3H, t, J=7.02 Hz). MS m/e 262.92 (M−H)$^-$. Anal. calcd. for $C_{14}H_{16}O_3S$: C, 63.61; H, 6.10. Found: C, 63.68; H, 6.17.

To a mixture of 2-fluoro-5-cyanophenyl boronic acid (3.10 g, 18.8 mmol), 2-p-tolylsulfanylcarbonyl-cyclopropanecarboxylic acid ethyl ester (3.30 g, 12.5 mmol), copper thiophene-2-carboxylate (3.58 g, 18.8 mmol), tris(dibenzylideneacetone)-dipalladium(0).CHCl$_3$ adduct (150 mg, 0.14 mmol), and tri-2-furyl phosphine (0.86 mmol) under $N_2$ was added 125 mL anhydrous THF. The reaction was stirred for 4 h, then poured into 500 mL water and extracted with 500 mL $Et_2O$. The organic layer was extracted with 0.1 N HCl, water, saturated NaHCO$_3$, and water. The organic extract was dried over sodium sulfate, concentrated, and purified by flash chromatography on silica gel using ethyl acetate/hexane (0–10%) as the eluent to yield 2-(5-cyano-2-fluoro-benzoyl)-cyclopropanecarboxylic acid ethyl ester (2.17 g, 66%). $^1$H NMR (500 MHz, CDCl3) 8.09 (1H, dd, J=2.14, 6.41 Hz), 7.83 (1H, m), 7.31 (1H, dd, J=8.55, 10.07 Hz), 4.18 (2H, q, J=7.02 Hz), 3.10 (1H, m), 2.42 (1H, m), 1.68 (2H, m), 1.28 (3H, t, J=7.02 Hz). Anal. calcd. for $C_{14}H_{12}FNO_3$: C, 64.36; H, 4.63; N, 5.36. Found: C, 64.62; H, 4.53; N, 5.26.

2-(5-cyano-2-fluoro-benzoyl)-cyclopropanecarboxylic acid ethyl ester (1.62 g, 6.2 mmol) and p-toluenesulfonhydrazide (2.31 g, 12.4 mmol) were refluxed in 50 mL ethanol for 36 h. The reaction was concentrated in vacuo, then purified by flash chromatography on silica gel using ethyl acetate/hexane (0–25%) as the eluent to give 2-[1-(5-cyano-2-fluoro-phenyl)-2-(toluene-4-sulfonylamino)-vinyl]-cyclopropanecarboxylic acid ethyl ester (1.77 g, 66%) as a mixture of cis and trans isomers. $^1$H NMR (500 MHz, CDCl3) 7.87 (1H, d, J=8.24 Hz), 7.78 (0.5H, m), 7.76 (1H, d, J=8.24 Hz), 7.65 (0.5H, m), 7.61 (0.5H, dd, J=2.14, 6.71 Hz), 7.44 (0.5H, dd, J=2.14, 5.80 Hz), 7.36 (2H, dd, J=3.96, 7.93 Hz), 7.31 (0.5H, t, J=8.54 Hz), 7.18 (0.5H, t, J=8.54 Hz), 4.22 (1H, m), 4.12 (2H, dq, J=7.32, 4.27 Hz), 2.46 (3H, 2s), 2.20 (0.5H, m), 1.99 (0.5H, m), 1.66 (0.5H, m), 1.43 (0.5H, m), 1.31 (2H, m), 1.27 (3H, dt, J=7.02, 3.67 Hz). MS m/e 430.13 (M+H)$^+$.

2-[1-(5-Cyano-2-fluoro-phenyl)-2-(toluene-4-sulfonylamino)-vinyl]-cyclo-propane-carboxylic acid ethyl ester (1.84 g, 4.3 mmol) and $K_2CO_3$ (1.8 g, 13 mmol) were stirred in 10 mL anhydrous DMF for 15 minutes. The reaction was poured into 150 mL saturated $Na_2CO_3$ solution and extracted three time times with 75 mL Ethyl acetate. The organic layers were pooled and extracted three times with 75 mL brine, then dried over $Mg_2SO_4$. Flash chromatography on silica gel with a step gradient of 0–15% Ethyl acetate in hexane yielded 2-(1-benzenesulfonyl-5-cyano-1H-indazol-3-yl)-cyclopropanecarboxylic acid ethyl ester (796 mg, 45%). $^1$H NMR (500 MHz, CDCl3) 8.27 (1H, d, J=8.86 Hz), 8.07 (1H, s), 7.83 (2H, d, J=8.24 Hz), 7.76 (1H, dd, J=8.85, 1.52 Hz), 7.28 (2H, d, J=8.24 Hz), 4.2 (2H, q, J=7.02 Hz), 2.71 (1H, m), 2.39 (3H, s), 2.30 (1H, m), 1.67 (2H, m), 1.29 (3H, t, J=7.02 Hz). MS m/e 410.0 (M+H)$^+$. Anal. calcd. for $C_{21}H_{19}N_3O_4S$: C, 61.60; H, 4.67; N, 10.26. Found: C, 61.63; H, 4.89; N, 10.07.

2-(1-Benzenesulfonyl-5-cyano-1H-indazol-3-yl)-cyclopropanecarboxylic acid ethyl ester (1.12 g, 2.74 mmol) was dissolved in 30 mL anhydrous THF under $N_2$ and cooled to −40° C. LAH (0.83 g, 22 mmol) was added portionwise over a 15 min. period. The reaction was stirred for 5 h at −40° C., then quenched with 50 mL ethyl acetate, followed by 10 mL water. After stirring at room temperature for 30 min, 50 mL saturated tartrate solution was added and stirred for 30 min. The precipitate was removed by filtration and washed with ethyl acetate. The precipitate was washed with more ethyl acetate, and the organic layer was washed with brine and dried over $Na_2SO_4$. Flash chromatography on silica gel using ethyl acetate/hexane (25–50%) as the eluent gave 3-(2-hydroxymethyl-cyclopropyl)-1-(toluene-4-sulfonyl)-1H-indazole-5-carbonitrile (580 mg, 58%). $^1$H NMR (500 MHz, CDCl3) 8.26 (1H, d, J=8.85 Hz), 8.08 (1H, s), 7.83 (2H, d, J=8.24 Hz), 7.74 (1H, dd, J=8.85, 1.22 Hz), 7.27 (2H, d, J=8.24 Hz), 3.78 (1H, dd, J=11.29, 6.10 Hz), 3.61 (1H, dd, 11.29, 6.71 Hz), 2.38 (3H, s), 2.10 (1H, p, J=4.88 Hz), 1.82 (1H, m), 1.39 (1H, dt, J=8.55, 4.88 Hz), 1.11 (1H, dt, J=8.55, 4.88 Hz). MS m/e 366.15 (M–H)$^-$. Anal. calcd. for $C_{19}H_{17}N_3O_3S$: C, 62.11; H, 4.66; N, 11.43. Found: C, 62.16; H, 4.76; N, 11.19.

Anhydrous DMSO (0.20 mL, 2.8 mmol) was added dropwise to a solution of oxalyl chloride (0.21 mL, 2.4 mmol) in 20 mL anhydrous $CH_2Cl_2$ under $N_2$ at −78° C. and stirred for 30 min. A solution of 3-(2-hydroxymethyl-cyclopropyl)-1-(toluene-4-sulfonyl)-1H-indazole-5-carbonitrile (634 mg, 1.63 mmol) in 20 mL anhydrous $CH_2Cl_2$ was then added and stirring continued for 40 min. at −78° C. $Et_3N$ (1.25 mL, 8.98 mmol) was added and stirring continued for 10 min at −78° C. The reaction was warmed to room temperature and 25 mL water was added. The layers were partitioned, and the aqueous layer was extracted with $CH_2Cl_2$. The organic layers were pooled, extracted with brine, and dried over $MgSO_4$, and concentrated in vacuo to give 3-(2-formyl-cyclopropyl)-1-(toluene-4-sulfonyl)-1H-indazole-5-carbonitrile (637 mg, 100%). $^1$H NMR (500 MHz, CDCl3) 9.54 (1H, d, J=3.66 Hz), 8.20 (1H, d, J=8.85 Hz), 8.05 (1H, s), 7.83 (2H, d, J=8.24 Hz), 7.77 (1H, dd, J=8.85, 1.53 Hz), 7.29 (2H, d, J=8.24 Hz), 2.82 (1H, m), 2.62 (1H, m), 2.39 (3H, s), 1.82 (2H, m).

3-(2-Formyl-cyclopropyl)-1-(toluene-4-sulfonyl)-1H-indazole-5-carbonitrile (74 mg, 0.2 mmol) was dissolved in 2 mL ethanol and 2 mL THF, and to this was added a 2.0 M solution of dimethylamine in THF (1.0 mL, 2.0 mmol). After stirring for 5 min, sodium triacetoxyborohydride (170 mg, 0.8 mmol) was added the reaction continued for 2 h. At this point, 1 mL water, 1 mL 50% NaOH, and 2 mL MeOH were added and stirring continued for 30 min. The reaction was then diluted with 20 mL water and extracted three times with 30 mL ethyl acetate. The organic layers were pooled, washed with brine, dried over $Na_2SO_4$, and concentrated in vacuo. Purification by preparative reverse phase HPLC gave 3-(2-dimethylaminomethyl-cyclopropyl)-1H-indazole-5-carbonitrile as an oily trifluoroacetic acid salt (54 mg, 76%). $^1$H NMR (500 MHz, d4-MeOH) 8.33 (1H, s), 7.59 (2H, s), 3.31 (2H, d, J=7.63 Hz), 2.97 (6H, d, J=2.74 Hz), 2.48 (1H, m), 1.84 (1H, m), 1.47 (1H, dt, J=8.55, 5.19 Hz), 1.24 (1H, dt, J=8.85, 5.19). LC-MS: 0.73 min; 241.17 (MH)+.

EXAMPLE 164

3-{2-[(Ethyl-methyl-amino)-methyl]-cyclopropyl}-1H-indazole-5-carbonitrile

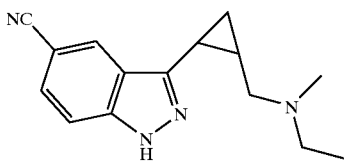

3-{2-[(Ethyl-methyl-amino)-methyl]-cyclopropyl}-1H-indazole-5-carbonitrile was prepared (54 mg, 73%) in a manner and scale similar to the above example. $^1$H NMR (500 MHz, d4-MeOH) 8.34 (1H, s), 7.61 (2H, s), 3.38 (2H, m), 3.24 (2H, m), 2.94 (3H, d, J=2.44 Hz), 2.48 (1H, m), 1.84 (1H, m), 1.48 (1H, dt, J=8.85, 5.19 Hz), 1.36 (3H, t, J=7.33 Hz), 1.25 (1H, m). LC-MS: 0.78 min; 255.17 (MH)+.

EXAMPLE 165

3-(2-Diethylaminomethyl-cyclopropyl)-1H-indazole-5-carbonitrile

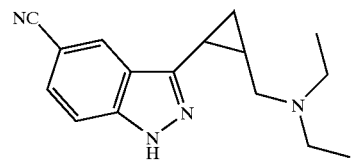

3-(2-Diethylaminomethyl-cyclopropyl)-1H-indazole-5-carbonitrile was prepared (45 mg, 59%) in a manner and scale similar to the above example. $^1$H NMR (500 MHz, d4-MeOH) 8.34 (1H, s), 7.60 (2H, s), 3.33 (6H, m), 2.49 (1H, m), 1.83 (1H, m), 1.47 (1H, dt, J=8.54, 5.19 Hz), 1.36 (6H, t, J=7.32 Hz), 1.25 (1H, m).

LC-MS: 0.82 min; 269.19 (MH)$^+$.

EXAMPLE 166

3-(2-Pyrrolidin-1-ylmethyl-cyclopropyl)-1H-indazole-5-carbonitrile

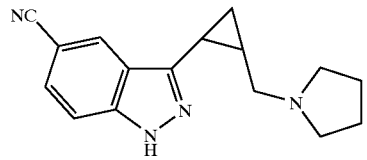

3-(2-Pyrrolidin-1-ylmethyl-cyclopropyl)-1H-indazole-5-carbonitrile was prepared (41 mg, 54%) in a manner and scale similar to the above example. $^1$H NMR (500 MHz, d4-MeOH) 8.34 (1H, s), 7.60 (2H, s), 3.72 (2H, m), 3.36 (2H, d, J=7.32 Hz), 3.18 (2H, m), 2.48 (1H, m), 2.17 (2H, m), 2.03 (2H, m), 1.86 (1H, m), 1.45 (1H, dt, J=8.55, 5.19 Hz), 1.24 (1H, m). LC-MS: 0.79 min; 267.18 (MH)+.

EXAMPLE 167

(2-Benzo[b]thiophen-3-yl-cyclopropylmethyl)-dimethyl-amine

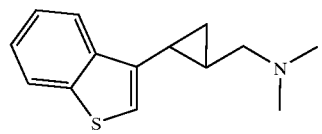

Diethyl (N-methoxy-N-methylcarbamoylmethyl) phosphonate (6.13 g, 25.6 mmol) was added dropwise via syringe to a stirred suspension of sodium hydride (1.02 g, 25.6 mmol) in anhydrous THF (75 ml) at 0° C. The reaction was warmed to room temperature and was stirred for 1 h. After cooling to 0° C., benzo[b]thiophene-3-carbaldehyde (3.78 g, 23.3 mmol) was added. The resulting mixture was stirred at room temperature for 1 hr. The reaction was quenched with 100 mL aqueous HCl (0.1 N) and extracted with ethyl acetate (250 ml). The combined organic layers were washed with brine (50 ml) and dried over anhydrous magnesium sulfate. The filtrate was concentrated in vacuo and triturated with hexane to give (E)-3-benzo[b]thiophen-3-yl-N-methoxy-N-methyl-acrylamide (5.38 g, 93%) as a yellow solid. $^1$H NMR (500 MHz, CDCl$_3$) 8.06–8.01 (2H, 2 superimposed d, J=8.24, 15.87 Hz), 7.89 (1H, d, J=7.94 Hz), 7.78 (1H, s), 7.47 (1H, t, J=7.93 Hz), 7.41 (1H, t, J=8.24 Hz), 7.13 (1H, d, J=15.87 Hz), 3.79 (3H, s), 3.34 (3H, s); MS m/e 248.07 (M+H)$^+$.

The following procedure was carried out behind a safety shield using plastic coated glassware free of scratches and ground glass joints. 1-Methyl-3-nitro-1-nitrosoguanidine (14.4 g, 98 mmol) was carefully added portionwise over 30 min to a Erlenmeyer flask containing a swirled mixture of aqueous sodium hydroxide (100 ml, 5 N) and diethyl ether (250 ml) at 0° C. After vigorous bubbling had ceased, the organic layer (containing diazomethane) was decanted into a chilled (0° C.) Erlemneyer flask containing potassium hydroxide chips (20 g). The mixture was swirled for 10 min and the yellow solution was decanted into a dropping funnel. The solution of diazomethane was added over 30 min to an open flask containing a stirred mixture of (E)-3-benzo[b]thiophen-3-yl-N-methoxy-N-methyl-acrylamide (4.85 g, 19.6 mmol) and palladium acetate (170 mg, 0.76 mmol) in dichloromethane (200 ml) maintained at 0° C. After stirring for 1 h, a second batch of freshly prepared diazomethane (98 mmol) in ~250 ml of diethyl ether was added over 30 min. After stirring for 18 h, the reaction was quenched with glacial acetic acid (4 ml) and poured into an aqueous saturated solution of sodium bicarbonate (250 ml). The aqueous layer was extracted with ethyl acetate (3×100 ml). The organic layers were washed with brine, dried over anhydrous magnesium sulfate, and concentrated in vacuo. The crude product was purified by flash chromatography on silica gel with a step gradient of 10–25% ethyl acetate in hexane to give, after concentration and drying under high vacuum, 2-benzo[b]thiophen-3-yl-cyclopropanecarboxylic acid methoxy-methyl-amide (3.51 g, 69%). $^1$H NMR (500 MHz, CDCl$_3$) 7.90 (1H, d, J=7.32 Hz), 7.84 (1H, d, J=7.33 Hz), 7.39 (2H, m), 7.05 (1H, s), 3.71 (3H, s), 3.28 (3H, s), 2.71 (1H, m), 2.41 (1H, m), 1.66 (1H, m), 1.37 (1H, m); MS m/e 262.10 (M+H)$^+$.

Powdered lithium aluminum hydride (3.05 g, 80.4 mmol) was carefully added portionwise to a stirred solution of 2-benzo[b]thiophen-3-yl-cyclopropanecarboxylic acid methoxy-methyl-amide (3.50 g, 13.4 mmol) in anhydrous tetrahydrofuran (300 ml) at −40° C. under N$_2$. The resulting mixture was stirred at −40° C. for 3 h. The reaction was quenched with ethyl acetate (100 ml) and allowed to warmed to room temperature. After 20 min, water (5 ml) was added followed by a solution of aqueous sodium hydroxide (5N, 5 ml). After stirring for 30 min at room temperature the aluminum salts were removed by vacuum filtration. The salts were washed with ethyl acetate (100 ml) and the combined filtrates were concentrated in vacuo. The crude material was purified by silica gel column chromatography (10% ethyl acetate in hexane) to give trans-2-benzo[b]thiophen-3-yl-cyclopropanecarbaldehyde (2.02 g, 75%). $^1$H NMR (500 MHz, CDCl3) 9.48 (1H, d, J=4.57 Hz), 7.84 (2H, dd, J=17.09, 7.33 Hz), 7.41 (2H, m), 2.80 (1H, m), 2.17 (1H, m), 1.78 (1H, m), 1.59 (1H, m); MS m/e 203.22 (M+H)$^+$.

Trans-2-benzo[b]thiophen-3-yl-cyclopropanecarbaldehyde (202 mg, 1.0 mmol) was dissolved in 10 mL ethanol. To this solution was added a 2.0 M solution of dimethylamine in THF (5.0 mL, 10.0 mmol). After stirring for 15 min, sodium triacetoxyborohydride (850 mg, 4.0 mmol) was added and the reaction continued for 1 h. The reaction was diluted with 10 mL 0.1 N HCl, then solid sodium bicarbonate was added in portions to adjust pH to 7. The mixture was extracted with ethyl acetate (2×20 mL), and the organic extracts were pooled, washed with brine, dried over sodium sulfate, and concentrated in vacuo. Purification by preparative reverse phase high-performance liquid chromatography afforded (2-benzo[b]thiophen-3-yl-cyclopropylmethyl)-dimethyl-amine (246 mg, 71%) as an oily trifluoroacetic acid salt. $^1$H NMR (500 MHz, d4-MeOH) 7.94 (1H, d, J=7.94 Hz), 7.86 (1H, d, J=7.93 Hz), 7.42 (1H, t, J=7.94), 7.37 (1H, t, J=7.94), 7.21 (1H, s), 3.44 (1H, dd, J=13.12, 6.71 Hz), 3.22 (1H, dd, J=13.12, 8.24 Hz), 2.97 (6H, s), 2.28 (1H, p, J=4.6 Hz), 1.56 (1H, m), 1.20 (2H, m). LC-MS: 1.10 min; 232.2 (MH)+.

EXAMPLE 168

(2-Benzo[b]thiophen-3-yl-cyclopropylmethyl)-methyl-amine

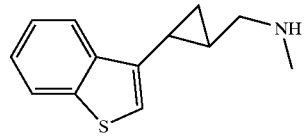

(2-Benzo[b]thiophen-3-yl-cyclopropylmethyl)-methyl-amine was prepared (191 mg, 58%) in a manner and scale similar to the above example. $^1$H NMR (500 MHz, d4-MeOH) 8.00 (1H, d, J=7.94 Hz), 7.91 (1H, d, J=7.93 Hz), 7.47 (1H, t, J=7.94), 7.42 (1H, t, J=7.94), 7.23 (1H, s), 3.34 (1H, dd, J=13.12, 7.02 Hz), 3.14 (1H, dd, J=12.82, 7.94 Hz), 2.82 (3H, s), 2.29 (1H, p, J=4.9 Hz), 1.54 (1H, m), 1.20 (2H, m). LC-MS: 1.12 min; 218.12 (MH)+.

EXAMPLE 169

(2-Benzo[b]thiophen-3-yl-cyclopropylmethyl)-ethyl-amine

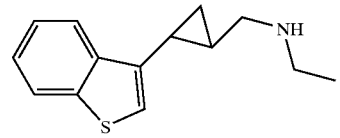

(2-Benzo[b]thiophen-3-yl-cyclopropylmethyl)-ethyl-amine was prepared (184 mg, 53%) in a manner and scale similar to the above example. $^1$H NMR (500 MHz, d4-MeOH) 7.94 (1H, d, J=7.63 Hz), 7.85 (1H, d, J=7.94 Hz), 7.42 (1H, t, J=7.93), 7.36 (1H, t, J=7.93), 7.17 (1H, s), 3.31 (1H, m [partially obscured by solvent peak]), 3.13 (2H, q, J=7.32 Hz), 3.07 (1H, dd, J=12.82, 7.94 Hz), 2.23 (1H, m), 1.48 (1H, m), 1.34 (3H, t, J=7.32 Hz), 1.15 (2H, t, J=7.32 Hz). LC-MS: 1.16 min; 232.15 (MH)$^+$.

EXAMPLE 170

(2-Benzo[b]thiophen-3-yl-cyclopropylmethyl)-ethyl-methyl-amine

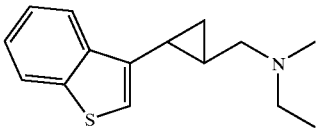

(2-Benzo[b]thiophen-3-yl-cyclopropylmethyl)-ethyl-methyl-amine was prepared (274 mg, 76%) in a manner and scale similar to the above example. $^1$H NMR (500 MHz, d4-MeOH) 7.94 (1H, d, J=7.94 Hz), 7.86 (1H, d, J=7.94 Hz), 7.42 (1H, t, J=7.93), 7.37 (1H, t, J=7.93), 7.21 (1H, s), 3.52 (0.5H, dd, J=13.43, 6.71 Hz), 3.39 (1.5H, m), 3.22 (2H, m), 2.95 (3H, s), 2.28 (1H, m), 1.55 (1H, m), 1.37 (3H, t, J=7.33 Hz), 1.20 (2H, m). LC-MS: 1.14 min; 246.14 (MH)$^+$.

EXAMPLE 171

(2-Benzo[b]thiophen-3-yl-cyclopropylmethyl)-diethyl-amine

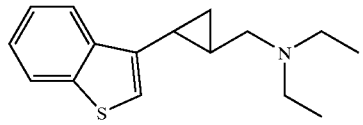

(2-Benzo[b]thiophen-3-yl-cyclopropylmethyl)-diethyl-amine was prepared (314 mg, 84%) in a manner and scale similar to the above example. $^1$H NMR (500 MHz, d4-MeOH) 7.94 (1H, d, J=7.93 Hz), 7.84 (1H, d, J=7.93 Hz), 7.41 (1H, t, J=7.93), 7.35 (1H, t, J=7.93), 7.19 (1H, s), 3.45 (1H, dd, J=13.73, 6.71 Hz), 3.33 (4H, m), 3.22 (1H, dd, J=13.74, 7.93 Hz), 2.28 (1H, m), 1.52 (1H, m), 1.34 (6H, 2t, J=7.33 Hz), 1.19 (2H, m). LC-MS: 1.17 min; 260.16 (MH)$^+$.

EXAMPLE 172

1-(2-Benzo[b]thiophen-3-yl-cyclopropylmethyl)-pyrrolidine

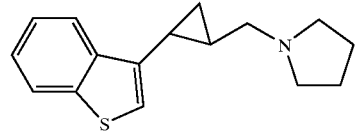

1-(2-Benzo[b]thiophen-3-yl-cyclopropylmethyl)-pyrrolidine was prepared (318 mg, 86%) in a manner and scale similar to the above example. $^1$H NMR (500 MHz, d4-MeOH) 7.93 (1H, d, J=7.93 Hz), 7.84 (1H, d, J=7.93 Hz), 7.41 (1H, t, J=7.93), 7.35 (1H, t, J=7.93), 7.18 (1H, s), 3.70 (2H, m), 3.44 (1H, dd, J=13.12, 6.71 Hz), 3.26 (1H, dd, J=13.12, 7.94 Hz), 3.15 (2H, m), 2.25 (1H, m), 2.15 (2H, m), 2.02 (2H, m), 1.55 (1H, m), 1.15 (1H, m). LC-MS: 1.15 min; 258.13 (MH)$^+$.

EXAMPLE 174

Trans-2-[5-cyanoindol-3-yl]-1-(3-(N,N-dimethylamino)propyl)cyclopropane

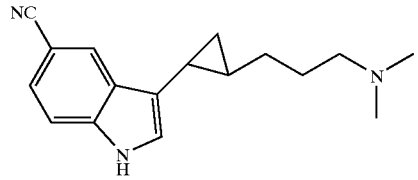

Sodium hydride (60% in oil, 120 mg, 0.02 mmol) was washed with hexanes to remove oil and was then suspended in THF (60 mL). Triethylphosponoacetate (0.60 mL, 3.02 mmol) was added dropwise and the solution was stirred for 1.5 h. Trans-2-[5-Cyano-1-(p-toluenesulfonyl)indol-3-yl]cyclopropane-carboxaldehyde (1.0 g, 2.74 mmol) was added as a solid and the reaction stirred for a further 3 h. The solvent was removed in vacuo and the residue was taken up in water (20 mL) and extracted with ethyl acetate (3×20 mL). The organic layer was dried and the solvent was removed in vacuo. The material was purified by chromatography on silica gel (20% ethyl acetate in hexanes) to provide 0.91 g (76%) of ethyl trans-2-[5-cyano-1-(p-toluenesulfonyl)indol-3-yl]cyclopropaneacrylate as a white solid: $^1$H NMR (400 MHz, CDCl$_3$) 8.04 (1H, d, J=8.6 Hz), 7.87 (1H, s,), 7.75 (2H, d, J=6.7 Hz), 7.57 (1H, dd, J=8.6, 1.6 Hz), 7.36 (1H, s), 7.27 (2H, d, J=6.8 Hz), 6.61 (1H, dd, J=15.4, 9.8 Hz), 5.96 (1H, d, J=15.4 Hz), 4.21 (2H, q, J=7.1 Hz), 2.37 (3H, s), 2.10 (1H, m), 1.75 (1H, m), 1.42 (1H, m), 1.34 (1H, m), 1.32 (3H, t, J=7.0 Hz); MS m/e 457.1 (M+Na).

Trans-2-[5-cyano-1-(p-toluenesulfonyl)indol-3-yl]cyclopropaneacrylate (850 mg, 1.96 mmol) was dissolved in THF and cooled to −40° C. Lithium aluminum hydride was added and the reaction stirred at −25° C. for 30 min. The reaction was quenched with ethyl acetate (20 mL) and stirred 10 min. Then water (0.15 mL) was added and the reaction stirred 2 min. Sodium hydroxide (1N, 0.45 mL) was added and the reaction was stirred 2 min, followed by final addition of water (0.15 mL) and stirring 15 min. The reaction was filtered through celite and sand and the filtrate was evaporated. The residue was dissolved in ethyl acetate (5 mL) and then ethanol (20 mL) and 10% palladium on carbon (200 mg) were added. The reaction was stirred under an atmosphere of hydrogen for 1 h. The reaction was filtered through celite and sand and the filtrate was evaporated. The residue was purified on a silica gel column (33% to 40% ethyl acetate in hexanes) to provide 318 mg of a 1:1 mixture of Trans-2-[5-cyanoindol-3-yl]-1-(3-hydroxypropyl)cyclopropane and an unidentified compound: $^1$H NMR (400 MHz, CDCl$_3$) 8.04 (0.5H, d, J=7.6 Hz), 8.02 (0.5H, d, J=8.0 Hz), 7.92 (0.5H, s), 7.85 (0.5H, s), 7.74 (2H, d, J=8.4 Hz), 7.52 (1H, m), 7.42 (0.5H, s), 7.25 (2H, d, J=8.0 Hz), 7.25 (0.5H, buried), 3.72 (1H, t, J=6.5 Hz), 3.61 (1H, t, J=6.4 Hz), 2.92 (0.5H, 6 peaks, J=6.9 Hz), 2.36 (3H, s), 1.78–1.24 (6H, m), 1.04 (0.5H, m), 0.90 (0.5H, m), 0.83 (0.5H, m); MS m/e 417.1 (M+Na).

Oxalyl chloride (0.10 mL, 1.19 mmol) in methylene chloride (50 mL) was cooled to −78° C. and DMSO (0.095 mL, 1.34 mmol) was added dropwise. After stirring 10 min, an impure sample of Trans-2-[5-cyanoindol-3-yl]-1-(3-hydroxypropyl)cyclopropane (318 mg) in methylene chloride (5 mL) was added dropwise. Stirred 20 min and added triethylamine (0.61 mL) dropwise. Allowed reaction to slowly warm to room temperature and added water (10 mL). The organic layer was dried with magnesium sulfate and the solvent was removed in vacuo. The residue was purified by chromatography on silica gel (33% to 40% ethyl acetate in hexanes) to give 296 mg of a 1:1 mixture of Trans-2-[5-cyanoindol-3-yl]-1-(3-oxopropyl)cyclopropane and an unknown compound: $^1$H NMR (400 MHz, CDCl$_3$) 9.85 (0.5H, t, J=1.4 Hz), 9.73 (0.5H, t, J=1.4 Hz), 8.04 (0.5H, d, J=8.7 Hz), 8.03 (0.5H, J=8.7 Hz), 7.90 (0.5H, s), 7.83 (0.5H, s), 7.75 (2H, m), 7.54 (1H, m), 7.45 (0.5H, s), 7.25 (2.5H, buried), 2.93 (0.5H, 6 peaks 7.0 Hz), 2.65 (1H, t, J=7.1 Hz, 2.43 (1H, t, J=6.1 Hz), 2.36 (3H, s), 1.92–1.35 (4H, m), 1.32 (1.5H, d, J=7.0 Hz), 1.07 (0.5H, m), 0.93 (0.5H, m), 0.83 (0.5H, m); MS m/e 393.2 (M+H).

A mixture of Trans-2-[5-cyanoindol-3-yl]-1-(3-oxopropyl)cyclopropane and byproduct (33 mg of mixture) was dissolved in THF (0.25 mL) and placed in a vial along with ethanol (2 mL) and an amine (0.25 mmol). Finally sodium triacetoxyborohydride (53 mg, 0.25 mmol) was added and the vial was sealed and shaken while being heated at 45° C. for 1 h. Then 0.5 mL of aqueous sodium hydroxide (5N) was added to the vial. The vial was sealed and shaken while being heated at 65° C. for 45 min. Most of the solvent was removed in vacuo, and the residue was taken up in aqueous sodium bicarbonate (10 mL) and extracted with ethyl acetate (2×5 mL). The organic layer was dried with magnesium sulfate and evaporated. The residue was purified using reverse phase preparative HPLC with a methanol/water gradient containing 0.1% trifluoroacetic acid to give trans-2-[5cyanoindol-3-yl]-1-(3-(N,N-dimethylamino) propyl)cyclo-propane. LC-MS (column=YMC ODS s7, 3×50 mm, start % B=0, final % B=100, gradient time=2 min, flow rate=5 ml/min) m/e 268.3 (M+H)$^+$, $t_R$ 1.05.

EXAMPLE 175

Trans-2-[5-cyanoindol-3-yl]-1-(3-(N-methylamino) propyl)cyclopropane

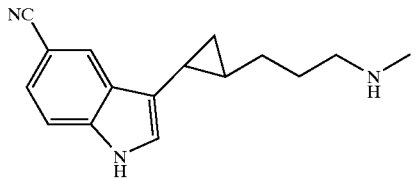

This compound was prepared in a manner similar to the above example. LC-MS (column=YMC ODS s7, 3×50 mm, start % B=0, final % B=100, gradient time=2 min, flow rate=5 ml/min) m/e 254.3 (M+H)$^+$, $t_R$ 1.09.

EXAMPLE 176

Trans-2-[5-cyanoindol-3-yl]-1-(3-(N-ethylamino) propyl)cyclopropane

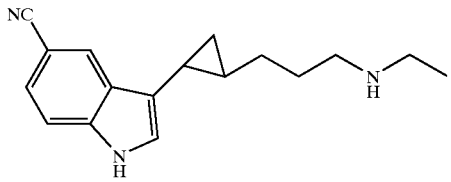

This compound was prepared in a manner similar to the above example. LC-MS (column=YMC ODS s7, 3×50 mm, start % B=0, final % B=100, gradient time=2 min, flow rate=5 ml/min) m/e 268.3 (M+H)$^+$, $t_R$ 1.13.

EXAMPLE 177

Trans-2-[5-cyanoindol-3-yl]1-(3-(N,N-diethylamino) propyl)cyclopropane

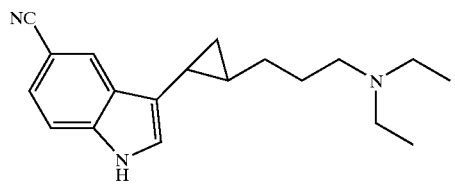

This compound was prepared in a manner similar to the above example. LC-MS (column=YMC ODS s7, 3×50 mm, start % B=0, final % B=100, gradient time=2 min, flow rate=5 ml/min) m/e 296.3 (M+H)$^+$, $t_R$ 1.15.

EXAMPLE 178

Trans-2-[5-cyanoindol-3-yl]-1-(3-(N-ethyl-N-methylamino)propyl)-cyclopropane

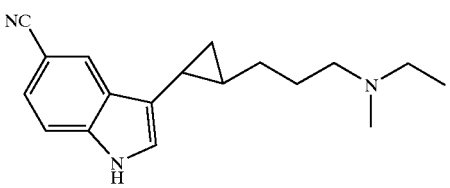

This compound was prepared in a manner similar to the above example. LC-MS (column=YMC ODS s7, 3×50 mm, start % B=0, final % B=100, gradient time=2 min, flow rate=5 ml/min) m/e 282.3 (M+H)$^+$, $t_R$ 1.12.

EXAMPLE 179

Trans-2-[5-cyanoindol-3-yl]-1-(3-(1-pyrrolidino) propyl)cyclopropane

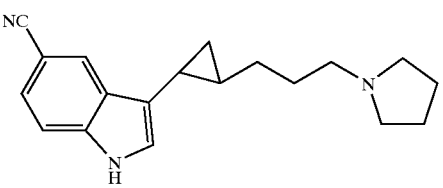

This compound was prepared in a manner similar to the above example. LC-MS (column=YMC ODS s7, 3×50 mm, start % B=0, final % B=100, gradient time=2 min, flow rate=5 ml/min) m/e 294.2 (M+H)$^+$, $t_R$ 1.07.

EXAMPLE 180

Trans-2-[5-cyanoindol-3-yl]-1-(3-(N-benzyl-N-methylamino)propyl)cyclopropane

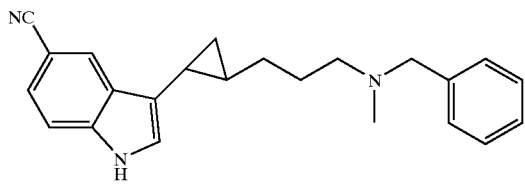

This compound was prepared in a manner similar to the above example. LC-MS (column=YMC ODS s7, 3×50 mm, start % B=0, final % B=100, gradient time=2 min, flow rate=5 ml/min) m/e 344.3 (M+H)$^+$, $t_R$ 1.28.

EXAMPLE 181 cis-1-(N-methylaminomethyl)-2-[5-fluoroindol-3-yl]-cyclopropane

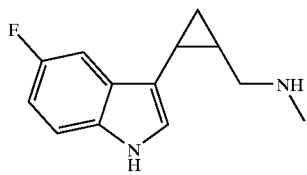

This compound was prepared in a manner similar to Example 117. LC-MS (column=YMC ODS s7, 3×50 mm, start % B=0, final % B=100, gradient time=2 min, flow rate=5 ml/min) m/e 219.2 (M+H)$^+$, $t_R$ 0.85.

EXAMPLE 182 cis-1-(N-ethylaminomethyl)-2-[5-fluoroindol-3-yl]-cyclopropane

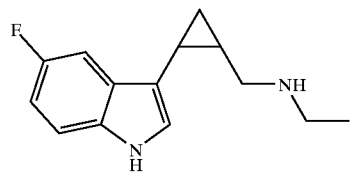

This compound was prepared in a manner similar to Example 117. LC-MS (column=YMC ODS s7, 3×50 mm, start % B=0, final % B=100, gradient time=2 min, flow rate=5 ml/min) m/e 233.3 (M+H)$^+$, $t_R$ 0.92.

EXAMPLE 183 cis-1-(N,N-diethylaminomethyl)-2-[5-fluoroindol-3-yl]-cyclopropane

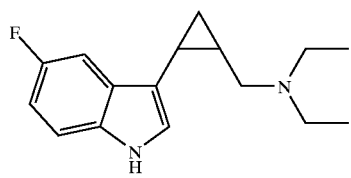

This compound was prepared in a manner similar to Example 117. LC-MS (column=YMC ODS s7, 3×50 mm, start % B=0, final % B=100, gradient time=2 min, flow rate=5 ml/min) m/e 261.2 (M+H)$^+$, $t_R$ 1.00.

EXAMPLE 184 cis-1-(N-ethyl-N-methylaminomethyl)-2-[5-fluoroindol-3-yl]-cyclopropane

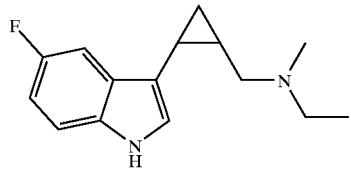

This compound was prepared in a manner similar to. Example 117. LC-MS (column=YMC ODS s7, 3×50 mm, start % B=0, final % B=100, gradient time=2 min, flow rate=5 ml/min) m/e 247.2 (M+H)$^+$, $t_R$ 0.96.

EXAMPLE 185 cis-1-(1-pyrrolidino)-2-[5-fluoroindol-3-yl]-cyclopropane

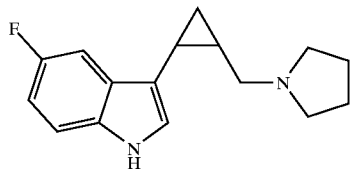

This compound was prepared in a manner similar to Example 117. LC-MS (column=YMC ODS s7, 3×50 mm, start % B=0, final % B=100, gradient time=2 min, flow rate=5 ml/min) m/e 259.2 (M+H)$^+$, $t_R$ 0.97.

EXAMPLE 186 cis-1-(N-benzyl-N-methylaminomethyl)-2-[5-fluoroindol-3-yl]-cyclopropane

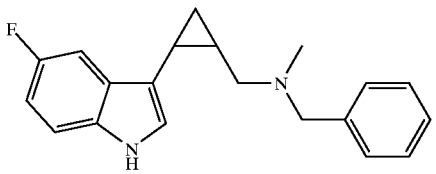

This compound was prepared in a manner similar to Example 117. LC-MS (column=YMC ODS s7, 3×50 mm, start % B=0, final % B=100, gradient time=2 min, flow rate=5 ml/min) m/e 309.2 (M+H)$^+$, $t_R$ 1.18.

EXAMPLE 187

S,S-Trans-2-[5-Cyanoindol-3-yl]-1-(trimethylammoniummethyl)cyclopropane trifluoroacetate

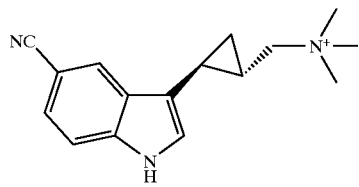

A solution of S,S-trans-2-[5-cyanoindol-3-yl]-1-(N,N-dimethylamino)-cyclopropane (82 mg, 0.34 mmol) in THF (10 mL) was treated with ethylmagnesium bromide (1 M, 0.40 mL, 0.40 mmol) and stirred 1 h at room temperature. Iodomethane (0.027 mL, 0.43 mmol) was added, and the reaction was stirred 1 h. The solvent was removed in vacuo. The residue was purified using reverse phase preparative HPLC with a methanol/water gradient containing 0.1% trifluoroacetic acid. The product was obtained as a trifluoroacetate salt with a yield of 10 mg (8%): $^1$H NMR (400 MHz, DMSO-d$_4$) 8.14 (1H, s), 7.51 (1H, d, J=8.6 Hz), 7.43 (1H, dd, J=8.4, 1.5 Hz), 7.39 (1H, d, J=2.1 Hz), 3.61 (1H, dd, J=13.1, 6.3 Hz), 3.31 (1H, dd, J=13.0, 6.2 Hz), 3.13 (9H, s), 2.10 (1H, m), 1.44 (1H, m), 1.22 (1H, m), 1.05 (1H, m); MS m/e 255.2 (M+).

EXAMPLE 188

S,S-trans-2-[5-cyano-1-methylindol-3-yl]-1-(N,N-dimethylamino)-cyclopropane

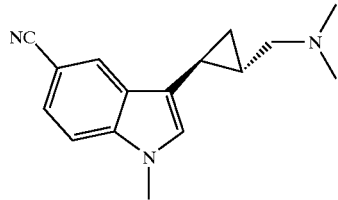

A solution of S,S-trans-2-[5-cyanoindol-3-yl]-1-(N,N-dimethylamino)-cyclopropane (90 mg, 0.38 mmol) in THF (5 mL) was treated with potassium tert-butoxide (46 mg, 0.41 mmol) and stirred for 1 h at room temperature. Dimethyl sulfate (52 mg, 0.41 mmol) was added and the reaction was stirred for 3 h. The THF was removed in vacuo and the remaining aqueous suspension was extracted with ethyl acetate (4×5 mL). The organic layer was dried with magnesium sulfate and the solvent was removed in vacuo. The residue was purified by chromatography on silica gel (97:3 chloroform/2M ammonia in methanol) to give S,S-trans-2-[5-cyano-1methylindol-3-yl]-1-(N,N-dimethylamino)-cyclopropane in a yield of 62 mg (65%): $^1$H NMR (400 MHz, CDCl$_3$) 8.02 (1H, d, J=1.2 Hz), 7.42 (1H, dd, J=8.8, 1.2 Hz), 7.28 (1H, d, J=8.4 Hz), 6.84 (1H, s), 3.73 (3H, s), 2.44 (1H, dd, J=13.2, 6.8 Hz), 2.34 (1H, dd, J=13.1, 6.8 Hz), 2.33 (6H, s), 1.75 (1H, m), 1.21 (1H, m), 0.90 (1H, m), 0.84 (1H, m); MS m/e 254.1 (M+H).

EXAMPLE 189

S,S-trans-2-[5-cyano-1-ethylindol-3-yl]-1-(N,N-dimethylamino)-cyclopropane

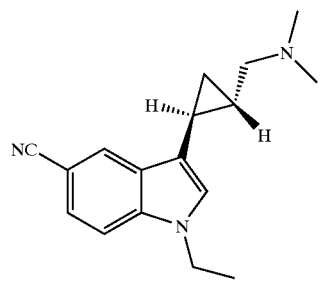

Using the above method with diethyl sulfate as the reagent produced S,S-trans-2-[5-cyano-1-ethylindol-3-yl]-1-(N,N-dimethylamino)-cyclopropane: $^1$H NMR (400 MHz, CDCl$_3$) 8.03 (1H, d, J=1.5 Hz), 7.40 (1H, dd, J=8.8, 1.6 Hz), 7.31 1H, d, J=8.4 Hz), 6.90 1H, s), 4.10 (2H, q, J=7.2 Hz), 2.44 (1H, dd, J=12.9, 6.5 Hz), 2.34 (1H, dd, J=13.0, 6.8 Hz), 2.33 (6H, s), 1.74 (1H, m), 1.23 (1H, m), 0.88 (1H, m), 0.81 (1H, m); MS m/e 268.1 (M+H).

EXAMPLE 190

Resolution of (2-Benzo[b]thiophen-3-yl-cyclopropylmethyl)-dimethyl-amine

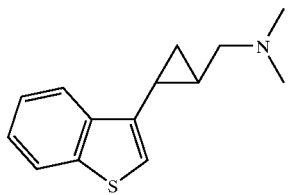

Racemic (2-Benzo[b]thiophen-3-yl-cyclopropylmethyl)-dimethyl-amine (68 mg) was resolved by preparative chiral HPLC on a Chiracel Prep OD column using as the eluant 5% EtOH, 0.1% diethylamine in hexane at 60 mL/min. Two fractions were isolated and concentrated in vacuo.

EXAMPLE 190A (−)-(2-Benzo[b]thiophen-3-yl-cyclopropylmethyl)-dimethyl-amine (28 mg).

EXAMPLE 190B (+)-(2-Benzo[b]thiophen-3-yl-cyclopropylmethyl)-dimethyl-amine (19 mg): $^1$H NMR (300 MHz, CDCl3) 7.93

(1H, d, J=7.32 Hz), 7.84 (1H, d, J=6.95 Hz), 7.38 (2H, m), 7.26 (1H, s), 2.49 (2H, m), 2.37 (6H, s), 1.91 (1H, m), 1.34 (1H, m), 0.94 (2H, m). LC-MS: 1.56 min; 232.10 (MH)⁺.

EXAMPLE 191

[2-(1H-Indol-6-yl)-cyclopropylmethyl]-dimethyl-amine

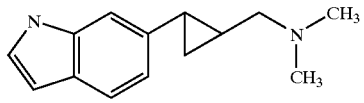

6-Methoxyindole (1.47 g, 10.00 mmol) was cooled to 0° C. in methylene chloride and BBr₃ (2 M in methylene chloride, 25 mL, 50.00 mmol) was added. After stirring 16 h at room temperature, TLC analysis indicated the reaction was complete. The reaction was quenched with water and the layers separated. The organic layers were washed with 1 N NaOH. The basic aqueous layers were acidified with conc. HCL, extracted with methylene chloride, dried over anhydrous magnesium sulfate, and concentrated in vacuo to give the crude 6-hydroxyindole which was used directly for the next reaction.

The crude 6-hydroxyindole and N-phenyltrifluoromethanesulfonimide (3.93 g, 11.00 mmol) were dissolved in methylene chloride and cooled to 0° C. Triethylamine (1.20 g, 12.00 mmol) was added and the reaction allowed to warm to room temperature and stirred for 16 h. TLC analysis showed complete conversion to product. The reaction was washed with 1 N HCl, 2 M K₂CO₃, dried over anhydrous magnesium sulfate, filtered, and concentrated in vacuo to give 6-trifluoromethanesulfonyl-1H-indole as an oil which solidified on standing. This material was used directly for the next reaction.

Tris(dibenzylideneacetone) dipalladium (45 mg, 0.05 mmol) and tri-o-tolylphosphine (120 mg, 0.20 mmol) were stirred in DMF at room temperature for 30 min. The 4-trifluoromethanesulfonyl-1H-indole, N-methoxy-N-methyl acrylamide (1.26 g, 11.00 mmol), and triethylamine (2.20 g, 22.00 mmol) were added and the reaction was heated to 120° C. for 4 h. The reaction was allowed to cool and the solvent removed in vacuo. The residue was taken up in methylene chloride, washed with water, dried over anhydrous magnesium sulfate, filtered, and concentrated in vacuo to give a brown solid. The solid was purified by flash chromatography (EtOAc, hexanes) to give 3-(1H-indol-6-yl)-N-methoxy-N-methyl-acrylamide (0.90 g, 39% yield for the three reactions). ¹H NMR (CDCl₃): δ8.385 (bs, 1H), 7.86 (d, J=18.6 Hz, 1H), 7.62 (d, J=8.5 Hz, 1H), 7.57 (s, 1H), 7.25 (d, J=8.5 Hz, 1H), 7.25 (m, 1H), 7.03 (d, J=18.6 Hz, 1H), 6.55 (m, 1H), 3.78 (s, 3H), 3.32 (s, 3H).

Trimethylsulfoxonium iodide (2.20 g, 10.00 mmol) was added to a suspension of sodium hydride (60% dispersion in oil, 0.40 g, 10.00 mmol) in anhydrous THF and stirred at room temperature for 1 h. 3-(1H-Indol-6-yl)-N-methoxy-N-methylacrylamide (0.90 g, 3.90 mmol) was dissolved in anhydrous THF and added dropwise to the cloudy white suspension. The mixture was stirred for 16 h at room temperature. The reaction was quenched with a solution of saturated ammonium chloride. Water was added and the solution was extracted with methylene chloride. The organic layer was dried over anhydrous magnesium sulfate, filtered, and concentrated in vacuo to give 2-(1H-indol-6-yl)-cyclopropanecarboxylic acid methoxy-methyl-amide as a yellowish solid (0.96 g, 100%). LC-MS: MH+: 245.12, 72% AP.

Lithium aluminum hydride (30 mg, 7.86 mmol) was suspended in anhydrous THF at −45° C. (dry ice/acetonitrile) with stirring. The 2-(1H-indol-6-yl)-cyclopropanecarboxylic acid methoxy-methyl-amide was dissolved in anhydrous THF and added dropwise over a period of 10 min. The reaction was stirred for 3 h at this temperature, diluted with ether, then quenched with 1.5 mL of 1 N sodium hydroxide solution. The mixture was allowed to warm to room temperature and the resulting white solid was filtered and washed with ether. The ether layer was then concentrated in vacuo to give 2-(1H-indol-6-yl)-cyclopropanecarbaldehyde as a yellow solid. This material was used immediately for the next reaction.

The crude 2-(1H-indol-6-yl)-cyclopropanecarbaldehyde was dissolved in methanol at room temperature with stirring. Dimethylamine (1M solution in THF, 20.00 mL, 20.00 mmol) was added followed by sodium triacetoxyborohydride (4.24 g, 20.00 mmol) After 15 h of stirring at room temperature, the solution was concentrated to dryness in vacuo. The residue was then partitioned between methylene chloride and 1 N NaOH solution. The layers were separated, and the organic layer dried over anhydrous magnesium sulfate, filtered, and concentrated in vacuo. The crude amine was purified by flash chromatography (50% MeOH/EtOAc) to give [2-(1H-indol-6-yl)-cyclopropylmethyl]-dimethyl-amine as a yellow solid (0.62 g, 74% for the two reactions). ¹H NMR (CDCl₃): δ 8.61 (bs, 1H), 7.51 (d, J=8.4 Hz, 1H), 7.08 (t, J=2.7 Hz, 1H), 7.06 (s, 1H), 6.86 (dd, J=11.4, 1.8 Hz, 1H), 6.47 (m, 1H), 2.51 (m, 1H), 2.35 (s, 7H), 1.85 (m, 1H), 0.99 (m, 1H), and 0.85 (m, 1H); LCMS: MH+: 215.16, 78% AP.

EXAMPLE 192

6-(2-Dimethylaminomethyl-cyclopropyl)-1H-indole-3-carbonitrile

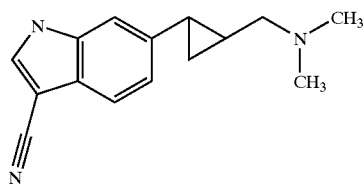

Phosphorous oxychloride (0.23 g, 1.47 mmol) was added to dimethylformamide (2 mL) at room temperature with stirring. After 15 min, [2-(1H-indol-6-yl)-cyclopropylmethyl]-dimethyl-amine (0.35 g, 1.64 mmol) in DMF (3 mL) was added dropwise. After 20 h, the reaction was quenched with ice and 1 N NaOH. The solution was extracted with methylene chloride, dried over anhydrous magnesium sulfate, filtered, and concentrated in vacuo to give 6-(2-dimethylaminomethyl-cyclopropyl)-1H-indole-3-carbaldehyde of an oil (0.25 g, 63%) that was used for the next reaction without purification. ¹H NMR (CDCl₃): δ 9.84 (s, 1H), 8.14 (d, J=8.4 Hz, 1H), 7.97 (s, 1H), 7.14 (d, J=8.4 Hz, 1H), 7.05 (s, 1H), 2.64 (s, 1H), 2.56 (s, 7H), 1.91 (m, 1H), 1.27 (m, 1H), 1.06 (m, 1H), and 0.92 (m, 1H).

In 5 mL of acetic acid were combined the crude 6-(2-dimethylaminomethylcyclo-propyl)-1H-indole-3-carbaldehyde, ammonium hydrogen phosphate (0.99 g, 7.50 mmol), and nitropropane (0.09 g, 1.03 mmol.). The mixture was stirred and heated to a gentle reflux for 16 h. Water was added after cooling reaction to room temperature, and the mixture was made basic by the addition of 1 N NaOH. The mixture was extracted with methylene chloride, dried over anhydrous magnesium sulfate, filtered, and concentrated in vacuo to give a brown oil. The oil was purified by flash chromatography (50% methanol/ethyl acetate) to give 6-(2-dimethylaminomethyl-cyclopropyl)-1H-indole-3-carbonitrile as an amber oil (93 mg, 38%). $^1$H NMR (CDCl$_3$): δ 7.58 (m, 2H), 6.99 (m, 2H), 5.75 (s, 1H), 2.46 (m, 1H), 2.33 (s, 7H), 1.89 (m, 1H), 1.20 (m, 1H), 0.98 (m, 1H), 0.86 (m, 1H); FIMS: 238.2 (M−H); LCMS: 72% AP.

EXAMPLE 193

3-[2-(2-Dimethylamino-ethyl)-cyclopropyl]-1H-indole-5-carbonitrile

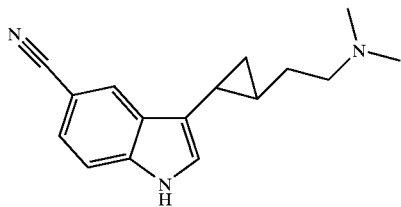

A procedure similar to Example 144, but using dimethylamine in the last step, was used to give 3-[2-(2-Dimethylamino-ethyl)-cyclopropyl]-1H-indole-5-carbonitrile (25.5 mg, 48%). MS m/e 254.22 (MH$^+$)

LCMS Method

Products were analyzed on a Shimadzu analytical high-performance liquid chromatography system equipped with a Micromass ESI mass spectrometer (positive ion mode). Elution was through a 3×50 mm YMC ODS-A C-18 S7 reverse phase column using the following gradient method:

Start mobile phase composition: 10% methanol-90% water-0.1% trifluoroacetic acid
Final mobile phase composition: 90% methanol-10% water-0.1% trifluoroacetic acid
Gradient time=2 min
Hold time=1 min
Flow rate=5 ml/min
Wavelength=220 nm

Serotonin Transporter Binding Assay

HEK-293 cells that stably express human serotonin transporters (HEK-hSERT cells) were grown at 37° C. in 5% CO$_2$ as a monolayer in medium consisting of EMEM supplemented with 10% fetal bovine serum and G418 sulfate (500 μg/ml). To prepare membranes for radioligand binding experiments, cells were rinsed twice with phosphate-buffered saline (138 mM NaCl, 4.1 mM KCl, 5.1 mM Na$_2$PO$_4$, 1.5 mM KH$_2$O$_4$, 11.1 mM glucose, pH 7.4). Cells were transferred from plates to polypropylene tubes (16×100 mm), centrifuged at 1,200×g for 5 min and were frozen at −80° C. until assay. Following centrifugation, pellets were resuspended by homogenization in buffer consisting of 50 mM Tris (pH 7.7 at 25° C.), 120 mM NaCl and 5 mM KCl and then centrifuged at 32,000×g for 10 min. Following centrifugation, supernatants were discarded and pellets were resuspended in buffer consisting of 50 mM Tris (pH 7.4 at 25° C.), 150 mM NaCl and 5 mM KCl. Membrane homogenates (200 μl/plate) were incubated with 1 nM [$^3$H]-citalopram (specific activity=85 Ci/mmol) and increasing concentrations of test compounds for 1 hr at 25° C. in a total volume of 250 μl. The assay buffer consisted of 50 mM Tris (pH 7.4 at 25° C.), 120 mM NaCl and 5 mM KCl (pH 7.4 with conc. HCl). Plates were incubated for 1 hr at 25° C., then filtered through 0.5% PEI treated Whatman GF/B filters using a Brandel cell harvester. Filters were washed three times with 3 ml of ice-cold tris wash buffer. Non-specific binding was defined with 10 μM fluoxetine. Amount of radioligand bound in the presence and absence of competitor was analyzed by plotting (−)log drug concentration versus the amount of radioligand specifically bound. The midpoint of the displacement curve (IC$_{50}$, nM), signifies the potency. K$_i$ values were calculated using the method of Cheng and Prusoff (1973).

Dopamine Binding Assay

HEK-293 cells that stably express recombinant human dopamine D$_{2L}$ receptors (HEK-D$_{2L}$ cells) were grown at 37° C. in 5% CO$_2$ as a monolayer in medium consisting of EMEM supplemented with 10% fetal bovine serum and G418 sulfate (500 μg/ml). To prepare membranes for radioligand binding experiments, cells were rinsed twice with phosphate-buffered saline (138 mM NaCl, 4.1 mM KCl, 5.1 mM Na$_2$PO$_4$, 1.5 mM KH$_2$PO$_2$ 11.1 mM glucose, pH 7.4), and incubated for 5–10 min. at 4° C. in hypotonic lysis buffer consisting of 10 mM Tris (pH 7.4) and 5 mM EDTA. Cells were transferred from plates to polypropylene tubes (16×100 mm), homogenized and centrifuged at 32,000×g for 20 min. Following centrifugation, pellets were resuspended by homogenization in buffer consisting of 50 mM Tris (pH 7.7 at 25° C.) and 1 mM EDTA. Homogenates were stored at −80° C. until needed. On the day of an experiment, homogenates were thawed then centrifuged at 32,000×g for 20 min. Following centrifugation, supernatants were discarded and pellets were resuspended in assay buffer consisting of 50 mM Tris (pH 7.4 at 25° C.), 1 mM EDTA and 6 mM MgCl$_2$. Membrane homogenates (~5 μg) were incubated with 150 pM [$^3$H]-spiperone (Amersham Life Science) and increasing concentrations of test compounds for 1.5 hr at 22° C. in a total volume of 400 μl. Reactions were stopped by addition of ice-cold assay buffer and filtration over glass fiber filters (Whatman GFB, pre-soaked in 0.05% polyethylenimine) using a microtitre format Brandel cell harvester. Filters were washed with 3 ml of ice-cold assay buffer. Non-specific binding was defined with 2 μM (+)butaclamol. Ki values were calculated using the method of Cheng and Prusoff (1973). Protein concentrations were determined by the method of Bradford (1976) with BSA as a standard.

Compounds of the present invention demonstrating greater SERT binding than hD$_{2L}$ binding may be useful for the treatment of depression, anxiety disorders, premature ejaculation, chronic pain, obsessive-compulsive disorder, feeding disorders, premenstrual dysphoric disorder and panic disorders. Compounds of the present invention demonstrating greater hD$_{2L}$ binding than SERT binding may be useful for the treatment of various psychotic disorders including bipolar disorder and schizophrenia. Compounds which have a strong affinity to the hD$_{2L}$ receptor may exhibit dopamine receptor-related side effects such as rigidity, stiff posture and tics such as lip smacking, head turning and sudden arm movements.

In the table below, binding results are denoted as follows:

A: Ki<1 nM;
B: 1 nM<Ki<10 nM;
C: 10 nM<Ki<100 nM;
D: 100 nM<Ki<1000 nM;
E: Ki≧1000 nM.

| Example | Results SERT Ki (nM) | D2L Ki (nM) |
|---|---|---|
| 1 | A | E |
| 2 | B | D |
| 3 | A | D |
| 4 | A | E |
| 5 | A | E |
| 6 | B | E |
| 7 | B | D |
| 8 | B | D |
| 9 | B | D |
| 10 | B | D |
| 11 | B | D |
| 12 | B | D |
| 13 | B | D |
| 14 | C | D |
| 15 | C | D |
| 16 | C | D |
| 17 | B | C |
| 18 | B | C |
| 19 | B | C |
| 20 | B | E |
| 21 | B | C |
| 22 | B | D |
| 23 | C | C |
| 24 | C | D |
| 25 | B | D |
| 26 | B | C |
| 27 | B | C |
| 28 | C | E |
| 29 | C | C |
| 30 | B | C |
| 31 | C | C |
| 32 | C | C |
| 33 | C | D |
| 34 | B | B |
| 35 | B | E |
| 36 | C | C |
| 37 | C | C |
| 38 | B | E |
| 39 | B | C |
| 40 | B | C |
| 41 | B | C |
| 42 | B | C |
| 43 | B | C |
| 44 | B | B |
| 45 | C | D |
| 46 | B | D |
| 47 | C | D |
| 48 | B | D |
| 49 | C | D |
| 50 | B | C |
| 51 | B | D |
| 52 | C | D |
| 53 | C | D |
| 54 | C | D |
| 55 | C | D |
| 56 | C | D |
| 57 | C | C |
| 58 | C | C |
| 59 | C | C |
| 60 | C | D |
| 61 | C | C |
| 62 | B | C |
| 63 | C | C |
| 64 | C | C |
| 65 | C | C |
| 66 | C | D |
| 67 | C | C |
| 68 | B | C |
| 69 | C | D |
| 70 | C | D |
| 71 | C | C |
| 72 | C | D |
| 73 | B | C |
| 74 | B | E |
| 75 | C | C |
| 76 | C | C |
| 77 | C | D |
| 78 | B | D |
| 80 | C | C |
| 81 | C | C |
| 82 | C | C |
| 83 | B | B |
| 84 | B | D |
| 85 | C | E |
| 86 | C | D |
| 87 | C | D |
| 88 | B | E |
| 89 | B | E |
| 90 | B | D |
| 91 | B | C |
| 92 | C | E |
| 93 | B | E |
| 94 | A | E |
| 95 | B | E |
| 96 | B | D |
| 97 | B | D |
| 98 | B | D |
| 99 | B | D |
| 100 | C | E |
| 102 | B | D |
| 103 | B | D |
| 104 | C | D |
| 105 | C | D |
| 106 | C | D |
| 107 | C | D |
| 108 | C | D |
| 109 | B | D |
| 110 | B | D |
| 111 | B | C |
| 112 | C | D |
| 113 | C | D |
| 114 | C | D |
| 115 | C | D |
| 117 | B | E |
| 118 | C | E |
| 119 | B | D |
| 120 | B | D |
| 121 | A | E |
| 122A | A | E |
| 122B | B | E |
| 123 | C | E |
| 124 | B | E |
| 125 | B | D |
| 126 | C | D |
| 127a | C | E |
| 128a | C | E |
| 129a | C | E |
| 129b | B | E |
| 130a | D | E |
| 130b | B | E |
| 131 | B | D |
| 132 | C | D |
| 133 | C | D |
| 134 | B | E |
| 135 | B | C |
| 136 | C | E |
| 137 | C | E |
| 138 | C | E |
| 139 | C | C |

-continued

| Example | Results SERT Ki (nM) | D2L Ki (nM) |
|---|---|---|
| 140 | D | D |
| 141 | C | D |
| 142 | C | D |
| 143 | C | E |
| 144 | C | D |
| 145 | C | D |
| 147 | C | D |
| 148 | C | D |
| 149 | B | D |
| 150 | C |   |
| 151 | B |   |
| 152 | B | E |
| 153 | C | E |
| 154 | C |   |
| 155 | C | E |
| 156 | D |   |
| 157 | D |   |
| 158 | C | E |
| 159 | D |   |
| 160 | C | E |
| 161 | D |   |
| 162 | C | D |
| 164 | D |   |
| 165 | D |   |
| 166 | D |   |
| 167 | C | E |
| 168 | C |   |
| 169 | C | D |
| 170 | D |   |
| 171 | D |   |
| 172 | D |   |
| 174 | C | D |
| 175 | B | D |
| 176 | C | D |
| 177 | C |   |
| 178 | C | D |
| 179 | C | D |
| 180 | C | D |
| 181 | C | D |
| 182 | C | D |
| 183 | C | E |
| 184 | C | E |
| 185 | C | E |
| 186 | B | E |
| 187 | A |   |
| 188 | B |   |
| 189 | B |   |
| 190A | D |   |
| 190B | C | E |
| 191 | C |   |
| 192 | B |   |
| 193 | B |   |

What is claimed is:

1. A process for the preparation of a compound of Formula (d)

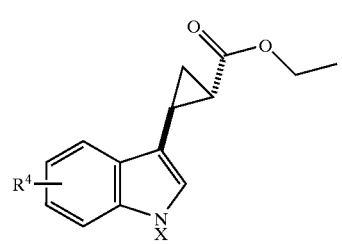

by reacting a compound of formula (b)

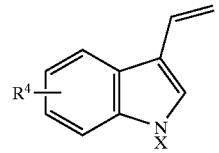

with a compound of formula (c)

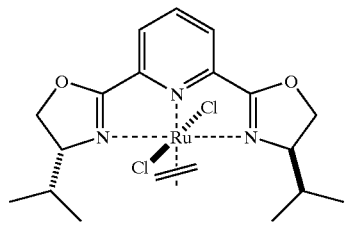

in the presence of ethyl diazoacetate and toluene, wherein $R^4$ is cyano, halo, nitro or $C_{1-3}$perfluoroalkyl and X is p-toluenesulfonyl, benzenesulfonyl, methansulfonyl or trifluoromethanesulfonyl.

2. A process for the preparation of a compound of Formula (d')

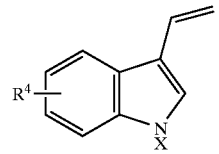

by reacting a compound of formula (b)

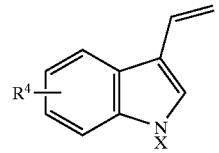

with a compound of formula (c)

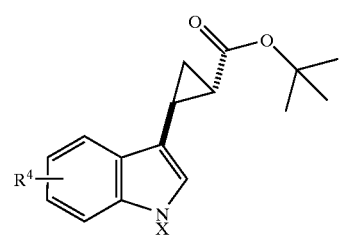

in the presence of tert-butyl diazoacetate and toluene, wherein $R^4$ is cyano, halo, nitro or $C_{1-3}$perfluoroalkyl and X is p-toluenesulfonyl, benzenesulfonyl, methansulfonyl or trifluoromethanesulfonyl.

* * * * *